US007041465B1

(12) United States Patent
Hultgren et al.

(10) Patent No.: US 7,041,465 B1
(45) Date of Patent: May 9, 2006

(54) ANTI-BACTERIAL COMPOUNDS DIRECTED AGAINST PILUS BIOGENESIS, ADHESION AND ACTIVITY; CO-CRYSTALS OF PILUS SUBUNITS AND METHODS OF USE THEREOF

(75) Inventors: Scott J. Hultgren, St. Louis, MO (US); Frederic G. Sauer, St. Louis, MO (US); Gabriel Waksman, St. Louis, MO (US); Klaus Fuetterer, St. Louis, MO (US); Devapriya Choudhury, Uppsala (SE); Stefan D. Knight, Uppsala (SE); Michelle Barnhart, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 09/637,216

(22) Filed: Aug. 11, 2000

Related U.S. Application Data

(60) Provisional application No. 60/148,280, filed on Aug. 11, 1999.

(51) Int. Cl.
*C12Q 1/68* (2006.01)
*C12N 1/20* (2006.01)
*G01N 33/554* (2006.01)
*A61K 38/00* (2006.01)
*C07K 1/00* (2006.01)

(52) U.S. Cl. .................. 435/7.32; 435/6; 435/252.1; 530/300; 530/350

(58) Field of Classification Search .................. 435/7.1; 530/300
See application file for complete search history.

(56) References Cited

U.S. PATENT DOCUMENTS

| 2,490,074 A | 12/1949 | Marty |
| 4,882,425 A | 11/1989 | Hull et al. |
| 5,336,159 A | 8/1994 | Cheng et al. |
| 5,551,949 A | 9/1996 | Kim et al. |

FOREIGN PATENT DOCUMENTS

| EP | 45665 | 2/1982 |
| EP | 1008366 | 6/2000 |
| WO | WO 95/14028 | 5/1995 |

OTHER PUBLICATIONS

Marklund et al. "Horizontal gene transfer of the *Escherichia coli* pap and prs pili operons as a mechanism for the development of tissue-specific adhesive properties". Mol. Microbiol. (1992), vol. 6, pp. 2225-2242.*
Database: PIR__68: pir2. Accession # S16400; S16400; Feb. 20, 1995.*
Abraham SN, et al., "Conservation of the D-Mannose-Adhesion Protein Among Type 1 Fimbriated Members of the Family Enterobacteriaceae", Nature, vol. 336, pp. 682-684 (1988).
Bohm, HJ, "The Computer Program LUDI: A New Method for the De Novo Design of Enzyme Inhibitors", J. Comp. Aid. Molec. Design, vol. 6, No. 1, pp. 61-78 (1992).
Choudhury D, et al., "X-ray Structure of the FimC-FimH Chaperone-Adhesin Complex from Uropathogenic *Escherichia coli*", Science, vol. 285, pp. 1061-1066 (1999).
Holmgren A, et al., "Crystal Structure of Chaperone Protein PapD Reveals an Immunoglobulin Fold", Nature, vol. 342, No. 6247, pp. 248-251 (1989).
Hultgren SJ, et al., "Pilus and Nonpilus Bacterial Adhesins: Assembly and Function in Cell Recognition", Cell, vol. 73, No. 5, pp. 887-901 (1993).
Hung DL, et al., "Molecular Basis of Two Subfamilies of Immunoglobulin-Like Chaperones", The EMBO J., vol. 15, No. 15, pp. 3792-3805 (1996).
Jones CH, et al., "The Chaperone-Assisted Membrane Release and Folding Pathway is Sensed by Two Signal Transduction Systems", The EMBO Journal, vol. 16, No. 21, pp. 6394-6406 (1997).
Jones CH, et al., "FimH Adhesin of Type 1 Pili is Assembled Into a Fibrillar Tip Structure in the *Enterobacteriaceae*", Proc. Natl. Acad. Sci. USA, vol. 92, pp. 2081-2085 (1995).
Krogfelt KA, et al., "Direct Evidence That The FimH Protein is the Mannose-Specific Adhesin of *Escherichia coli* Type 1 Fimbriae", Infection and Immunity, vol. 58, No. 6, pp. 1995-1998 (1990).
Kuehn MJ, et al., "Immunoglobulin-Like PapD Chaperone Caps and Uncaps Interactive Surfaces of Nascently Translocated Pilus Subunits", Proc. Natl. Acad. Sci. USA, vol. 88, pp. 10586-10590 (1991).
Kuehn MJ, et al., "Structural Basis of Pilus Subunit Recognition by the PapD Chaperone", Science, vol. 262, pp. 1234-1241 (1993).
Pellecchia M, et al., "Pilus Chaperone FimC-Adhesin FimH Interactions mapped by TROSY-NMR", Nature Structural Biology, vol. 6, No. 4, pp. 336-339 (1999).
Pellecchia M, et al., "NMR Solution Structure of the Periplasmic Chaperone FimC", Nature Structural Biology, vol. 5, No. 10, pp. 885-890 (1998).

(Continued)

*Primary Examiner*—Ardin H. Marschel
*Assistant Examiner*—Shubo (Joe) Zhou
(74) *Attorney, Agent, or Firm*—Senniger Powers

(57) ABSTRACT

Many Gram-negative pathogens assemble adhesive pili structures on their surfaces that allow them to colonize host tissues and cause disease. The present invention relates to novel compounds that mimic a chaperone G1 beta-strand or an amino terminal motif of a pilus subunit. The present invention also relates to the complex formed from the binding of such mimic compounds to the hydrophobic groove of a pilus subunit. Competitively interacting with the binding site of pili subunits will negatively affect the chaperone/usher pathway, which is one molecular mechanism by which Gram-negative bacteria assemble adhesive pili structures, and thus prevent or inhibit pilus assembly.

16 Claims, 31 Drawing Sheets

OTHER PUBLICATIONS

Sauer FG, et al., "Structural Basis of Chaperone Function and Pilus Biogenesis", Science, vol. 285, pp. 1058-1061 (1999).

Schembri MA, et al., "Linker Insertion Analysis of the FimH Adhesin of Type 1 Fimbriae in an *Escherichia coli* fimH-null background", FEMS Microbiol. Lett., vol. 137, pp. 257-263 (1996).

Slonim LN, et al., "Interactive Surface in the PapD Chaperone Cleft is Conserved in Pilus Chaperone Superfamily and Essential in Subunit Recognition and Assembly", The EMBO J., vol. 11, No. 12, pp. 4747-4756 (1992).

Soto GE, et al., "Periplasmic Chaperone Recognition Motif of Subunits Mediates Quaternary Interactions in the Pilus", The EMBO J., vol. 17, No. 21, pp. 6155-6167 (1998).

Soto GE, et al., "Bacterial Adhesins: Common Themes and Variations in Architecture and Assembly", Journal of Bacteriology, vol. 181, No. 4, pp. 1059-1071 (1999).

Thanassi DG, et al., "The Chaperone/Usher Pathway: A Major Terminal Branch of the General Secretory Pathway", Curr. Opin. Microbiol., vol. 1, pp. 223-231 (1998).

Thanassi DG, et al., "The PapC Usher Forms an Oligomeric Channel: Implications for Pilus Biogenesis Across the Outer Membrane", Proc. Natl. Acad. Sci. USA, vol. 95, pp. 3146-3151 (1998).

Chapman, David A.G., et al., "Structural and Functional Significance of the FGL Sequence of the Periplasmic Chaperone Caf1M of *Yersinia pestis*", Journal of Bacteriology, vol. 181, No. 8, (Apr. 1999), pp. 2422-2429.

Flemmer, Katrina, et al., "Peptides Inhibit Complexation of the Bacterial Chaperone PapD and Reveal Potential to Block Assembly of Virulence Associated Pili", Bioorganic & Medicinal Chemistry Letters, vol. 5, No. 9, (1995), pp. 927-932.

Salit, I.E., et al., "TYPE I *Escherichia-coli* Pili Characterization of Binding to Monkey Kindey Cells", Journal of Experimental Medicine, vol. 146, No. 5, (1977), pp. 1182-1194.

Striker, Robert, et al., Stable Fiber-forming and Nonfiber-forming Chaperone-Subunit Complexes in Pilus Biogenesis, The Journal of Biological Chemistry, vol. 269, No. 16, (Apr. 22, 1994), pp. 12233-12239.

* cited by examiner

FIG. 3B ions and methods of use
ANTI-BACTERIAL COMPOUNDS DIRECTED AGAINST PILUS BIOGENESIS, ADHESION AND ACTIVITY; CO-CRYSTALS OF PILUS SUBUNITS AND METHODS OF USE THEREOF This application claims priority to co-pending U.S. provisional patent application Ser. No. 60/148,280, filed Aug. 11, 1999, incorporated herein by reference.

This invention was made in part with Government support under National Institutes of Health Grants RO1DK51406, RO1AI29549 and RO1GM54033. The Government has certain rights in the invention.

FIELD OF THE INVENTION

The present invention relates to compounds and methods for the treatment of diseases caused by tissue-adhering pilus-forming bacteria. More specifically, the invention relates to pharmaceutical preparations comprising substances capable of interfering with the binding of periplasmic chaperones to pilus subunits as well as pharmaceutical compounds capable of interfering with the binding between pilus subunits.

The present invention further relates to crystalline forms of pilus-subunit co-complexes, the high-resolution X-ray diffraction structures and atomic structure coordinates obtained therefrom. The pilus subunit co-crystals of the invention and the atomic structural information obtained therefrom are useful for solving structures of related proteins, and for screening for, identifying and/or designing compounds that bind periplasmic chaperones or pilus subunits and thus prevent the assembly and/or biological function of pili.

BACKGROUND OF THE INVENTION

Many pathogenic Gram-negative bacteria such as *Escherichia coli, Haemophilus influenzae, Salmonella enteriditis, Salmonella typhimurium, Bordetella pertussis, Yersinia enterocolitica, Yersinia perstis, Helicobacter pylori* and *Klebsiella pneumoniae* assemble hair-like adhesive organelles called pili on their surfaces. Pili are thought to mediate microbial attachment, often the essential first step in the development of disease, by binding to receptors present in host tissues and may also participate in bacterial—bacterial interactions important in biofilm formation.

Uropathogenic strains of *E. coli* express P and type 1 pili that bind to receptors present in uroepithelial cells. Adhesive P pili are virulence determinants associated with pyelonephritic strains of *E. coli* whereas type 1 appear to be more common in *E. coli* causing cystitis. The adhesin present at the tip of the pilus, PapG binds to the Gal (1–4)Gal moiety present in the glycolipids and glycoproteins, while the type 1 adhesin, FimH, binds D-mannose present in glycolipids and glycoproteins.

Type 1 pili are adhesive fibers expressed in *E. coli* as well as in most of the Enterobacteriaceae family. The type 1 pilus is a right handed helix with about 3 subunits per turn, a diameter of approximately 70 Å, a central pore of about 20–25 Å, and a rise per subunit of about 8 Å. See G. E. Soto et al., *EMBO J*, 17: 6155 (1998). Type 1 pili are composite structures in which a short tip fibrillar structure containing FimG and the FimH adhesin (and possibly the minor component FimF as well) are joined to a rod comprised predominantly of FimA subunits. See Jones et al., *Proc. Natl. Acad. Sci. U.S.A.*, 92: 2081 (1995). The FimH adhesin mediates binding to mannose-oligosaccharides. See S. N. Abraham et al., *Nature,* 336: 682 (1988); K. A. Krogfelt et al., *Infect. Immun.,* 58: 1995 (1990). In uropathogenic *E. coli*, this binding event has been shown to play a critical role in bladder colonization and disease.

Type 1 pilus biogenesis proceeds by way of a highly conserved chaperone/usher pathway that is involved in the assembly of over 25 adhesive organelles in the Gram-negative bacteria. See G. E. Soto and S. Hultgren, *J. Bacteriol.,* 181: 1059 (1999). The usher forms an oligomeric channel in the outer membrane with a pore size of approximately 2.5 nm and mediates subunit translocation across the outer membrane. See D. G. Thanassi et al., *Proc. Natl. Acad. U.S.A.,* 95: 3146 (1998).

P pili is a heteropolymeric surface fiber with an adhesive tip and consists of two major sub-assemblies, the pilus rod and the tip fibrillum. The pilus rod is a thick rigid rod made up of repeating PapA subunits arranged in a right-handed helical cylinder whereas the tip fibrillum is a thin, flexible tip fiber extending from the distal end of the pilus rod and is composed primarily of repeating PapE subunits arranged in an open helical configuration. Two components of the tip fibrillum, PapK and PapF, act as adaptors. PapK is thought to link the pilus rod to the base of the tip fibrillum and regulates the length of the tip fibrillum: its incorporation terminates its growth and nucleates the formation of the pilus rod. PapF is thought to join the PapG adhesin to the distal end of the flexible tip fibrillum.

The biogenesis of P pili also occurs via the highly conserved chaperone/usher pathway. See T. G. Thanassi et al., *Curr. Opin. Microbiol.,* 1: 223 (1998); D. L. Hung et al., *EMBO J,* 15: 3792 (1996). P pili are adhesive organelles encoded by eleven genes in the pap (pilus associated with pyelonephritis) gene cluster found on the chromosome of uropathogenic strains of *E. coli*. Six genes encode structural pilus subunits, PapA, PapH, PapK, PapE, PapF and PapG. See S. J. Hultgren et al., *Cell* 73: 887 (1993).

In P pili, two of the genes in the pap operon, papD and papC, encode the chaperone and usher, respectively. Chaperones such as PapD in *E. coli* are required to bind to pilus proteins imported into the periplasmic space, partition them into assembly component complexes and prevent non-productive aggregation of the subunits in the periplasm. See Kuehn M. J. et al., *Proc. Natl. Acad. Sci. USA* 88: 10586 (1991). PapD is a periplasmic chaperone that mediates the assembly of P pili. Detailed structural analysis has revealed that the PapD chaperone is the prototype member of a conserved family of periplasmic chaperones in Gram-negative bacteria. Periplasmic chaperones consist of two immunogloblin-like domains with a deep cleft between the two domains. See A. Holmgren and C. I. Branden, *Nature,* 342: 248 (1989); M. Pellecchia et al., *Nature Struct. Biol.,* 5: 885 (1998). Further, all members of the periplasmic chaperone superfamily have a conserved hydrophobic core that maintains the overall features of the two domains.

Periplasmic chaperones, along with outer membrane ushers, constitute a molecular mechanism necessary for guiding biogenesis of adhesive organelles in Gram-negative bacteria. These chaperones function to cap and partition interactive subunits imported into the periplasmic space into assembly competent co-complexes, making non-productive interactions unfavorable. The chaperone-subunit co-complexes are targeted to the outer membrane usher where subunits, or ushers, assemble in a specific order to form a pilus. During pilus biogenesis, PapD binds to and caps interactive surfaces on pilus subunits and prevents their premature aggregation in the periplasm. PapD binds to each of the pilus subunit types as they emerge from the cytoplasmic membrane and escorts them in assembly-competent, native-like conformations from the cytoplasmic membrane to outer membrane assembly sites comprised of PapC. PapC has been termed a molecular usher since it receives chaperone-subunit co-complexes and incorporates, or ushers, the subunits from the chaperone co-complex into the growing pilus in a defined order.

In the absence of an interaction with the chaperone, pilus subunits aggregate and are proteolytically degraded. Kolmer et al. and Jones et al. have shown that the DegP protease degrades pilus subunits in the absence of the chaperone. See *J. Bacteriol.* 178: 5925 (1996); *BIBO,* 16: 6394 (1997). This discovery led to the elucidation of the fate of pilus subunits expressed in the presence or absence of the chaperone using monospecific antisera in Western blots of cytosolic membrane, outer membrane and periplasmic proteins prepared according to methods known in the art.

Thus, prevention or inhibition of normal pilus assembly in Gram-negative bacterium impacts the pathogenicity of the bacterium by preventing the bacterium from attaching to and infecting host tissues. Moreover, changes in the binding between pilus subunits and chaperones can have a dramatic impact on the efficiency of pilus assembly, and thus on the ability of Gram-negative bacterium to adhere to and consequentially, infect host tissues. Prevention and inhibition of binding between pilus subunits and between pilus subunits and periplasmic chaperones have the effect of impairing pilus assembly, whereby the infectivity of the Gram-negative bacterium expressing the pili is reduced. Accordingly, a need exists, in general, for compositions and methods for preventing or inhibiting the normal interaction between pilus subunits and/or between a pilus subunit and a chaperone.

However, identification of such compositions has heretofore relied on serendipity and/or systematic screening of large numbers of natural and synthetic compounds. A far superior method of drug-screening relies on structure-based drug design. The three dimensional structures of proteins or protein fragments are determined and potential agonists and/or potential antagonists are designed with the aid of computer modeling. However, heretofore the three-dimensional structure illustrating the interaction between pilus subunits and/or between a pilus subunit and a chaperone has remained unknown, essentially because no such protein co-crystals had been produced which would permit the required X-ray crystallographic data to be obtained.

Therefore, there is presently a need for obtaining a co-crystal of a co-complex of a pilus and a chaperone to allow such crystallographic data to be obtained. Furthermore there is a need for the determination of the three-dimensional structure of such co-crystals. Finally, there is a need for procedures for related structural based drug design based on such crystallographic data.

SUMMARY OF THE INVENTION

Accordingly, the present invention provides antibacterial compositions and compounds capable of inhibiting or preventing pilus assembly in a Gram-negative bacterium. Such compounds interfere with the function of chaperones required for the assembly of pili from pilus subunits in diverse Gram-negative bacteria. Another object of the invention is to provide compounds having antibacterial activity that prevent or inhibit pili assembly by interfering with the interactions between pilus subunits. Yet another object of the invention is to provide compounds capable of inhibiting or preventing the function of pili adhesion to host epithelium thereby reducing the capacity of bacteria to attach to and infect host tissues. It is a further object of the invention to provide antibacterial compounds which have broad specificity for a diverse group of Gram-negative bacteria. Other objects include the provision of methods of preventing and inhibiting pilus assembly, methods of preventing or inhibiting pili adhesion to host tissues, methods of treating bacterial infections, methods for preventing and inhibiting biofilm formation and methods of preventing colonization by various Gram-negative bacterium.

Another aspect of the invention is to provide crystalline forms of polypeptides corresponding to a pilus chaperone-subunit protein co-complex. Thus, further objects of the present invention include the provision of the atomic structure coordinates obtained from the pilus chaperone-subunit co-crystals and methods of utilizing the three dimensional structural information obtained from the co-crystals to design or identify compounds with antibacterial activity. Another related object is to provide machine- or computer-readable media embedded with the three-dimensional structural information obtained from the pilus chaperone-subunit co-complex, or portions or subsets thereof which can be used to identify or design antibacterial compounds. A further object is to provide methods of making the co-crystals of the invention.

Therefore, in one aspect, the present invention is directed to isolated and purified compounds and synthesized compounds which bind to a pilus subunit groove and thus inhibit pilus assembly. Preferably, such compounds mimic the binding activity of the $G_1$ beta-strand of a periplasmic chaperone and comprise a polypeptide having an amino acid sequence containing at least two alternating hydrophobic amino acid residues. In a preferred embodiment, this polypeptide would be derived from a $G_1$ beta-strand of a periplasmic chaperone, more preferably, this polypeptide would be comprised of amino acids derived from the N101 to L107 amino acid region of a $G_1$ beta-strand of a periplasmic chaperone. A particularly preferred antibacterial compound which comprises a peptide comprising an amino-terminal amino acid sequence Asn-Val-Leu-Gln-Ile-Ala-Leu (SEQ ID NO: 1) or any related analogues that would competitively bind to the binding site of a pilus subunit.

In another embodiment, such compounds mimic the binding activity of the amino-terminal end of a pilus subunit and comprise a polypeptide having an amino acid sequence containing at least two alternating hydrophobic amino acid residues. Such antibacterial compounds will competitively bind to a binding site on pilus subunits, thereby inhibiting or preventing pilus assembly. A preferred polypeptide would be derived from the sequences of conserved amino-terminal motifs of pilus subunits. A particularly preferred antibacterial compound comprises a peptide comprising an amino-terminal amino acid sequence Ser-Asp-Val-Ala-Phe-Arg-Gly-Asn-Leu-Leu (SEQ ID NO: 12) or any related analogues that would competitively bind to the binding site of a pilus subunit.

A further object of the invention is to provide compounds which mimic mannose by binding to the amino-terminal end of the FimH adhesin. Such antibacterial compounds will bind to the mannose-binding site on pilus adhesins, thereby inhibiting or preventing the function of the pili to attach to and infect host tissues.

Interference with pili assembly and prevention of the capacity of pili to attach to host tissues are particularly effective since both the formation of pili and attachment of pili to host tissues are essential to bacterial pathogenicity. As such, the invention further provides compositions containing the above compounds in conjunction with a pharmaceutically-acceptable carrier, excipient or diluent. Also provided are methods of preventing or inhibiting pilus assembly in a Gram-negative bacterium by administering an effective amount of a compound capable of interfering with the binding of pilus subunits and all pilus subunit homologues. The invention is also directed to methods of preventing or inhibiting the pathogenicity of a Gram-negative bacterium comprising administering an effective amount of a compound capable of interfering with the adhesion of pili to host tissues. Further provided are methods for treating Gram-negative infections which comprise providing to a subject an effective amount of the above compounds and compositions.

Further, the present invention is directed to methods for preventing or inhibiting biofilm formation on a surface or in an environment containing Gram-negative bacteria. Also provided are methods for inhibiting bacterial colonization by a Gram-negative organism. These methods are accomplished by administering to such surfaces and environments an effective amount of a compound or a composition which is capable of interfering with pilus assembly or the ability of the pilus to adhere to and subsequently infect host tissues.

In another aspect, the invention provides compositions comprising crystalline forms of polypeptides corresponding to the PapD-PapK chaperone-pilus subunit protein co-complex. The PapD-PapK co-crystals comprise crystallized polypeptides corresponding to the wild-type or mutated PapD-PapK co-complexes. The PapD-PapK co-crystals preferably include native co-crystals, heavy-atom atom derivative co-crystals and co-crystals of a PapD-PapK co-complex that is further associated with one or more other molecules or compounds. Preferably, such other compounds bind to a site involved in protein—protein interactions in the pilus.

The PapD-PapK co-crystals are generally characterized by a spacegroup of $P2_12_12_1$, and a unit cell of a=62.1±0.2 Å, b=63.6±0.2 Å, c=92.7±0.2 Å, and are preferably of diffraction quality. In a preferred embodiment, the PapD-PapK co-crystals are of sufficient quality to permit the determination of the three-dimensional X-ray diffraction structure of the crystalline polypeptide co-complex to high resolution, preferably to a resolution of greater than about 3 Å, typically in the range of about 1 Å to about 3 Å.

The invention also provides methods of making the co-crystals of the invention. Generally, co-crystals of the invention are grown by dissolving substantially pure polypeptides in an aqueous buffer that includes a precipitant at a concentration just below that necessary to precipitate the polypeptide. Water is then removed by controlled evaporation to produce precipitating conditions, which are maintained until co-crystal growth ceases.

In another aspect, the invention provides machine- or computer-readable media embedded with the three-dimensional structural information obtained from the PapD-PapK co-crystals of the invention, or obtained from FimC-FimH co-crystals, or portions or subsets thereof. Such three-dimensional structural information will typically include the atomic structure coordinates of the crystallized polypeptide co-complex, or the atomic structure coordinates of a portion thereof, such as, for example, the atomic structure coordinates of one member of the co-complex or an active or binding site of one or both members, but may include other structural information, such as vector representations of the atomic structure coordinates, etc.

Thus, the atomic structure coordinates and machine readable media of the invention have a variety of uses. As such, provided are methods of identifying antibacterial compounds which utilize the coordinates for solving the three-dimensional X-ray diffraction and/or solution structures of other proteins, including mutant co-complexes, co-complexes further associated with other molecules, and unrelated proteins, to high resolution. Structural information may also be used in a variety of molecular modeling and computer-based screening applications to, for example, intelligently design mutants of the crystallized PapD-PapK or FimC-FimH co-complexes having altered biological activity and to computationally design and identify compounds that bind the polypeptide co-complexes or a portion or fragment of the polypeptide co-complexes, such as the mannose binding site of FimH and/or the $G_1$ beta strand binding cleft of PapK.

In another aspect, the present invention provides methods of using the coordinates of the PapD-PapK co-complex or of the FimC-FimH co-complex, or subsets of such structure coordinates, to design or identify candidate compounds capable of binding to a binding site on one member of the co-complex, or of a member of a related co-complex. Such candidate compounds may be evaluated for biological activity, such as, for example, the ability to bind (preferably competitively) the subunit of interest, the ability to disrupt chaperone-pilus subunit assembly and/or the ability to avoid adherence of a Gram-negative bacterium to a host tissue. In one embodiment, the co-crystals from which the PapD-PapK co-complex structure is derived have the space group and cell dimensions described above, such that the three dimensional structure of the co-complex is provided to a resolution of from about 3.0 Å to about 2.4 Å or greater. In another embodiment, the co-crystals from which the FimC-FimH co-complex structure is derived have the space group $P4_12_12$ or $P4_3$ with unit cell dimensions of a=b=97.7+/−0.2 Å and c=215.9+/−0.2 Å, such that the three dimensional structure of the co-complex can be determined to a resolution of from about 3.0 Å to about 2.5 Å or greater.

In a further aspect of the invention, such potential compounds are evaluated for biological activity. Candidate antibacterial compounds are designed or identified using the atomic structure coordinates of the PapD-PapK or FimC-FimH co-complexes or subsets thereof, synthesized and screened for their ability to bind to pilus subunits, thereby inhibiting or preventing pilus biogenesis. The antibacterial activity of the compound is determined by assaying the bacterium for infectivity or monitoring the pilus for activity. Alternatively, compounds designed or identified based upon their ability to bind the mannose binding domain of FimH are synthesized and screened for their ability to bind FimH. Such compounds that are able to prevent or inhibit pilus biogenesis or the ability of the bacterial pilus to attach to a host tissue can be used in the compositions of the present invention.

Other objects and features will be in part apparent and in part pointed out hereinafter.

BRIEF DESCRIPTION OF FIGURES

FIG. 3B is a depiction of the sequence alignment of P-pilus subunits (PapA (Seq. ID No: 57), PapK (Seq. ID No: 58), PapE (Seq. ID No: 59), and PapF (Seq. ID No: 60)). The secondary structural elements of PapK are indicated above the aligned sequences. Residue numbers of PapK are indicated above the PapK sequence. The remarkable conservation of structurally and functionally important residues strongly indicates that all pilins have structures similar to PapK.

ABBREVIATIONS AND DEFINITIONS

Figure 1A:
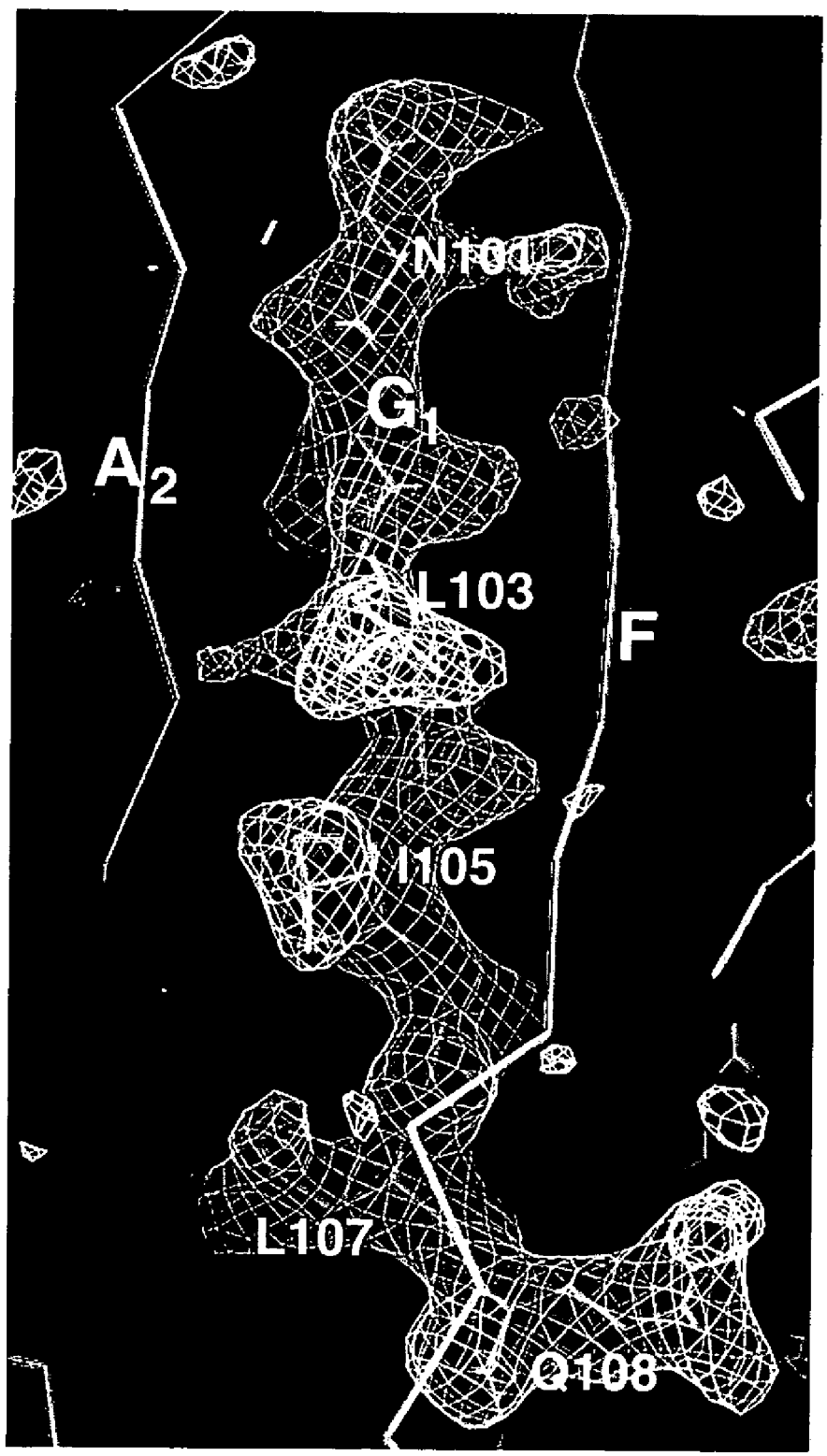
FIG. 1A is a depiction of representative regions of the electron density of a PapD $G_1$ beta-strand. Electron density is from a simulated annealing omit map calculated using the phases derived from the final model where the PapD $G_1$ beta-strand residues 101 to 108 have been omitted. Strands are labeled.

To facilitate understanding of the invention, a number of terms are defined below:

The amino acid notations used herein for the twenty genetically encoded L-amino acids are conventional and are abbreviated as follows:

| Amino Acid | One-Letter Symbol | Three-Letter Symbol |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

As used herein, unless specifically delineated otherwise, the three-letter and one-letter amino acid abbreviations designate amino acids in either the D-configuration or the L-configuration. For example, Arg designates D-arginine and L-arginine, and R designates D-arginine and L-arginine.

Unless noted otherwise, when polypeptide sequences are presented as a series of one-letter and/or three-letter abbreviations, the sequences are presented in the N→C direction, in accordance with common practice. As used herein, "C" refers to the alpha carbon of an amino acid residue.

For purposes of determining conservative amino acid substitutions in the various polypeptides described herein and for describing the various peptide and peptide analog compounds, the amino acids can be conveniently classified into two main categories—hydrophilic and hydrophobic—depending primarily on the physical-chemical characteristics of the amino acid side chain. These two main categories can be further classified into subcategories that more distinctly define the characteristics of the amino acid side chains. For example, the class of hydrophilic amino acids can be further subdivided into acidic, basic and polar amino acids. The class of hydrophobic amino acids can be further subdivided into apolar and aromatic amino acids. The definitions of the various categories of amino acids are as follows:

"Hydrophilic amino acid" refers to an amino acid exhibiting a hydrophobicity of less than zero according to the normalized consensus hydrophobicity scale of Eisenberg et al., 1984, J. Mol. Biol. 179:125–142. Genetically encoded hydrophilic amino acids include Thr (T), Ser (S), His (H), Glu (E), Asn (N), Gin (O), Asp (D), Lys (K) and Arg (R).

"Acidic amino acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic amino acid" refers to a hydrophilic amino acid having a side chain pK value of greater than 7. Basic amino acids typically have positively charged side chains at physiological pH due to association with hydronium ion. Genetically encoded basic amino acids include His (H), Arg (R) and Lys (K).

"Polar amino acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gin (O) Ser (S) and Thr (T).

"Hydrophobic amino acid" refers to an amino acid exhibiting a hydrophobicity of greater than zero according to the normalized consensus hydrophobicity scale of Eisenberg, 1984, J. Mol. Biol. 179:125–142. Genetically encoded hydrophobic amino acids include Pro (P), Ile (I), Phe (F), Val (V), Leu (L), Trp (W), Met (M), Ala (A), Gly (G) and Tyr (Y).

"Aromatic amino acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently ($C_1$–$C_6$) alkyl, substituted ($C_1$–$C_6$) alkyl, ($C_2$–$C_6$) alkenyl, substituted ($C_2$–$C_6$) alkenyl, ($C_2$–$C_6$) alkynyl, substituted ($C_2$–$C_6$) alkynyl, ($C_5$–$C_{20}$) aryl, substituted ($C_5$–$C_{20}$) aryl, ($C_6$–$C_{26}$) arylalkyl, substituted ($C_6$–$C_{26}$) arylalkyl, 5–20 membered heteroaryl, substituted 5–20 membered heteroaryl, 6–26 membered heteroarylalkyl or substituted 6–26 membered heteroarylalkyl. Genetically encoded aromatic amino acids include His (H), Phe (F), Tyr (Y) and Trp (W).

"Polar amino acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A).

"Aliphatic amino acid" refers to a hydrophobic amino acid having an aliphatic hydrocarbon side chain. Genetically encoded aliphatic amino acids include Ala (A), Val (V), Leu (L) and Ile (I).

"Hydroxyl-substituted aliphatic amino acid" refers to a hydrophilic polar amino acid having a hydroxyl-substituted side chain. Genetically-encoded hydroxyl-substituted aliphatic amino acids include Ser (S) and Thr (T).

The amino acid residue Cys (C) is unusual in that it can form disulfide bridges with other Cys (C) residues or other sulfanyl-containing amino acids. The ability of Cys (C) residues (and other amino acids with —SH containing side chains) to exist in a peptide in either the reduced free —SH or oxidized disulfide-bridged form affects whether Cys (C) residues contribute net hydrophobic or hydrophilic character to a peptide. While Cys (C) exhibits a hydrophobicity of 0.29 according to the normalized consensus scale of Eisenberg (Eisenberg, 1984, supra), it is to be understood that for purposes of the present invention Cys (C) is categorized as a polar hydrophilic amino acid, notwithstanding the general classifications defined above.

As will be appreciated by those of skill in the art, the above-defined categories are not mutually exclusive. Thus, amino acids having side chains exhibiting two or more physical-chemical properties can be included in multiple categories. For example, amino acid side chains having aromatic moieties that are further substituted with polar substituents, such as Tyr (Y), may exhibit both aromatic hydrophobic properties and polar or hydrophilic properties, and can therefore be included in both the aromatic and polar categories. As another example, His (H) has a side chain that falls within the aromatic and basic categories. The appropriate categorization of any amino acid will be apparent to those of skill in the art, especially in light of the detailed disclosure provided herein.

While the above-defined categories have been exemplified in terms of the genetically encoded amino acids, the amino acid substitutions need not be, and in certain embodiments preferably are not, restricted to the genetically encoded amino acids. Indeed, since many of the compounds described herein may be produced synthetically, they may comprise one or more genetically non-encoded amino acids. Thus, in addition to the naturally occurring genetically encoded amino acids, amino acid residues in the core peptides of structure (I) may be substituted with naturally occurring non-encoded amino acids and synthetic amino acids.

Certain commonly encountered amino acids of which the compounds of the invention may be comprised include, but are not limited to, β-alanine (β-Ala) and other omega-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); naphthylalanine (Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,3-diaminobutyric acid (Dab); p-aminophenylalanine (Phe(pNH$_2$)); N-methyl valine (MeVal); homocysteine (hCys), homophenylalanine (hPhe) and homoserine (hSer); hydroxyproline (Hyp), homoproline (hPro), N-methylated amino acids and peptoids (N-substituted glycines).

The classifications of the genetically encoded and common non-encoded amino acids according to the categories defined above are summarized in Table 1, below. It is to be understood that Table 1 is for illustrative purposes only and does not purport to be an exhaustive list of amino acid residues that can be used in the invention. Additional amino acids may be found in Fasman, 1989, *Practical Handbook of Biochemistry and Molecular Biology*, CRC Press, Inc., pp. 3–70, and the references cited therein.

TABLE 1

CLASSIFICATIONS OF COMMONLY ENCOUNTERED AMINO ACIDS

| Classification | Genetically Encoded | Non-Genetically Encoded |
| --- | --- | --- |
| Hydrophobic | | |
| Aromatic | H, F, Y, W | Phg, Nal, Thi, Tic, Phe(4-Cl), Phe(2-F), Phe(3-F), Phe(4-F), hPhe |
| Apolar | L, V, I, M, G, A, P | t-BuA, t-BuG, MeIle, Nle, MeVal, Cha, McGly, Aib |
| Aliphatic | A, V, L, I | b-Ala, Dpr, Aib, Aha, MeGly, t-BuA, t-BuG, MeIle, Cha, Nle, MeVal |
| Hydrophilic | | |
| Acidic | D, E | |
| Basic | H, K, R | Dpr, Orn, hArg, Phe(p-NH$_2$), Dbu, Dab |
| Polar | C, Q, N, S, T | Cit, AcLys, MSO, bAla, hSer |

As utilized herein, the term "pilus" or "pili" relates to fibrillar heteropolymeric structures embedded in the cell envelope of many tissue-adhering pathogenic bacteria, notably pathogenic gram negative bacteria. In the present specification, the terms pilus and pili will be used interchangeably. A pilus is composed of a number of "pilus subunits" which constitute distinct functional parts of the intact pilus.

The term "chaperone" relates to a molecule which in living cells has the responsibility of binding to polypeptides in order to mature the polypeptides in a number of ways. Many molecular chaperones are involved in the process of folding polypeptides into their native conformations whereas other molecular chaperones are involved in the export out of or import into the cell of polypeptides. Specialized molecular chaperones are "periplasmic chaperones" which are bacterial molecular chaperones exerting their main actions in the "periplasmic space." Specialized periplasmic chaperones also have an immunoglobulin-like three dimensional structure. The periplasmic space constitutes the space in between the inner and outer bacterial membrane. Periplasmic chaperones are involved in the process of correct assembly of intact pili structures. When used herein, the use of the term "chaperone" designates a molecular, periplasmic chaperone unless otherwise indicated.

The phrase "preventing or inhibiting binding between pilus subunits and a periplasmic chaperone" indicates that the normal interaction between a chaperone and its natural ligand, i.e., the pilus subunit, is being affected either by being inhibited, expressed in another manner, or reduced to such an extent that the binding of the pilus subunit to the chaperone is measurably lower than is the case when the chaperone is interacting with the pilus subunit at conditions which are substantially identical (with regard to pH, concentration of ions, and other molecules) to the native conditions in the periplasmic space. Measurement of the degree of binding can be determined in vitro by methods known to the person skilled in the art (microcalorimetry, radioimmunoassays, enzyme based immunoassays, etc.).

The phrase "preventing or inhibiting binding between pilus subunits" generally indicates that the normal interaction between pilus subunits is being affected either by being inhibited, expressed in another manner, or reduced to such an extent that the binding of a pilus subunit to another pilus subunit is measurably lower than is the case when the pilus subunits are interacting at conditions which are substantially identical (with regard to pH, concentration of ions, and other molecules) to the native conditions during pilus assembly. This phrase can apply to the dissociation of pre-formed pilus subunit—subunit interactions during pilus assembly. Measurement of the degree of binding can be determined in vitro by methods known to the person skilled in the art (microcalorimetry, radioimmunoassays, enzyme based immunoassays, etc.).

The compounds and compositions of the present invention which prevent or inhibit binding between pilus subunits or between a pilus chaperone or subunit are said to exhibit "antibacterial activity."

By the term "subject in need thereof" is in the present context meant a subject, which can be any plant or animal, including a human being, who is infected with, or is likely to be infected with, tissue-adhering pilus-forming bacteria which are believed to be pathogenic.

By the term "an effective amount" is meant an amount of the substance in question which will in a majority of patients have either the effect that the disease caused by the pathogenic bacteria is cured or ameliorated or, if the substance has been given prophylactically, the effect that the disease is prevented from manifesting itself. The term "an effective amount" also implies that the substance is given in an amount which only causes mild or no adverse effects in the subject to whom it has been administered, or that the adverse effects may be tolerated from a medical and pharmaceutical point of view in the light of the severity of the disease for which the substance has been given.

As used herein, "treatment" includes both prophylaxis and therapy. Thus, in treating a subject, the compounds of the invention may be administered to a subject already harboring a bacterial infection or in order to prevent such infection from occurring.

By the term "a mimic of a pilus subunit" is meant a compound which has been established to bind to a chaperone or to another pilus subunit in a manner which is comparable to the way the pilus subunit binds to the chaperone or to the way that the pilus subunits bind to each other, respectively.

The terms "an analogue of a $G_1$ beta-strand of a periplasmic chaperone" or "a mimic of a $G_1$ beta-strand of a periplasmic chaperone" denotes any substance which mimics or has the ability to bind to at least one pilus subunit in a manner which corresponds to the binding of a chaperone to a pilus subunit in the periplasmic space. Such an analogue or mimic of the chaperone can be a modified form of the intact chaperone (e.g. one of the two domains of PapD) or it can be a modified form of the chaperone which may e.g. be coupled to a probe, marker or another moiety. Another such analogue or mimic can be obtained by modifying or mutating the $G_1$ beta strand of the periplasmic chaperone so that it differs from the wild-type sequence by the substitution of at least one amino acid residue of the wild-type sequence with a different amino acid residue and/or by the addition and/or deletion of one or more amino acid residues to or from the wild-type sequence. The additions and/or deletions can be from an internal region of the wild-type sequence and/or at either or both of the N- or C-termini. In the present context, the pilus subunit, mimic or analogue thereof exhibits at least one binding characteristic relevant for the assembly of pili.

In the present context the terms "an analogue of a pilus subunit" and "a mimic of a pilus subunit" should be understood, in a broad sense, to mean any substance which mimics (with respect to binding characteristics) an effective part of a pilus subunit (e.g. the amino-terminal portion of the pilus subunit). Thus, the analogue or mimic may simply be any other compound regarded as capable of mimicking the binding between pilus subunits in vivo or in vitro. In the present context, the pilus subunit, mimic or analogue thereof exhibits at least one binding characteristic relevant for the assembly of pili.

In the present context the terms "a mannose analogue" or "a mannose mimic" should be understood, in a broad sense to mean any substance which mimics (with respect to binding characteristics) the mannose sugar which binds to an effective part of the FimH adhesin (e.g., the $NH_2$ terminal mannose-binding domain). Thus, the analogue or mimic may simply be any other compound regarded as capable of mimicking the binding of a mannose-oligosaccharide to FimH adhesin in vivo or in vitro. In the present context, the mannose analogue or mannose mimic exhibits at least one binding characteristic relevant for the adhesion of pili.

The term "donor stand complementation" refers to the mechanism by which a chaperone donates its $G_1$ beta-strand to complete the fold of a pilus subunit.

The term "donor strand exchange" refers to the mechanism by which the amino-terminal extension of a pilus subunit displaces the $G_1$ beta-strand of a pilus chaperone and subsequently occupies the subunit groove previously occupied by the $G_1$ beta-strand.

The term "crystallized PapD-PapK chaperone-subunit co-complex" refers to a polypeptide co-complex having an amino acid sequence as set out in SEQ ID NO: 1 and SEQ ID NO: 12 and which is in crystalline form.

The term "crystal" refers to a composition comprising a polypeptide in crystalline form. The term "crystal" includes native crystals, heavy-atom derivative crystals and co-crystals, as defined herein.

The term "native crystal" refers to a crystal wherein the polypeptide is substantially pure. As used herein, native crystals do not include crystals of polypeptides comprising amino acids that are modified with heavy atoms, such as crystals of selenomethionine mutants, selenocysteine mutants, etc.

The term "heavy-atom derivative crystal" refers to a crystal wherein the polypeptide is in association with one or more heavy-metal atoms. As used herein, heavy-atom derivative crystals include native crystals into which a heavy metal atom is soaked, as well as crystals of selenomethionine mutants and selenocysteine mutants.

The term "co-complex" refers to a polypeptide in association with one or more additional polypeptides or other molecules. For example, the PapD-PapK and FimC-FimH assemblies are co-complexes.

The term "co-crystal" refers to a composition comprising a co-complex, as defined above, in crystalline form. Co-crystals include native co-crystals and heavy-atom derivative co-crystals.

The term "unit cell" refers to the smallest and simplest volume element (i.e., parallelpiped-shaped block) of a crystal that is completely representative of the unit or pattern of the crystal. The dimensions of the unit cell are defined by six numbers: dimensions a, b and c and angles $\alpha$, $\beta$ and $\gamma$ (Blundel et al., 1976, Protein Crystallography, Academic Press.). A crystal is an efficiently packed array of many unit cells.

The phrase "having substantially the same three-dimensional structure" refers to a polypeptide that is characterized by a set of atomic structure coordinates that have a root mean square deviation (r.m.s.d.) of less than or equal to about 2 Å when superimposed onto the atomic structure coordinates of Tables 4 or 5 when at least about 50% to 100% of the $C_\alpha$ atoms of the coordinates are included in the superposition.

DETAILED DESCRIPTION OF THE INVENTION

In accordance with the present invention, applicants have designed and fabricated compounds which mimic components of chaperones such as PapD and pilus subunits such as PapK, and which thereby function to interfere with pilus assembly. Specifically, applicants have devised compounds and methods which interfere with the binding of a chaperone or a pilus subunit to a pilus subunit which will thus interfere with the formation of intact pili, thereby reducing the capacity of bacteria to adhere to host epithelium. Further, applicants have devised compounds which interfere with the adhesion of FimH adhesin to mannose oligosaccharides located on the host epithelium thereby reducing the capacity of piliated bacteria to attach to and infect host tissues. Applicants have further demonstrated that prevention or inhibition of pilus assembly in Gram-negative pathogens can be accomplished in a number of ways.

The co-crystal structure of PapD has been resolved and refined to a 2.0 angstrom resolution, revealing a molecule with two immunoglobulin-like domains oriented in an L shape to form a cleft at their interface. See A. Holmgren and C. E. Brenden, *Nature,* 342:248 (1989). The chaperone cleft contains surface-exposed residues that are highly conserved. Each immunoglobulin-like domain has a beta-barrel structure formed by two antiparallel beta-pleated sheets with an overall topology similar to an immunoglobulin fold. Applicants have resolved the co-crystal structure of the PapD-PapK chaperone-subunit co-complex which reveals how PapD stabilizes pilus subunits in the periplasm. Further, a combination of genetic, biochemical, and crystallographic data has demonstrated that the $G_1$ beta-strand of PapD forms a beta-zipper interaction with the highly conserved COOH-terminal motif of pilus subunits. See Hung, et al., *EMBO J.* 15:3792 (1996); Kuehn et al., *Science* 262:1234 (1993); Soto et al., *EMBO J.* 17:6155 (1998). This COOH-terminal motif also comprises at least part of a primary surface for subunit—subunit assembly interactions, indicating that the direct capping of a primary assembly surface is part of the molecular basis by which periplasmic chaperones prevent the premature oligomerization of pilus subunits. In addition, it is believed that the beta-zipper interaction facilitates the folding of the subunit into a native-like conformation via a template-mediated mechanism.

Applicants have solved the three dimensional co-crystal structure of a FimC-FimH chaperone-adhesin co-complex from uropathogenic *E. coli.* See Choudhury et al., *Science* 285: 1061 (1999). This molecular mechanism is supported by this structure. Specifically, applicants have demonstrated that in the FimC-FimH co-complex, the seventh ($G_1$) strand from the $NH_2$-terminal domain of the chaperone is used to complement the pilin domain between the second half of the A strand and the F strand of the domain. As such, the F strand of FimH forms a parallel beta-strand interaction with the $G_1$ beta-strand of FimC and has its COOH-terminal carboxyl group anchored in the crevice of the chaperone cleft of FimC.

Thus, applicants have elucidated the mechanism of binding between PapD and the pilus subunit PapK, thereby identifying an essential part of a defined binding site responsible for the binding between pilus subunits as well as binding between pilus subunits and their periplasmic chaperones. Furthermore, applicants have utilized the PapD-PapK co-crystal structure, the first of such a co-complex, and the FimC-FimH co-crystal structure to provide further insights into the processes of subunit folding, capping, and assembly in the chaperone/usher pathway of pilus biogenesis, and thereby devised compounds, compositions and methods for the prevention and inhibition of pilus formation.

Furthermore, applicants have elucidated the mannose binding domain of the FimH adhesin which is responsible for mediating the binding of pili to mannose receptors on host cells. As demonstrated further in the examples, a pocket capable of accommodating a mono-mannose unit is located at the tip of the lectin domain of the FimH adhesin. Applicants have utilized the identification of this mannose-binding site to design compounds and compositions which would function to interfere with pilus attachment to epithelial tissues thereby inhibiting or preventing the ability of the bacterium to infect host tissues.

PapD-PapK Chaperone-Subunit Co-Complex

An important aspect of the PapD-PapK chaperone-subunit co-complex is the structure of the PapK subunit. PapK has an immunoglobulin-like fold; however, it lacks the canonical seventh beta-strand and in its place is a deep groove located on the surface of the PapK subunit. The base of the groove on the surface of the PapK subunit is formed by the hydrophobic core of the protein. From the resolved co-crystal structure of the PapD-PapK chaperone-subunit co-complex, it can be seen that the $G_1$ beta-strand of the chaperone occupies this groove and prevents the exposure of the hydrophobic core of the subunit, which would lead to the destabilization and degradation of the subunits.

Moreover, the PapD-PapK chaperone-subunit co-complex provides further insight into the mechanism by which pilus subunits assemble to form a mature, intact pilus. The eight amino acids located on the amino-terminus of PapK are disordered and presumably project away from the co-complex. These residues contain a pattern of alternating hydrophobic residues typical of a beta-strand which is conserved in pilus subunits. Thus, while not being bound to a particular theory, it is believed that in the mature pilus, the amino-terminal residues of one subunit occupy the groove of the adjacent subunit.

In the PapD-PapK co-complex structure, strand F of PapK forms one side of the groove into which the $G_1$ beta-strand of the chaperone is inserted and is likely to assume the same structural role in pilins. Structural, biochemical and genetic data have demonstrated that strand F (and hence the groove) in pilins is involved in both chaperone-subunit and subunit—subunit interactions. By donating a secondary structural element to the fold of the pilin, the chaperone not only contributes to the stability of the pilin but also prevents other pilins in the periplasm from binding to the groove of the chaperone-bound subunit.

The amino-terminal region of pilins, corresponding to the disordered amino-terminus of PapK, has also been shown to form an assembly surface on the pilin. The eight $NH_2$-terminal residues are disordered in the PapD-PapK co-complex and protrude away from the main body of the co-crystal structure where they would be free to interact with the groove of the preceding subunit located at the usher. The amino-terminus of an incoming subunit inserts into the groove of the preceding subunit, displacing the $G_1$ beta-strand of the chaperone in a mechanism that is facilitated by the usher. Applicants refer to this mechanism as "donor strand exchange". Donor strand exchange implies that in the pilus, the $NH_2$-terminal strand of one subunit would complete the immunoglobulin-like fold and protect the hydrophobic core of the preceding subunit, much as the chaperone does in the periplasm.

A donor strand exchange model for pilus assembly employing a PapK structure was utilized to model a PapA pilus rod. Pilus rods are well-ordered helical structures with a diameter of 68 Å, a pitch of 24.9 Å, and 3.28 subunits per turn. The disordered $NH_2$-terminus of PapK was modeled as a beta-strand protruding from the Ig fold at an angle consistent with the ordered portion of the $NH_2$-terminus in the structure, and inserted into the groove of the preceding subunit. A pilus rod with the appropriate general features and without steric clashes could be built by applying identical translational and rotational operations to successive subunits. The model pilus has a 72 Å diameter, a pitch of approximately 22 Å, and approximately 3.3 subunits per turn, similar to the actual dimensions of the pilus rod (FIG. 7). However, the model has an unexpected feature: the NH2-terminal strand of one subunit runs antiparallel (not parallel as does the $G_1$ beta-strand of PapD) to strand F of the preceding subunit. A parallel beta-strand interaction with strand F of the preceding subunit would produce a rod with a star-shaped cross-section (FIGS. 7A and 7B), inconsistent with the electron microscopy data. Thus, while donor strand complementation with the chaperone results in an atypical immunoglobulin fold, donor strand exchange between subunits produces a canonical variable-region immunoglobulin fold in the mature pilus.

FimC-FimH chaperone-adhesin co-complex

Further evidence illustrating donor strand complementation is provided by the resolution of the co-crystal structure of the FimC-FimH chaperone-adhesin co-complex from uropathogenic *E. coli*. See Choudhury, et al., *Science* 285: 1061 (1999). The FimC-FimH chaperone-adhesin co-complex structure also reveals a donor strand complementation mechanism that explains the basis of both chaperone function and pilus biogenesis.

Figure 8A:
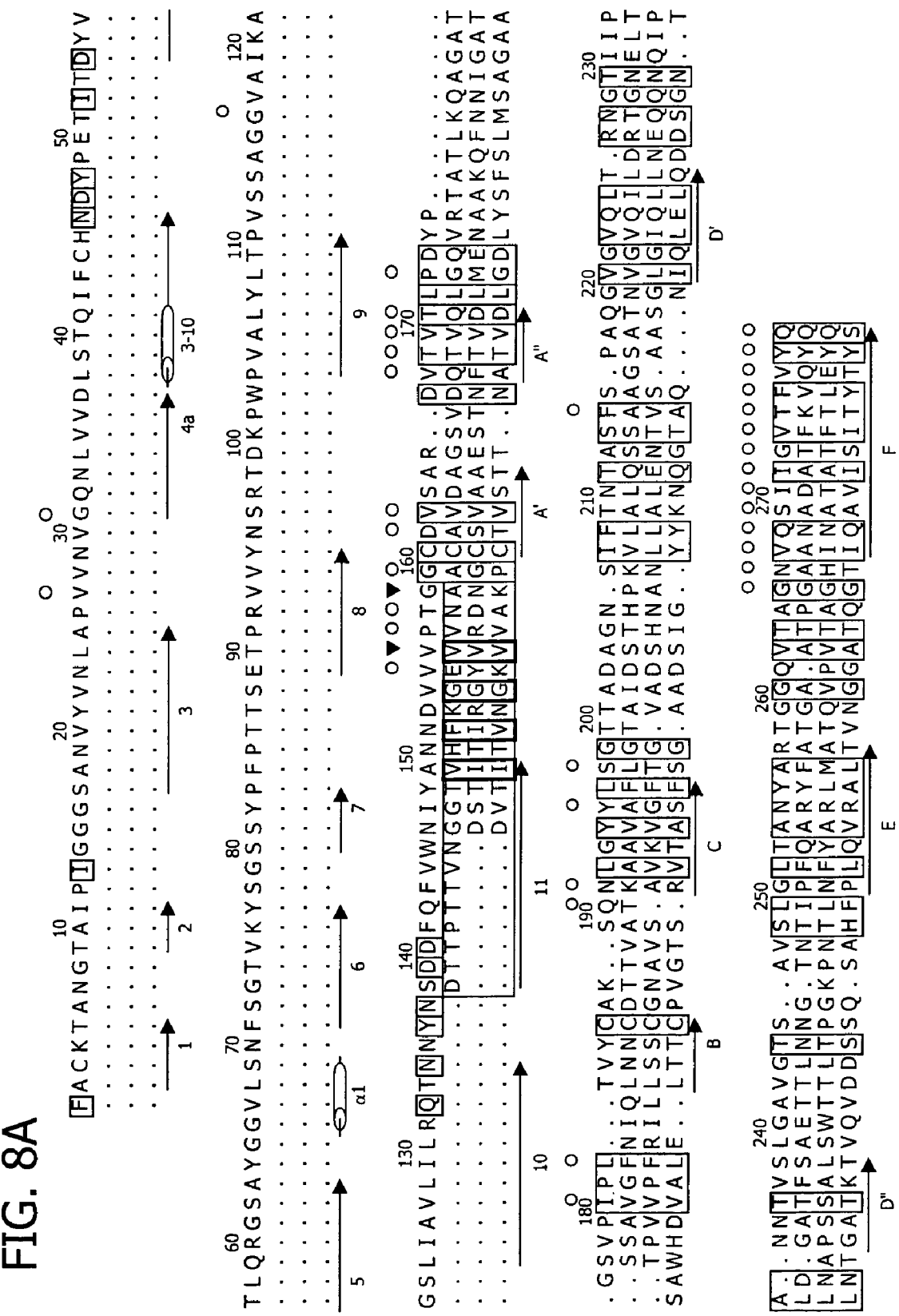
FIG. 8A depict the amino acid sequences of type 1 pilus subunits (FimA (Seq. ID No: 62), FimF (Seq. ID No: 63), FimG (Seq. ID No: 64), FimH (Seq. ID No: 65)). The end of the mannose binding lectin domain and the start of the pilin domain in FimH are indicated by vertical arrows above the sequences. Type 1 pilin subunits (FimA, FimF, FimG) were aligned with the pilin domain of FimH using Clustal W and manually adjusted to minimize gaps in secondary structure elements. Gaps in the alignment are indicated by dots. Sequence numbering for FimH starts at position 22 in the pre-protein. Residues involved in chaperone binding are indicated by an open circle above the residue. Residues in the carbohydrate binding pocket are boxed. A large box marks the $NH_2$-terminal extensions in the pilin subunits. The conserved b-zipper motif found in all pilin subunits corresponds to the F beta-strand. Limits and nomenclature for secondary structure elements are shown below the sequence.

The FimH adhesin subunit is folded into two domains of the all-beta class, a $NH_2$-terminal mannose-binding domain and a COOH-terminal pilin domain. A short extended linker (residues 157H–159H) connects the two domains. The $NH_2$-terminal mannose-binding domain comprises residues 1H–156H, and the COOH-terminal pilin domain which is used to anchor the adhesin to the pilus comprises residues 160H–279H (FIG. 8A). The pilin domain of FimH binds in the cleft of the chaperone (FIG. 9B) with limited contact between FimH and the COOH-terminal domain of FimC.

Figure 8B:
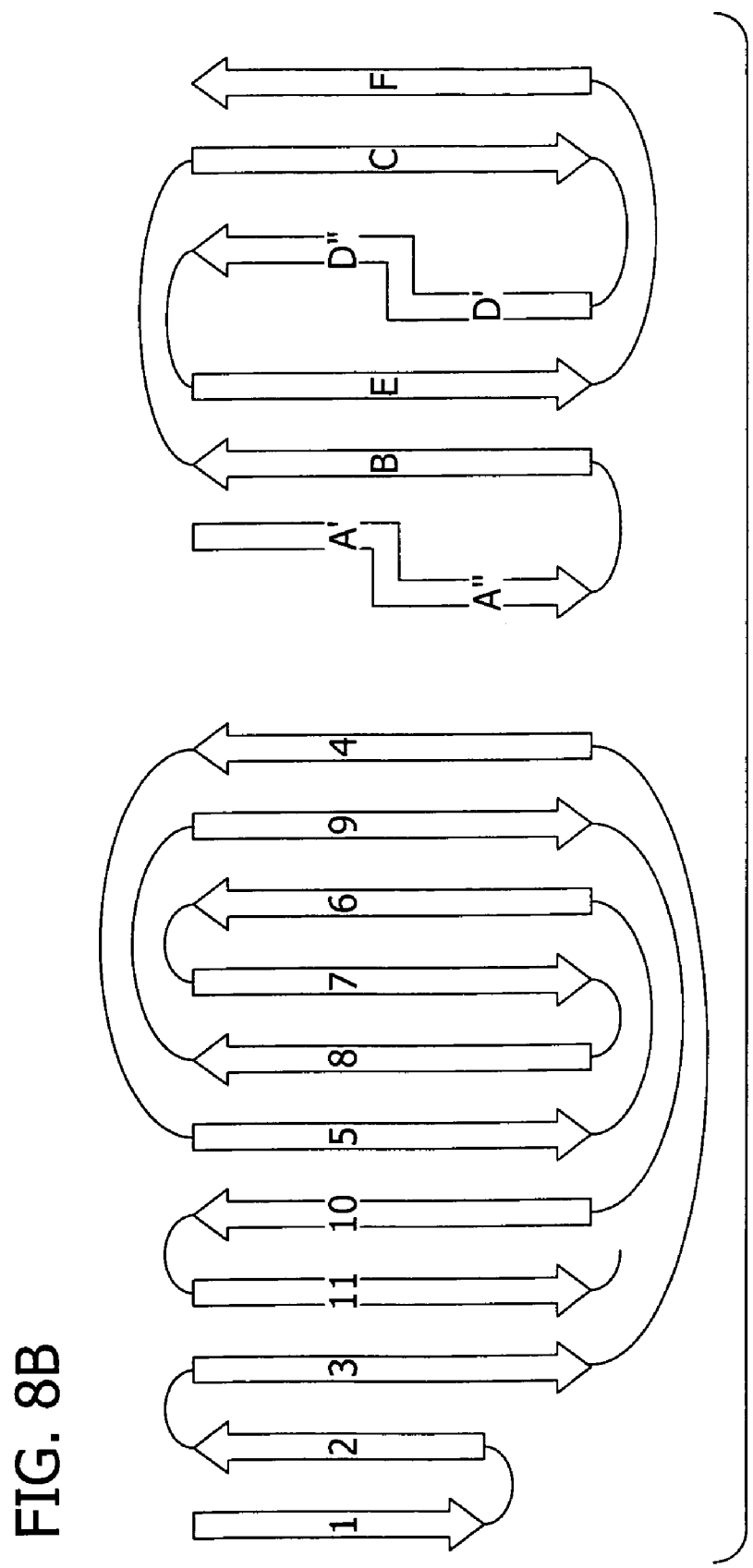
FIG. 8B are beta-sheet topology diagrams of the mannose binding domain (left) and pilin domain (right) of FimH.
Figure 9A:
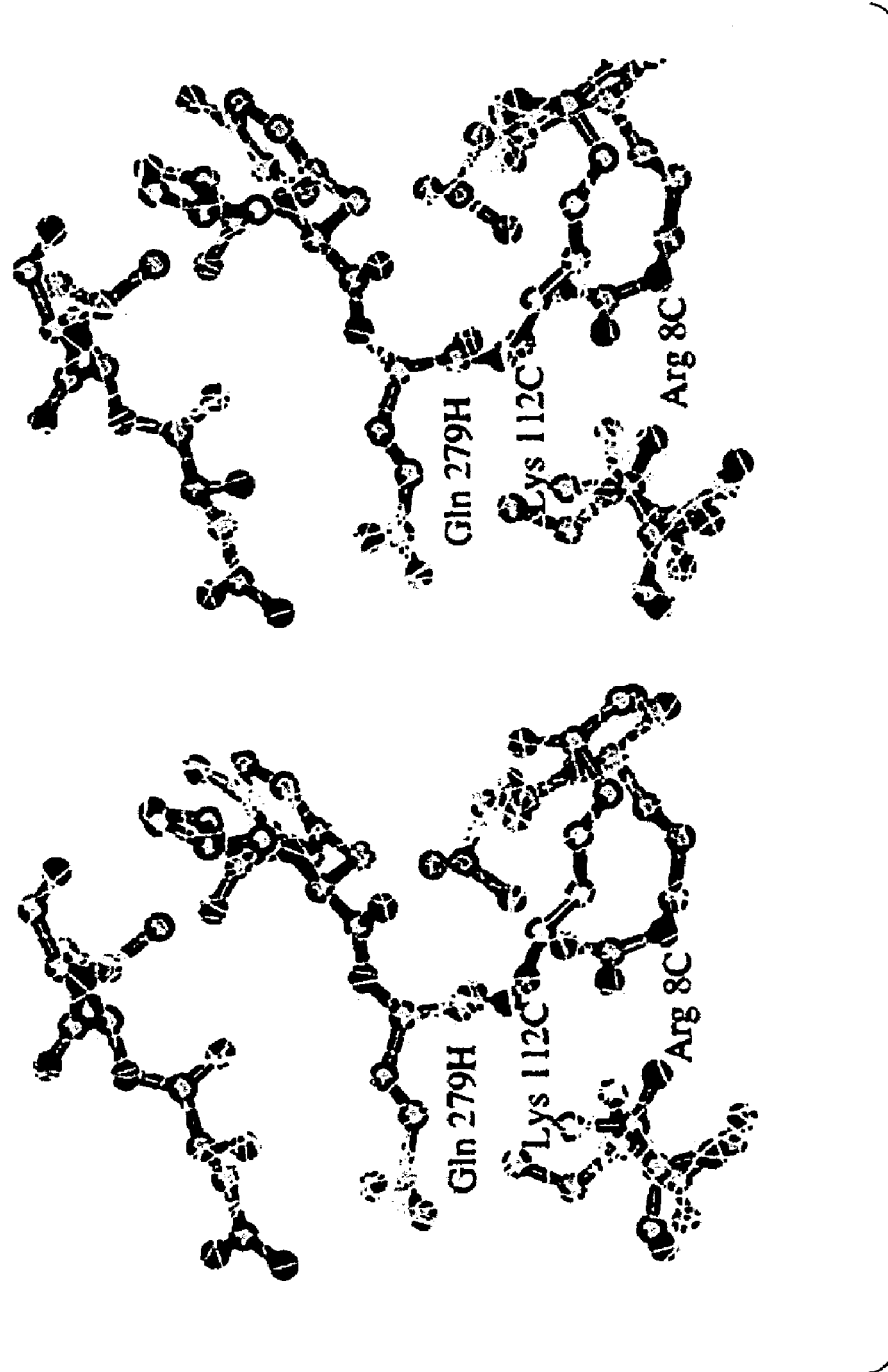
FIG. 9A is a typical sample of the solvent flattened experimental electron density map (contoured at 1.0σ) with the refined model superimposed. $Arg^{8C}$ and $Lys^{112C}$ anchor the COOH-terminus of FimH in the subunit binding cleft of the chaperone via hydrogen bonds to the terminal carboxylate.
Figure 9B:
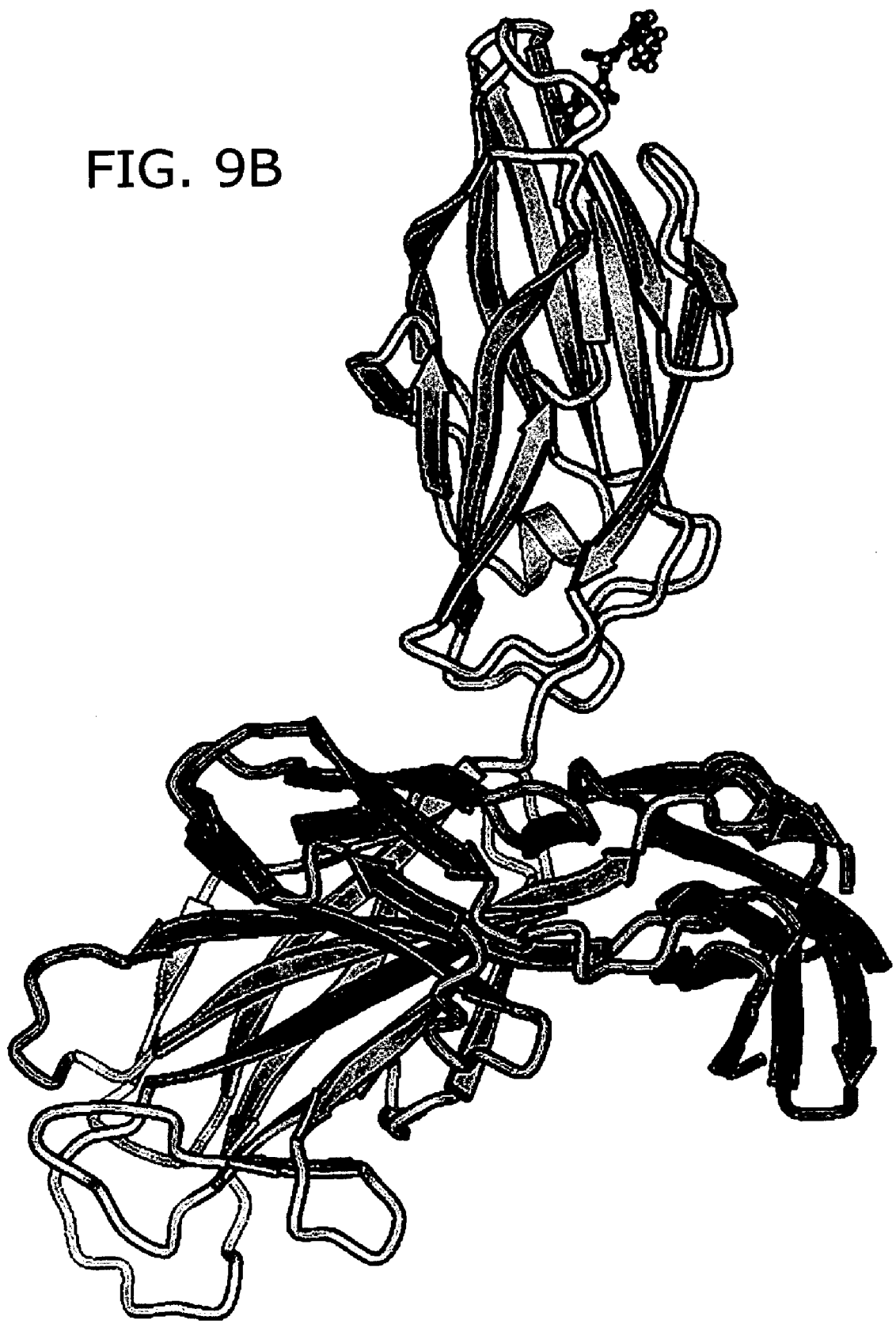
FIG. 9B is a MOLSCRIPT ribbon diagram of the FimC-FimH co-complex. A ball-and-stick representation of the C-HEGA molecule bound to the lectin domain of FimH indicates the position of the carbohydrate-binding site at the tip of the domain.
Figure 10A:
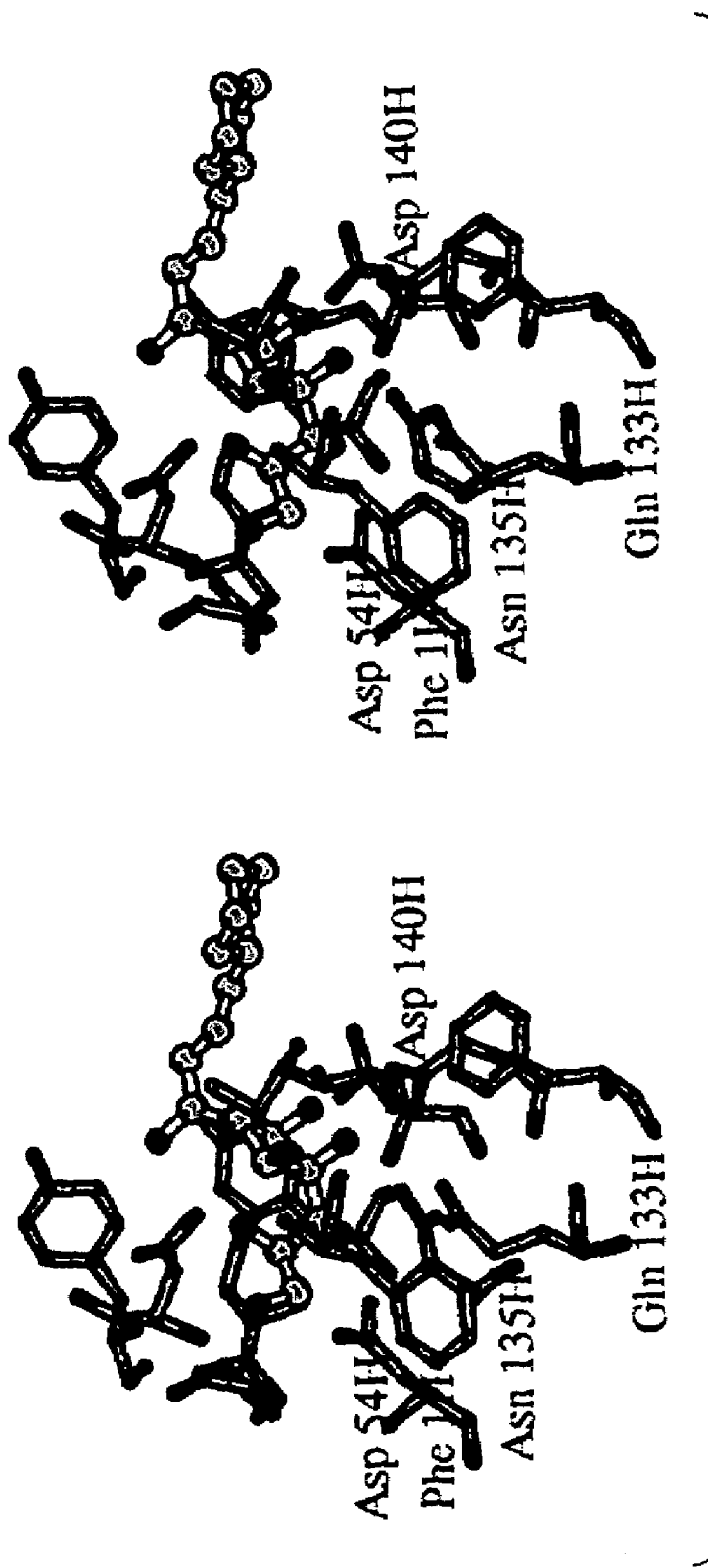
FIG. 10A is a depiction of FimH carbohydrate binding. A stereo view of the carbohydrate binding pocket with a molecule of C-HEGA bound. Residues $Phe^{1H}$, $Ile^{13H}$, $Asn^{46H}$, $Asp^{47H}$, $Tyr^{48H}$, $Ile^{52H}$, $Asp^{54H}$, $Gln^{133H}$, $Asn^{135H}$, $Tyr^{137H}$, $Asn^{138H}$, $Asp^{140H}$, $Phe^{142H}$ line the surface of the pocket at the tip of the lectin domain is shown. Residues that take part in hydrogen bonding to the glucamide moiety of C-HEGA are labeled.

The lectin domain of FimH is an eleven-stranded elongated beta-barrel with a jelly roll-like topology (FIG. 8B). The fold starts with a short beta hairpin that it not part of the jelly roll. The final (eleventh) strand of the domain is inserted between the third and tenth strands and thus breaks the jelly-roll topology. A pocket capable of accommodating a mono-mannose unit is located at the tip of the domain, distal from the connection to the pilin domain (FIG. 9B). The bottom of the pocket is lined with asparagine, glutamine and aspartic acid residues in three loop regions which are typical carbohydrate binding side chains (FIG. 10A). These residues form hydrogen bonds with C-HEGA as described in Example 3 herein.

Figure 10B:
FIG. 10B is a depiction of the surface of the FimH pilin domain showing the exposed hydrophobic core. Hydrophobic residues that are in contact with FimC in the co-complex but solvent exposed upon removal of the chaperone are highlighted in yellow. Right: as left but with FimC ribbon in blue. The seventh G1 strand of FimC donates hydrophobic residues to complement the incomplete hydrophobic core of the pilin domain.

The pilin domain of FimH has the same immunoglobulin-like topology as the amino-terminal domain of FimC, except that the seventh strand of the fold is missing (FIG. 8B). Two anti-parallel beta-sheets (strands A'BED' and D"CF) pack against each other to form a beta-barrel that is similar to, but distinct from, immunoglobulin barrels. As in the chaperones, strand switching occurs at the edges of the sheets. In the chaperones, the A1 strand of the amino-terminal domain switches between the two sheets of the barrel. The first strand of the pilin domain exhibits a similar switch, but due to the lack of a seventh strand, the second half of the A strand is not involved in main chain hydrogen bonding within the domain. The D strand of the chaperones as well as of the FimH pilin domain also switches, but in the pilin domain the switch is an eight-residue loop instead of the cis-proline bulge found in the chaperones. The C–D loop and the D'–D" connection pack against each other and close the top of the barrel. The other side of the barrel, defined by the A and F edge strands, is open. Due to the absence of a seventh strand a deep scar is created on the surface of the domain. Residues that would be part of the hydrophobic core of an intact, seven stranded PapD-like domain instead line a deep hydrophobic crevice on the surface of the pilin domain (FIG. 10B).

Figure 10C:
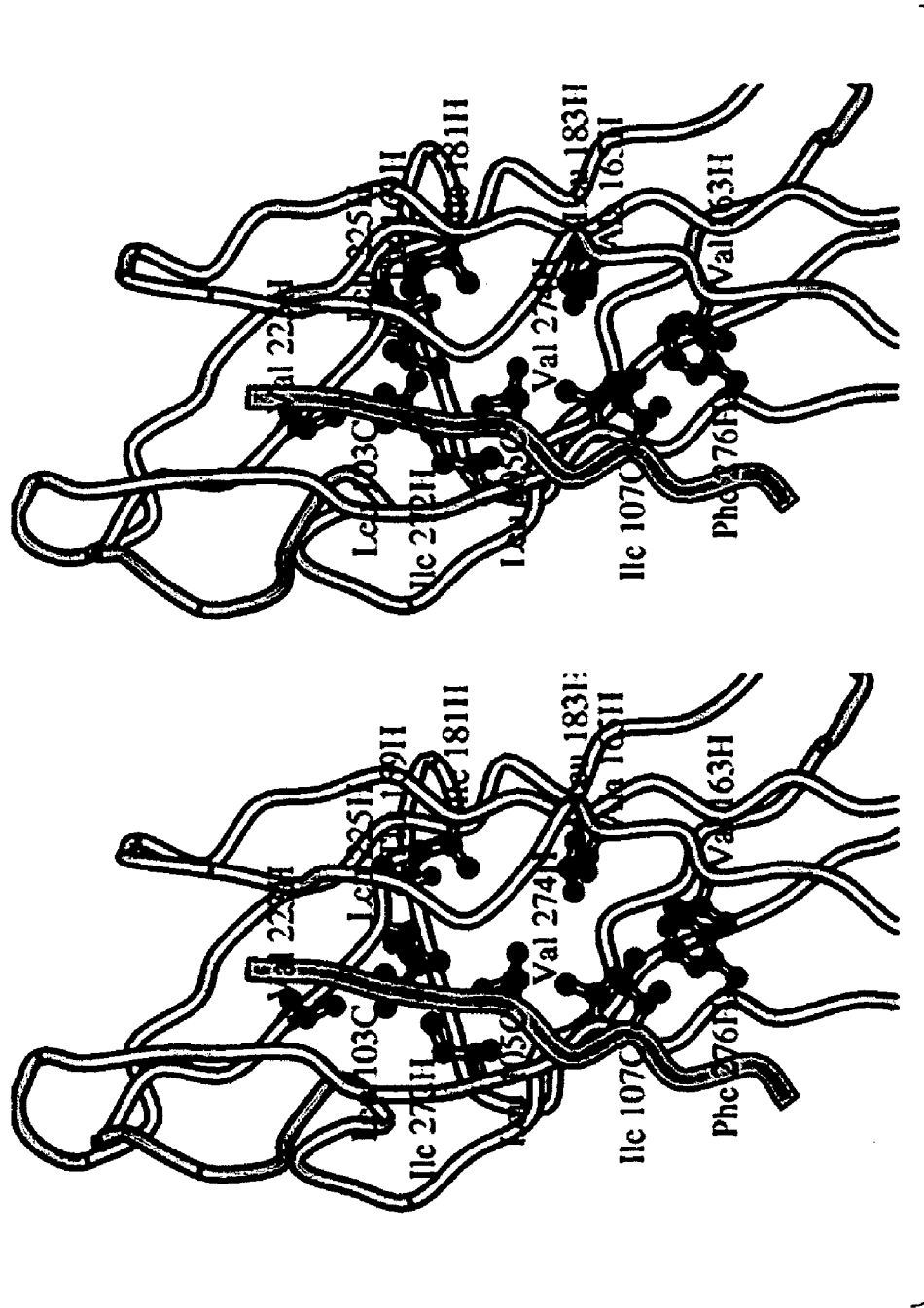
FIG. 10C is a close-up of donor strand complementation interactions. Hydrophobic residues on the surface of the pilin domain (Val$^{163H}$, Ala$^{165H}$, Thr$^{169H}$, Ile$^{181H}$, Leu$^{183H}$, Val$^{223H}$, Leu$^{225H}$, Ile$^{272H}$, Val$^{274H}$, and Phe$^{276H}$) and FimC residues involved in donor strand complementation (Leu$^{103C}$, Leu$^{105C}$, Ile$^{107C}$, Ser$^{109C}$, Ile$^{111C}$) pack against each other to form a complete hydrophobic core extending between the two proteins.

As mentioned herein, the donor strand complementation mechanism refers to the chaperone donating its $G_1$ beta-strand to complete the fold of the pilin domain. The $G_1$ beta-strand of periplasmic chaperones such as FimC and PapD contains a conserved motif of solvent-exposed hydrophobic residues at positions 103, 105 and 107. In the chaperone-subunit co-complex, the $G_1$ beta-strand containing these alternating hydrophobic residues are used to complete the unfinished hydrophobic core of pilus subunits such as FimH and PapD. Thus, in the FimC-FimH co-complex, these hydrophobic residues are used to complete the unfinished hydrophobic core of FimH which results from the missing seventh strand. Specifically, the seventh ($G_1$) strand from the $NH_2$-terminal domain of the FimC chaperone complements the FimH pilin domain by being inserted between the second half of the A strand and the F strand of the domain (FIG. 10C). $Leu^{103C}$ and $Leu^{105C}$ are deeply buried in the crevice in the FimH pilin domain. $Leu^{103C}$ of FimC contacts residues $Ile^{181H}$, $Val^{223H}$, $Leu^{225H}$ and $Ile^{272H}$ of FimH. $Leu_{105C}$ of FimC is in contact with $Ile^{181H}$, $Leu^{252H}$, $Ile^{272H}$, and $Val^{274H}$ of FimH. $Ile^{107}$ is closer to the FimH pilin domain surface but mades van der Waals contacts with residues $Val^{163H}$ and $Phe^{276H}$. The final strand (F) of FimH forms a parallel beta-strand interaction with the $G_1$ beta-strand of FimC and has its COOH-terminal carboxylate group anchored in the crevice of the chaperone cleft through hydrogen bonding with the conserved residues $Arg^{8C}$ and $Lys^{112C}$ in FimC (FIG. 9A). This interaction is critical for chaperone function.

Furthermore, the two conserved motifs of FimH (the COOH-terminal F strand and an amino-terminal motif) participate in subunit—subunit interactions necessary for pilus assembly. See G. E. Soto et al., *EMBO J*, 17: 6155 (1998). An alignment of the pilin sequences demonstrates that the amino-terminal motif of FimC was part of a 10–20 residue $NH_2$-terminal extension that was missing in the FimH pilin domain (FIG. 8A) and disordered in the PapD-PapK co-complex as discussed above. This region contains a highly conserved pattern of alternating hydrophobic residues (highlighted in FIG. 8A) similar to the donor $G_1$ beta-strand of the chaperone. Applicants believe that the amino-terminal extension of the FimH subunit is structurally analogous to the donor $G_1$ beta-strand motif of the chaperone and thus, would fit into the pilin groove occupied by the donor $G_1$ beta-strand of the chaperone.

However, the type 1 pilus is a right handed helix with about 3 subunits per turn, a diameter of approximately 70 Å, a central pore of about 20–25 Å, and a rise per subunit of about 8 Å. Thus, in order to obtain this structure, the insertion of the $NH_2$-terminal extension must be antiparallel to strand F in contrast to the parallel insertion observed for the $G_1$ beta-strand of the chaperone. Insertion in a parallel orientation would lead to rosette-like structures. One edge of the pilin groove is lined by the COOH-terminal F strand and forms a critical part of the subunit tail. Thus, without being bound to any theory, Applicants believe that the amino-terminal extension represents the head of a subunit and during pilus biogenesis, the amino-terminal extension would displace the donor $G_1$ beta-strand of the chaperone to fit into the tail groove of a neighboring subunit to complete the pilin fold of its neighbor in a donor strand complementation mechanism.

Figure 11A:
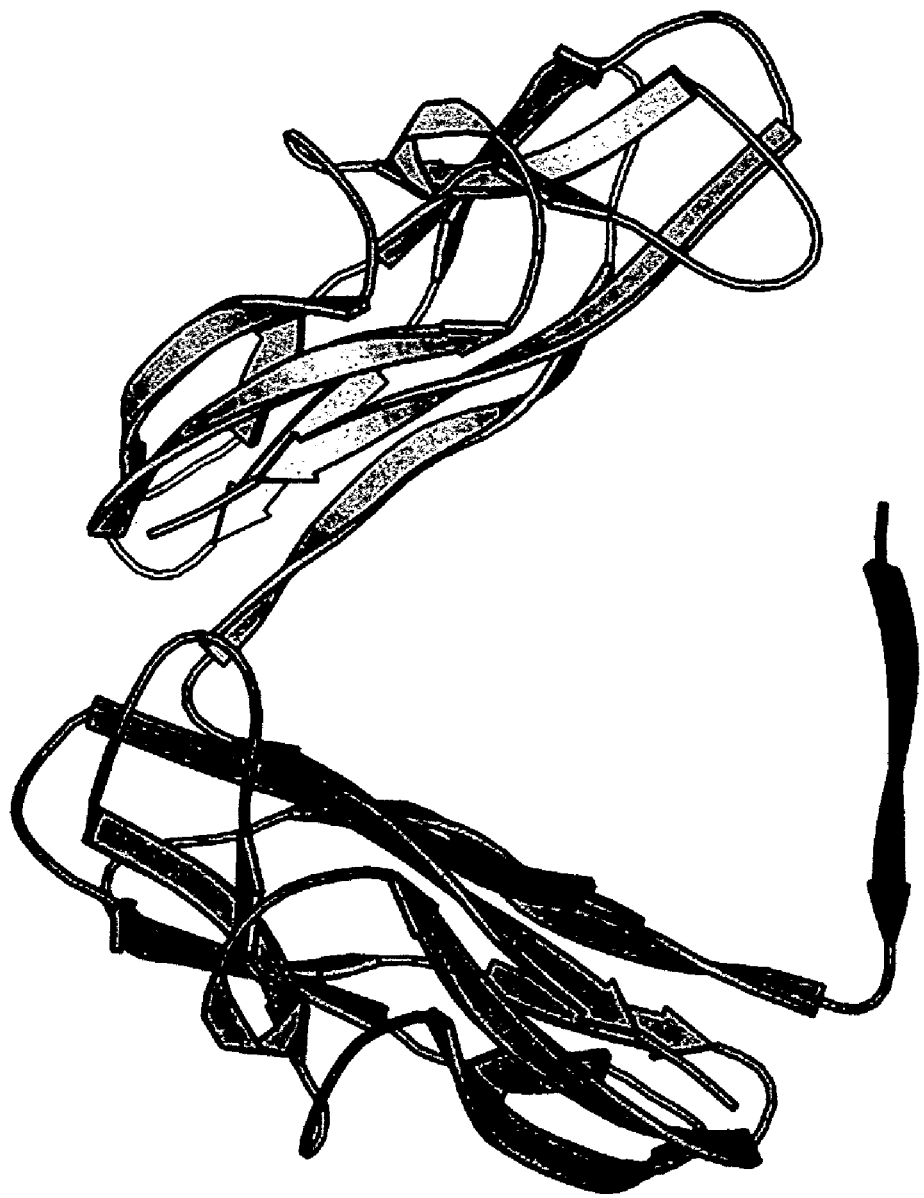
FIG. 11A is a model of the type 1 pilus.
Figure 11B:
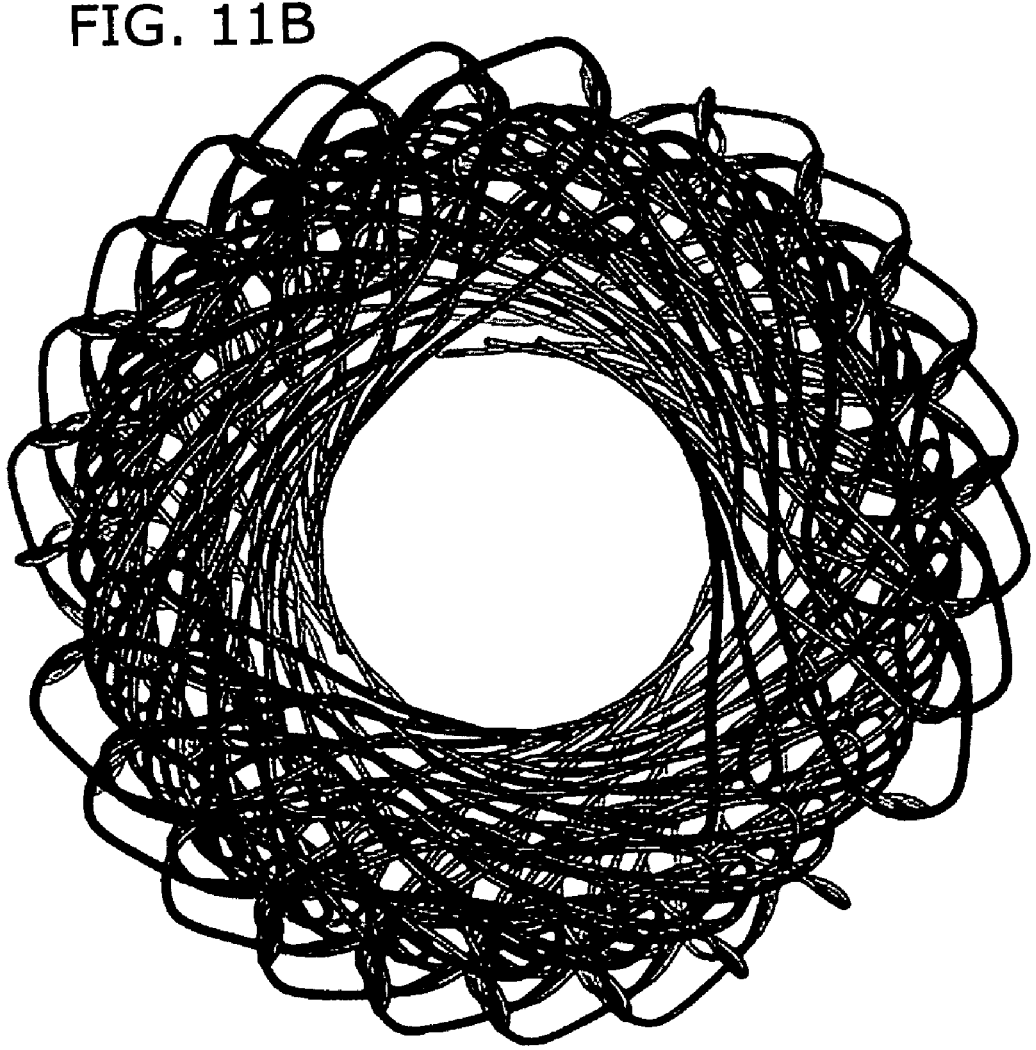
FIG. 11B is a top view of the type 1 pilus. Residue positions that are subject to allelic variation map to the outer surface of the pilus.
Figure 11C:
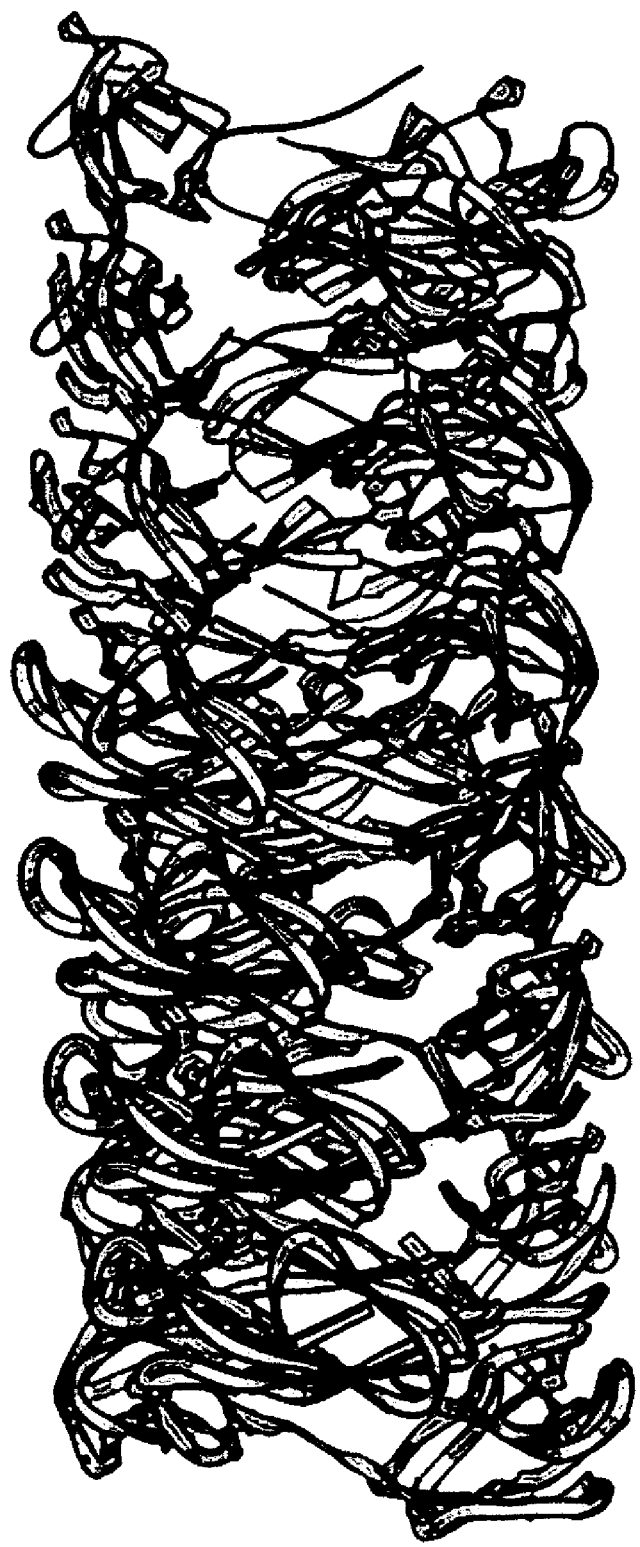
FIG. 11C is a side view of the type 1 pilus.

Applicants constructed a model for the type 1 pilus using the FimH pilin domain as a model for FimA (FIG. 11). Each subunit was aligned to have its cleft facing towards the center of the pilus so that the height from the top to the bottom of the domain along the helix axis was approximately 25 Å. Applying a rotation of 115 degrees and a rise per subunit of 8 Å, a hollow helical cylinder is created. The outer diameter of this cylinder as measured across $C_\alpha$ atoms is 70 Å, and the inner diameter is 25 Å. FimA subunits from different strains of *E. coli* exhibit considerable allelic variation. The vast majority of the variable positions are on the outside surface of the pilus model described above (FIG. 11) which would account for the antigenic variability of type 1 pili.

The head-to-tail interaction between subunits in a pilus is reminiscent of oligomerization through three dimensional domain swapping in the sense that a part of the molecule is used to complement another. However, in this case, complementation occurs not only between identical protein chains (FimA in the pilus rod) but also between homologous but distinct chains e.g., FimG, FimF and FimH in the pilus tip. Furthermore, because individual pilins promoters do not exist as stable monomers, there is no exchange of structural units between a monomeric and an oligomeric state. Instead, a different protein, the periplasmic chaperone, is needed to keep the monomeric subunits in solution by donating a unique part of its structure (the $G_1$ beta-strand) to the different subunit grooves.

Based on the structure of the FimC-FimH co-complex and without being limited to any theory, it is believed that pilins are missing necessary steric information needed to fold into a native three dimensional structure. The information that is missing consists of the seventh edge strand of an immunoglobulin fold. This strand, which is necessary for folding, is donated to the hydrophobic core of the pilin by the periplasmic chaperone in a donor strand complementation mechanism.

Applicants further utilized the co-crystal structure of the FimC-FimH chaperone-adhesin co-complex to identify the amino-terminal mannose-binding domain of FimH, an essential component required for pilus adhesion to host tissues. As discussed above, the bottom of this mannose-binding domain is lined with asparagine, glutamine and aspartic acid residues and those skilled in the art would be able to use molecular modeling techniques and other existing protocols to design and synthesize antibacterial compounds. Such compounds would compete with mannose for binding to the FimH adhesin thereby preventing or inhibiting pilus adhesion to host epithelium.

Thus, applicants utilized the discovery of this molecular mechanism of protein binding to identify an essential part of a defined binding site responsible for pilus assembly and adhesion. Further, applicants have utilized this structure to design and fabricate methods and compounds to compete with the chaperone for binding to the exposed binding site of the pilus subunit thereby inhibiting pilus assembly and reducing the pathogenicity of piliated Gram-negative bacterium. Such a compound is useful in treating bacterial diseases or in preventing costly biofilm formation in medical, industrial and various other settings.

Peptide Compounds

Thus, the present invention is directed to compounds which mimic the capability of a periplasmic chaperone or of a pilus subunit to bind to the groove of a pilus subunit, thereby preventing or inhibiting pilus biogenesis by interfering with the normal function of these biological components. Specifically, applicants have shown that prevention or inhibition of the binding between pilus subunits and between pilus subunits and periplasmic chaperones can be accomplished in a number of ways.

In a preferred embodiment of the invention, the compounds are peptides or peptide analogs that are capable of disrupting the assembly of pilus subunits and/or binding the cleft of a pilus subunit that is bound by the $G_1$ beta-strand of another pilus subunit in an assembled pili structure and comprise a core sequence of residues preferably derived from a conserved N-terminal region of a pilus subunit. As will be apparent from alignments of the conserved N-terminal regions of the various pilus subunits, such peptides and peptide analogs will typically comprise at least two alternating hydrophobic amino acids. The core sequence of such peptides and peptide analogs may be derived from the amino-terminal sequence of any of a number of pilus subunits, including but not limited to, PapA, PrsA, FimA, AfaA, FocA, HifA, HafA, Fim2, Fim3, MrpA, PmfA, LpfA, PefA, ArfA, PapK, PrsK, PapH, PrsH, PapE, PrsE, MrpB, SfaG, SfaS, FocG, FocF, PapF, PrsF, MprF, MrpE, F17A, FanC, FaeA, MrkA and RalC. Typically, the core sequence is composed of about 3 to about 12 residues, preferably 5 to 9, most preferably 7 residues. The core sequence may correspond identically to the sequence of a pilus subunit, or it may include one or more substitutions, preferably conservative substitutions, and/or insertions and/or deletions.

Moreover, the core sequence may be flanked at either of both of its N- and/or C-termini by residues of random sequence (i.e., sequences that do not necessarily correspond to the pilus subunit from which the core sequence is derived). When included, such flanking residues should not significantly alter the ability of the core sequence to disrupt subunit assembly. Thus, typically the compounds of the invention will include fewer than 5 flanking residues at each terminus, preferably fewer than 3 flanking residues, and most preferably no flanking residues.

Further, the peptides and/or peptide analogs may comprise hybrid sequences. For example, the peptide or peptide analog may include a core sequence derived from PapA flanked at one or both termini with sequences derived from FimA. Alternatively, the peptide or peptide analog may include a core sequence of, for example 10 residues, some of which are, for example, derived from PapA and the rest of which are, for example, derived from FimA.

In one illustrative embodiment, the compounds are 10 to 20 residue peptide and/or peptide analogs comprising formula (I):

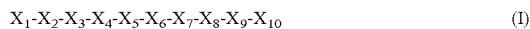

$$X_1\text{-}X_2\text{-}X_3\text{-}X_4\text{-}X_5\text{-}X_6\text{-}X_7\text{-}X_8\text{-}X_9\text{-}X_{10} \quad (I)$$

or a pharmaceutically-acceptable salt thereof, wherein:

$X_1$ is any amino acid residue, preferably other than a basic residue;

$X_2$ is any amino acid residue, preferably other than a aliphatic residue;

$X_3$ is a hydrophobic residue, preferably an aliphatic residue or a hydroxyl-substituted aliphatic residue;

$X_4$ is any amino acid residue, preferably other than an acidic residue;

$X_5$ is a hydrophobic residue or Gly;

$X_6$ is a hydrophobic or a hydrophilic residue;

$X_7$ is a hydrophobic residue, preferably Gly, an amide-substituted polar residue or an aliphatic residue, and most preferably Gly;

$X_8$ is any amino acid residue, preferably other than an aliphatic residue;

$X_9$ is an aliphatic residue; and $X_{10}$ is any amino acid residue, preferably a hydrophobic residue, more preferably an aliphatic residue or a polar residue.

In the compounds comprising formula (I), the symbol "-" between residues $X_n$ generally designates a backbone constitutive linking function. Thus, when the compounds are peptides, the symbol "-" represents a peptide or amide linkage (—C(O)NH—). It is to be understood, however, that formula (I) includes peptide analogs in which one or more amide linkages is optionally replaced with a linkage other than amide linkage, preferably a substituted amide or an isostere of amide linkage. Thus, while the various $X_n$ residues within formula (I) may conveniently be described in terms of "amino acids" or "residue," those having skill in the art will recognize that in embodiments having non-amide linkages, the term "amino acid" or "residue" as used herein refers to other bifunctional moieties bearing side-chain groups similar in structure to the side chains of the amino acids.

Substituted amide linkages generally include, but are not limited to, groups of the formula —C(O)N(R)—, where R is $(C_1\text{-}C_6)$ alkyl, substituted $(C_1\text{-}C_6)$ alkyl, $(C_2\text{-}C_6)$ alkenyl, substituted $(C_2\text{-}C_6)$ alkenyl, $(C_2\text{-}C_6)$ alkynyl, substituted $(C_2\text{-}C_6)$ alkynyl, $(C_5\text{-}C_{20})$ aryl, substituted $(C_5\text{-}C_{20})$ aryl, $(C_6\text{-}C_{26})$ arylalkyl, substituted $(C_6\text{-}C_{26})$ arylalkyl, 5–20 membered heteroaryl, substituted 5–20 membered heteroaryl, 6–26 membered heteroarylalkyl and substituted 6–26 membered heteroarylalkyl.

Isosteres of amide linkages generally include, but are not limited to, —CH$_2$NH—, —CH$_2$S—, —CH$_2$CH$_2$—, —CH=CH— (cis and trans), —C(O)CH$_2$—, —CH(OH)CH$_2$— and —CH$_2$SO—. Compounds having such non-amide linkages and methods for preparing such compounds are well-known in the art (see, e.g., Spatola, March 1983, Vega Data Vol. 1, Issue 3; Spatola, 1983, "Peptide Backbone Modifications" In: Chemistry and Biochemistry of Amino Acids Peptides and Proteins, Weinstein, ed., Marcel Dekker, New York, p. 267 (general review); Morley, 1980, Trends Pharm. Sci. 1:463–468; Hudson et al., 1979, Int. J. Prot. Res. 14:177–185 (—CH$_2$NH—, —CH$_2$CH$_2$—); Spatola et al., 1986, Life Sci. 38:1243–1249 (—CH$_2$—S); Hann, 1982, J. Chem. Soc. Perkin Trans. I. 1:307–314 (—CH=CH—, cis and trans); Almquist et al., 1980, J. Med. Chem. 23:1392–1398 (—COCH$_2$—); Jennings-White et al., Tetrahedron. Lett. 23:2533 (—COCH$_2$—); European Patent Application EP 45665 (1982) CA 97:39405 (—CH(OH)CH$_2$—); Holladay et al., 1983, Tetrahedron Lett. 24:4401–4404 (—C(OH)CH$_2$—); and Hruby, 1982, Life Sci. 31:189–199 (—CH$_2$—S—).

Additionally, one or more amide linkages can be replaced with peptidomimetic or amide mimetic moieties which do not significantly interfere with the structure or activity of the peptides. Suitable amide mimetic moieties are described, for example, in Olson et al., 1993, J. Med. Chem. 36:3039–3049.

Compounds comprising formula (I) that are peptide analogs may provide significant therapeutic advantages, as their non-peptide interlinkages may confer the compound with enhanced stability towards proteases and/or peptidases, thereby conferring the compounds with increases in vivo stability compared to a corresponding peptide.

The various residues $X_1$ through $X_{10}$ may be selected from amongst the genetically encoded amino acids, as well as from genetically non-encoded amino acids. Moreover, the residues may be in either the D- or L-configuration, as long as the compound retains activity. Compounds including D-amino acids may have enhanced in vivo stability. Preferably, all of residues $X_1$ through $X_{10}$ are in the L-configuration.

The peptides and peptide analogs of formula (I) may optionally include, in addition to the sequence defined by residues $X_1$ through $X_{10}$, a 1 to 5 residue peptide or peptide analog at either or both termini. Peptide analogs typically contain at least one modified interlinkage, such as a substituted amide or an isostere of an amide, as described above. Such additional peptides or peptide analogs may have an amino acid sequence derived from a pilus subunit or, alternatively, their sequences may be completely random. Compounds including such random sequences may be tested for biological activity in the various assays and methods described in a later section.

The residues which comprise such additional peptides or peptide analogs may be genetically encoded or non-encoded, and may be in either the D- or L-configuration. In one embodiment, when the sequence defined by formula (I) is a peptide, one or both termini are "capped" with 1 to 5 residue peptides composed wholly of D-amino acids that serve to protect the core sequence from degradation in vivo by proteases and/or peptidases.

Also included within the scope of the present invention are "blocked" forms of the peptides and peptide analogs including formula (I), i.e., 10 to 20 peptides and/or peptide analogs in which the N- and/or C-terminus is blocked with a moiety capable of reacting with the N-terminal —NH$_2$ or C-terminal —C(O)OH. Such blocked compounds are typically N-terminal acylated and/or C-terminal amidated or esterified. Typical N-terminal blocking groups include R$^1$C(O)—, where R$^1$ is hydrogen, $(C_1\text{-}C_6)$ alkyl, $(C_2\text{-}C_6)$ alkenyl, ($C_2$–$C_6$) alkynyl, ($C_5$–$C_{20}$) aryl, ($C_6$–$C_{26}$) arylalkyl, 5–20 membered heteroaryl or 6–26 membered heteroarylalkyl. Preferred N-terminal blocking groups include acetyl, formyl and dansyl. Typical C-terminal blocking groups include —C(O)NR$^1$R$^1$ and —C(O)OR$^1$, where each R$^1$ is independently as defined as above. Preferred C-terminal blocking groups include those in which each R$^1$ is independently ($C_1$–$C_6$) alkyl, preferably methyl, ethyl, propyl or isopropyl Preferred amongst the 10 to 20 residue peptides and/or peptide analogs comprising formula (I) are those compounds having one or more or the following characteristics:

$X_3$ is an aliphatic residue or T;
$X_S$ is an aliphatic residue, F or G; and/or
$X_7$ is G, N or A.

Particularly preferred are the 10-residue peptides described in Table 2, below.

TABLE 2

SUBUNIT N-TERMINAL-MOTIF-DERIVED PEPTIDES

| AMINO ACID SEQUENCE | | PILUS SUBUNIT |
|---|---|---|
| GKVTFNGTVV | (SEQ ID NO: 2) | PapA, PrsA |
| GTVHFKGEVV | (SEQ ID NO: 3) | FimA, SfaA, FocA |
| GKVTFFGKVV | (SEQ ID NO: 4) | HifA, HafA |
| GTIVITGTIT | (SEQ ID NO: 5) | Fim2 |
| GTIVITGSIS | (SEQ ID NO: 6) | Fim3 |
| GTVKFVGSII | (SEQ ID NO: 7) | MrpA |
| GEIQLKGEIV | (SEQ ID NO: 8) | PmfA |
| GTIKFTGEIV | (SEQ ID NO: 9) | LpfA |
| NEVTFLGSVS | (SEQ ID NO: 10) | PefA |
| GTINFEGSVV | (SEQ ID NO: 11) | AtfA |
| SDVAFRGNLL | (SEQ ID NO: 12) | PapK, PrsK |
| GRAAFHGEVV | (SEQ ID NO: 13) | PapH |
| GRATFHGEVV | (SEQ ID NO: 14) | PrsH |
| DNLTFRGKLI | (SEQ ID NO: 15) | PapE |
| DNLTFKGKLI | (SEQ ID NO: 16) | PrsE |
| GWLNLQGTIL | (SEQ ID NO: 17) | MrpB |
| SVVNITGNVQ | (SEQ ID NO: 18) | SfaG |
| TTITVTGNVL | (SEQ ID NO: 19) | SfaS |
| TTITVTGRVL | (SEQ ID NO: 20) | FocG |
| CMLAGSNFVT | (SEQ ID NO: 21) | FocF |
| VQINIRGNVY | (SEQ ID NO: 22) | PapF, PrsF |
| PNLKLFGTLL | (SEQ ID NO: 23) | MrpF |
| VYINITGNVI | (SEQ ID NO: 24) | MrpE |
| GKITFNGKVV | (SEQ ID NO: 25) | F17A |
| GTINFNGKIT | (SEQ ID NO: 26) | FanC |
| QKTIFSADVV | (SEQ ID NO: 27) | FaeA |
| GQVNFFGKVT | (SEQ ID NO: 28) | MrkA |
| QRTIITADVV | (SEQ ID NO: 29) | RalC |

In a preferred embodiment of the invention, the compounds are peptides or peptide analogs that mimic the binding activity of the $G_1$ beta-strand of a chaperone and that exhibit antibacterial activity against a Gram-negative bacterium. The core sequence of such peptides and peptide analogs may be derived from the $G_1$ beta-strand of any of a number of chaperones, including but not limited to, PapD, MrpD, FanE, SfaE, FaeE, MrkB, HifB, F17D, FimC, FimB, PefD, EcpD, ClpE, YehC, PmfF, FocC, LpfB, SefB, Caf1M, CS3-1, CsaB, MyfB, AggD, CssC, NfaA and AfaB. Typically, the core sequence is composed of about 3 to about 12 residues, preferably from 4 to 9 residues and most preferably 7 residues. The core sequence may correspond identically to the $G_1$ beta-strand sequence of a chaperone, or it may include one or more substitutions, preferably conservative substitutions, and/or insertions and/or deletions.

Moreover, the core sequence may be flanked at either of both of its N- and/or C-termini by residues of random sequence (i.e., sequences that do not necessarily correspond to the $G_1$ beta-strand from which the core sequence is derived). When included, such flanking residues should not significantly alter the ability of the core sequence to mimic the binding activity of the $G_1$ beta-strand of a chaperone. Thus, typically the compounds of the invention will include fewer than 5 flanking residues at each terminus, preferably fewer than 3 flanking residues and most preferably no flanking residues.

Further, the peptides and/or peptide analogs may comprise hybrid sequences. For example, the peptide or peptide analog may include a core sequence derived from the $G_1$ beta-strand of a PapD chaperone flanked at one or both termini with sequences derived from an MrpD chaperone. Alternatively, the peptide or peptide analog may include a core sequence of, for example 7 residues, some of which are, for example, derived from a PapD chaperone and the rest of which are derived from, for example a FanE chaperone.

In one illustrative embodiment, the compounds are 7 to 17 residue peptide and/or peptide analogs comprising formula (II):

$$X_{11}\text{-}X_{12}\text{-}X_{13}\text{-}X_{14}\text{-}X_{15}\text{-}X_{16}\text{-}X_{17} \quad \text{(II)}$$

or a pharmaceutically-acceptable salt thereof, wherein:

$X_{11}$ is any amino acid residue, preferably other than a basic residue;

$X_{12}$ is any amino acid residue;

$X_{13}$ is a hydrophobic residue, preferably an aliphatic residue or an apolar residue, wherein the apolar residue is preferably M;

$X_{14}$ is any amino acid residue, preferably other than an aromatic residue;

$X_{15}$ is a hydrophobic residue, preferably an aliphatic residue;

$X_{16}$ is any amino acid residue, preferably an aliphatic residue or a hydroxyl-substituted aliphatic residue; and $X_{17}$ is hydrophobic residue or a hydroxyl-substituted aliphatic residue, preferably an aliphatic residue, F, M or a hydroxyl-substituted aliphatic residue.

In the compounds comprising (II), the symbol "-" between residues $X_n$ is as previously defined for formula (I).

The various residues $X_{11}$ through $X_{17}$ may be selected from amongst the genetically encoded amino acids, as well as from genetically non-encoded amino acids. Moreover, the residues may be in either the D- or L-configuration, as long as the compound retains activity. Compounds including D-amino acids may have enhanced in vivo stability. Preferably, all of residues $X_{11}$ through $X_{17}$ are in the L-configuration.

The peptides and peptide analogs of formula (II) may optionally include, in addition to the sequence defined by residues $X_{11}$ through $X_{17}$, a 1 to 5 residue peptide or peptide analog at either or both termini. Peptide analogs typically contain at least one modified interlinkage, such as a substituted amide or an isostere of an amide, as described above. Such additional peptides or peptide analogs may have an amino acid sequence derived from the $G_1$ beta-strand of a chaperone or, alternatively, their sequences may be completely random. Compounds including such random sequences may be tested for biological activity in the various assays and methods described in a later section.

The residues which comprise such additional peptides or peptide analogs may be genetically encoded or non-encoded, and may be in either the D- or L-configuration. In one convenient embodiment, when the sequence defined by formula (II) is a peptide, one or both termini are "capped" with 1 to 5 residue peptides composed wholly of D-amino acids that serve to protect the core sequence from degradation in vivo by proteases and/or peptidases.

Also included within the scope of the present invention are "blocked" forms of the peptides and peptide analogs including formula (II), as previously described in connection with compounds comprising formula (I).

Preferred amongst the 7 to 17 residue peptides and/or peptide analogs comprising formula (II) are those compounds having one or more or the following characteristics:

$X_{13}$ is an aliphatic residue or M;
$X_{15}$ is an aliphatic residue, F or M; and/or
$X_{17}$ is an aliphatic residue, F, M or T.

Particularly preferred are the 7-residue peptides described in Table 3, below.

TABLE 3

CHAPERONE G, BETA-STRAND-DERIVED PEPTIDES

| AMINO ACID SEQUENCE | | CHAPERONE |
|---|---|---|
| NVLQIAL | (SEQ ID NO: 1) | PapD, MrpD |
| GSLSLAI | (SEQ ID NO: 30) | FanE |
| NYLQFAI | (SEQ ID NO: 31) | SfaE |
| SGIAVAL | (SEQ ID NO: 32) | FaeE |
| NILQLAI | (SEQ ID NO: 33) | MrkB |
| SFMQIAI | (SEQ ID NO: 34) | HifB |
| NYLQFAV | (SEQ ID NO: 35) | F17D |
| NTLQLAI | (SEQ ID NO: 36) | FimC |
| GVLQLTI | (SEQ ID NO: 37) | FimB |
| NVLAVAV | (SEQ ID NO: 38) | PefD |
| SLLQLAF | (SEQ ID NO: 39) | EcpD |
| SGIAVAV | (SEQ ID NO: 40) | ClpE |
| NALKFAM | (SEQ ID NO: 41) | YehC |
| NVLQMAM | (SEQ ID NO: 42) | PmfD |
| NYLQFAI | (SEQ ID NO: 43) | FocC |
| NVLQIAV | (SEQ ID NO: 44) | LpfB |
| LNVNVVT | (SEQ ID NO: 45) | SefB |
| VFVQFAI | (SEQ ID NO: 46) | Caf1M |
| MKLNVSI | (SEQ ID NO: 47) | CS3-1 |
| MDIQMSI | (SEQ ID NO: 48) | PsaB |
| LNILLSV | (SEQ ID NO: 49) | MyfB |
| MNIQVSV | (SEQ ID NO: 50) | AggD |
| DSINISI | (SEQ ID NO: 51) | CssC |
| LNVQLSV | (SEQ ID NO: 52) | NfaA, AfaB |

Deletion of residues from either terminus of the peptides and peptides analogs of formula (I) or (II) are also contemplated to be within the scope of the invention. Such deletions consisting of the removal of one or more amino acids of the peptide sequence, with the lower limit length of the resulting peptide sequence being 3 to 7 amino acids, preferably 3 to 5 amino acids. Such deletions may involve a single contiguous or greater than one discrete portion of the peptide sequences. One or more such deletions may be introduced into the sequence, as long as such deletions result in peptides which may still bind in whole, or in part, to a pilus subunit and consequentially prevent or inhibit pilus biogenesis.

It will be appreciated that by virtue of the present invention, the above-described polypeptides can be synthesized using conventional synthesis procedures commonly used by one skilled in the art. For example, the polypeptides can be chemically synthesized using an automated peptide synthesizer (such as one manufactured by Pharmacia LKB Biotechnology Co., LKB Biolynk 4170 or Milligen, Model 9050 (Milligen, Millford, Mass.)) following the method of Sheppard, et al., Journal of Chemical Society Perkin I, p. 538 (1981). In this procedure, N,N'-dicyclohexylcarbodiimide is added to amino acids whose amine functional groups are protected by 9-flourenylmethoxycarbonyl (Fmoc) groups and anhydrides of the desired amino acids are produced. These Fmoc-amino acid anhydrides can then be used for peptide synthesis. A Fmoc-amino acid anhydride corresponding to the C-terminal amino acid residue is fixed to Ultrosyn A resin through the carboxyl group using dimethylaminopyridine as a catalyst. Next, the resin is washed with dimethylformamide containing piperidine, and the protecting group of the amino functional group of the C-terminal acid is removed. The next amino acid corresponding to the desired peptide is coupled to the C-terminal amino acid. The deprotecting process is then repeated. Successive desired amino acids are fixed in the same manner until the peptide chain of the desired sequence is formed. The protective groups other than the acetoamidomethyl are then removed and the peptide is released with solvent.

Alternatively, the polypeptides can be synthesized by using nucleic acid molecules which encode the peptides of this invention in an appropriate expression vector which include the encoding nucleotide sequences. Such DNA molecules may be readily prepared using an automated DNA sequencer and the well-known codon-amino acid relationship of the genetic code. Such a DNA molecule also may be obtained as genomic DNA or as cDNA using oligonucleotide probes and conventional hybridization methodologies. Such DNA molecules may be incorporated into expression vectors, including plasmids, which are adapted for the expression of the DNA and production of the polypeptide in a suitable host such as bacterium, e.g., *Escherichia coli*, yeast cell or mammalian cell.

It is known that certain modifications can be made without completely abolishing the polypeptide's antibacterial activity. Modifications include the removal and addition of amino acids. Polypeptides containing other modifications can be synthesized by one skilled in the art and compounds comprising such polypeptides may be tested for biological activity in the various assays and methods described in a later section. Thus, the effectiveness of the polypeptides can be modulated through various changes in the amino acid sequence or structure.

Further, it should be understood that the mimic may be modified using methods known in the art to improve binding, specificity, solubility, safety, or efficacy. A necessary characteristic of these preferred compounds is the capability to interact with at least one pilus subunit during transport of these pilus subunits through periplasmic space and/or during the process of assembly of the intact pilus, in such a manner that pilus biogenesis is prevented or inhibited. The compound can be any compound, preferably a peptide, which has one of the above effects on pilus subunits and thereby on the assembly of an intact pilus.

Morever, the present invention is directed to a compound which will mimic the capability of mannose to bind to the mannose binding site at the tip of the FimH adhesin, thereby preventing or inhibiting the ability of the pilus to adhere and infect host tissues. As discussed above, the bottom of this mannose-binding domain of FimH is lined with asparagine, glutamine and aspartic acid residues and those skilled in the art would be able to use molecular modeling techniques and other existing protocol to design and synthesize antibacterial compounds. Such compounds would compete with mannose for binding to the FimH adhesin thereby preventing or inhibiting pilus adhesion to host epithelium. As such, these compounds may be used in methods of preventing or inhibiting pili adhesion to a host tissue.

The present invention also provides a method for inhibiting bacterial colonization by a Gram-negative organism. This method involves administration of a compound which will interfere with the binding of a chaperone to a pilus subunit, thereby preventing the assembly of an intact pilus structure. In a preferred embodiment of the invention, a method of preventing or inhibiting the assembly of pilus subunits is provided by interfering with, in the PapK pilus subunit, a binding site which is normally involved in the binding to pilus subunits during transport of these pilus subunits through the periplasmic space and/or during the process of pilus assembly. In another embodiment of the invention, a method of preventing or inhibiting the assembly of pilus subunits is provided by interfering with, in the FimC pilus subunit, a binding site which is normally involved in the binding to pilus subunits during transport of these pilus subunits through the periplasmic space and/or during the process of pilus assembly.

Antibacterial Compounds and Pharmaceutical Compositions

In another preferred embodiment of the invention, a method of preventing or inhibiting the assembly of pilus subunits is provided by administering an antibacterial compound which will mimic the capability of a periplasmic chaperone or a pilus subunit to bind to a pilus subunit. Also provided is a method of preventing or inhibiting the adhesion of a pilus to a host tissue by administering an antibacterial compound which will bind to a pilus mannose-binding domain.

The antibacterial compositions of the present invention may be utilized to inhibit pili assembly and/or pili adhesion by providing an effective amount of such compositions to a patient.

For use as antimicrobials for treatment of animal subjects, the compounds of the invention can be formulated as pharmaceutical or veterinary compositions. Depending on the subject to be treated, the mode of administration, and the type of treatment desired, e.g., prevention, prophylaxis, therapy; the compounds are formulated in ways consonant with these parameters. A summary of such techniques is found in Remington's Pharmaceutical Sciences, latest edition, Mack Publishing Co., Easton, Pa.

For administration to animal or human subjects, the dosage of the compounds of the invention is typically 0.1–100 mg/kg. However, dosage levels are highly dependent on the nature of the infection, the condition of the patient, the judgment of the practitioner, and the frequency and mode of administration. The dosage of such a substance is expected to be the dosage which is normally employed when administering antibacterial drugs to patients or animals, i.e. 1 μg–1000 μg per kilogram of body weight per day. The dosage will depend partly on the route of administration of the substance. If the oral route is employed, the absorption of the substance will be an important factor. A low absorption will have the effect that in the gastro-intestinal tract higher concentrations, and thus higher dosages, will be necessary. Also, the dosage of such a substance when treating infections of the central nervous system (CNS) will be dependent on the permeability of the blood-brain barrier for the substance. As is well-known in the treatment of bacterial meningitis with penicillin, very high dosages are necessary in order to obtain effective concentrations in the CNS.

It will be understood that the appropriate dosage of the substance should suitably be assessed by performing animal model tests, wherein the effective dose level (e.g. $ED_{50}$) and the toxic dose level (e.g. $TD_{50}$) as well as the lethal dose level (e.g. $LD_{50}$ or $LD_{10}$) are established in suitable and acceptable animal models. Further, if a substance has proven efficient in such animal tests, controlled clinical trials should be performed. Needless to state such clinical trials should be performed according to the standards of Good Clinical Practice.

In general, for use in treatment, the compounds of the invention may be used alone or in combination with other antibiotics such as erythromycin, tetracycline, macrolides, for example azithromycin and the cephalosporins. Depending on the mode of administration, the compounds will be formulated into suitable compositions to permit facile delivery to the affected areas.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like.

For oral administration, the compounds can be administered also in liposomal compositions or as microemulsions. Suitable forms include syrups, capsules, tablets, as is understood in the art. For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

It will be understood that the above-described methods comprising administration of substances in treating and/or preventing diseases are dependent on the identification or de novo design of substances which are capable of exerting effects which will lead to prevention or inhibition of the interaction between pilus subunits and periplasmic molecular chaperones. It is further important that these substances will have a high chance of being therapeutically active.

Thus clinical experimental trials and animal studies can be undertaken to demonstrate the therapeutic efficacy of peptide mimics and analogues for preventing or inhibiting pilus assembly. The efficacy of such compounds can be shown using methods known in the art, including pilus inhibition and binding assays, specifically ELISA or hemagglutination.

The antibacterial compositions of the present invention also have a variety of industrial uses, well known to those skilled in such arts, relating to their antibacterial properties. In general, these uses are carried out by bringing a biocidal or bacterial inhibitory amount of the antibacterial compositions of the present invention into contact with a surface, environment or biozone containing Gram-negative bacteria so that the composition is able to interact with and thereby interfere with the biological function of such bacteria. For example, such antibacterial compositions can be used to prevent or inhibit biofilm formation caused by Gram-negative bacteria and to inhibit bacterial colonization by a Gram-negative organism. Compositions may be formulated as sprays, solutions, pellets, powders and in other forms of administration well known to those skilled in such arts.

Crystalline PapD-PapK Chaperone-Subunit Co-Complex and FimH-FimC Chaperone-Adhesin Co-Complex The present invention provides, for the first time, the high-resolution three-dimensional structure and atomic structure coordinates of the crystalline co-complexes of the PapD-PapK chaperone-subunit as determined by X-ray crystallography. Also provided for usage in the methods of the present invention is the high resolution three dimensional structures and atomic structure coordinates for the crystalline co-complexes of the FimC-FimH chaperone-adhesin as determined by X-ray crystallography. The specific methods used to obtain the structure coordinates are provided in the examples, infra. The atomic structure coordinates of crystalline PapD-PapK co-complex, obtained from the co-crystal to 2.4 Å resolution, are listed in Table 4. The atomic structure coordinates of crystalline FimC-FimH co-complex, obtained from the co-crystal to 2.5 Å resolution, are listed in Table 5.

Additional antibacterial compounds can be modeled and synthesized utilizing the atomic coordinates obtained from the resolution of the co-crystal structure of the PapD-PapK chaperone-subunit co-complex and the FimC-FimH chaperone-adhesin co-complex. For example, as discussed herein, applicants utilized the co-crystal structure of the FimC-FimH chaperone-adhesion co-complex to identify the $NH_2$-terminal mannose-binding domain of FimH, an essential component required for pilus adhesion to host tissues. As the COOH-terminus of pilus subunits in many tissue-adhering bacteria have been found to be highly conserved, it is believed that the antibacterial compounds of the present invention are capable of interacting with the majority of pilus subunits and thus are useful in the treatment of various diseases caused by piliated bacteria.

Thus, the invention encompasses a co-crystal of a pilus chaperone-subunit co-complex comprising an amino acid sequence of a $G_1$ beta-strand of a periplasmic chaperone and an amino acid sequence from the amino-terminal sequence of a pilus subunit. Preferably, the amino acid sequence of a $G_1$ beta-strand would be the N101 to L107 amino acid region of a $G_1$ beta-strand of a pilus chaperone, and even more preferably, the amino acid sequence of a $G_1$ beta-strand would be the N101 to L107 amino acid region of a $G_1$ beta-strand of a PapD chaperone and most preferably, the amino acid sequence of the $G_1$ beta-strand would be SEQ ID NO: 1. Preferably, the amino acid sequence of the amino-terminal sequence would be from the N-terminal sequence of a PapK subunit, and more preferably, the amino acid sequence of the amino-terminal sequence would be the amino acid sequence of SEQ ID NO: 12. In a preferred embodiment, the co-crystal is a crystalline form of the polypeptides corresponding to the PapD-PapK chaperone-subunit co-complex. In a preferred embodiment of the invention, the co-crystal effectively diffracts X-rays for the determination of the atomic coordinates of the pilus chaperone-subunit co-complex to a resolution of from about 3 angstroms to about 2.4 angstroms or greater.

Preferably, co-crystals of the invention comprise crystallized polypeptides corresponding to the wild-type PapD-PapK chaperone-subunit co-complex. The co-crystals of the invention include native co-crystals in which the crystallized PapD-PapK chaperone-subunit co-complex is substantially pure and heavy-atom atom derivative co-crystals in which the crystallized PapD-PapK chaperone-subunit co-complex is in association with one or more heavy-metal atoms. The co-crystals from which the atomic structure coordinates of the crystalline co-complexes of the present invention may be obtained include native co-crystals and heavy-atom derivative co-crystals. Native co-crystals generally comprise substantially pure polypeptides corresponding to the PapD-PapK co-complex in crystalline form.

It is to be understood that the crystalline PapD-PapK co-complex from which the atomic structure coordinates of the invention can be obtained is not limited to the wild-type PapD-PapK co-complex. Indeed, the co-crystals may comprise mutants of the wild-type co-complex. Mutants of wild-type co-complexes are obtained by replacing at least one amino acid residue in the sequences of one or both the polypeptides comprising the wild-type co-complex with a different amino acid residue, or by adding or deleting one or more amino acid residues within the wild-type sequences and/or at the N- and/or C-terminus of one of both of the polypeptides comprising the wild-type co-complex. Preferably, such mutants will crystallize under crystallization conditions that are substantially similar to those used to crystallize the wild-type co-complex.

The types of mutants contemplated by this invention include conservative mutants, non-conservative mutants, deletion mutants, truncated mutants, extended mutants, methionine mutants, selenomethionine mutants, cysteine mutants and selenocysteine mutants. A mutant may have, but need not have, pilus subunit binding activity. Preferably, a mutant displays biological activity that is substantially similar to that of the wild-type polypeptide. Methionine, selenomethione, cysteine, and selenocysteine mutants are particularly useful for producing heavy-atom derivative co-crystals, as described in detail, below.

It will be recognized by one of skill in the art that the types of mutants contemplated herein are not mutually exclusive; that is, for example, a polypeptide having a conservative mutation in one amino acid may in addition have a truncation of residues at the N-terminus, and several Leu or Ile→Met mutations.

Sequence alignments of polypeptides in a protein family or of homologous polypeptide domains can be used to identify potential amino acid residues in the polypeptide sequence that are candidates for mutation. Identifying mutations that do not significantly interfere with the three-dimensional structure of the PapD-PapK co-complex and the FimC-FimH co-complex and/or that do not deleteriously affect, and that may even enhance, the activity of the co-complex will depend, in part, on the region where the mutation occurs.

Conservative amino acid substitutions are well-known in the art, and include substitutions made on the basis of a similarity in polarity, charge, solubility, hydrophobicity and/or the hydrophilicity of the amino acid residues involved. Typical conservative substitutions are those in which the amino acid is substituted with a different amino acid that is a member of the same class or category, as those classes are defined herein. Thus, typical conservative substitutions include aromatic to aromatic, apolar to apolar, aliphatic to aliphatic, acidic to acidic, basic to basic, polar to polar, etc. Other conservative amino acid substitutions are well known in the art. It will be recognized by those of skill in the art that generally, a total of about 20% or fewer, typically about 10% or fewer, most usually about 5% or fewer, of the amino acids in the wild-type polypeptide sequence can be conservatively substituted with other amino acids without deleteriously affecting the biological activity and/or three-dimensional structure of the molecule, provided that such substitutions do not involve residues that are critical for activity, as discussed above.

The heavy-atom derivative co-crystals from which the atomic structure coordinates of the invention are obtained generally comprise a crystalline co-complex in association with one or more heavy metal atoms. The polypeptides may correspond to a wild-type or a mutant PapD-PapK co-complex or FimC-FimH co-complex, which may optionally be further associated with one or more molecules. There are two types of heavy-atom derivatives of polypeptides: heavy-atom derivatives resulting from exposure of the proteins to a heavy metal in solution, wherein co-crystals are grown in medium comprising the heavy metal, or in crystalline form, wherein the heavy metal diffuses into the co-crystal, and heavy-atom derivatives wherein at least one of the polypeptides in the co-complex comprises heavy-atom containing amino acids, e.g., selenomethionine and/or selenocysteine mutants.

In practice, heavy-atom derivatives of the first type can be formed by soaking a native co-crystal in a solution comprising heavy metal atom salts, or organometallic compounds, e.g., lead chloride, gold thiomalate, thimerosal, uranyl acetate, platinum tetrachloride, osmium tetraoxide, zinc sulfate, and cobalt hexamine, which can diffuse through the co-crystal and bind to the crystalline polypeptides.

Heavy-atom derivatives of this type can also be formed by adding to a crystallization solution comprising the polypeptides to be co-crystallized an amount of a heavy metal atom salt, which may associate with at least one of the protein and be incorporated into the co-crystal. The location(s) of the bound heavy metal atom(s) can be determined by X-ray diffraction analysis of the co-crystal. This information, in turn, is used to generate the phase information needed to construct the three-dimensional structure of the proteins in the co-complex.

The native and/or heavy-atom derivative co-crystals from which the atomic structure coordinates of the invention are obtained can be obtained by conventional means as are well-known in the art of protein crystallography, including batch, liquid bridge, dialysis, and vapor diffusion methods (see, e.g., McPherson, 1982, Preparation and Analysis of Protein Crystals, John Wiley, New York; McPherson, 1990, Eur. J. Biochem. 189:1–23.; Weber, 1991, Adv. Protein Chem. 41:1–36.). Generally, native co-crystals are grown by dissolving substantially pure polypeptide encoding for the PapD-PapK co-complex or the FimH-FimC co-complex in an aqueous buffer containing a precipitant at a concentration just below that necessary to precipitate the protein. Examples of precipitants include, but are not limited to, polyethylene glycol, ammonium sulfate, 2-methyl-2,4-pentanediol, sodium citrate, sodium chloride, glycerol, isopropanol, lithium sulfate, sodium acetate, sodium formate, potassium sodium tartrate, ethanol, hexanediol, ethylene glycol, dioxane, t-butanol and combinations thereof. Water is removed by controlled evaporation to produce precipitating conditions, which are maintained until co-crystal growth ceases.

In a preferred embodiment, native co-crystals are grown by vapor diffusion in hanging drops (McPherson, 1982, Preparation and Analysis of Protein Crystals, John Wiley, New York; McPherson, 1990, Eur. J. Biochem. 189:1–23.). In this method, the polypeptide/precipitant solution is allowed to equilibrate in a closed container with a larger aqueous reservoir having a precipitant concentration optimal for producing crystals. Generally, less than about 25 µL of substantially pure polypeptide solution is mixed with an equal volume of reservoir solution, giving a precipitant concentration about half that required for crystallization. This solution is suspended as a droplet underneath a coverslip, which is sealed onto the top of the reservoir. The sealed container is allowed to stand, usually for about 2–6 weeks, until co-crystals grow.

Heavy-atom derivative co-crystals can be obtained by soaking native co-crystals in mother liquor containing salts of heavy metal atoms. Further, heavy-atom derivative co-crystals can also be obtained from SeMet and/or SeCys mutants, as described above for native co-crystals.

Mutant proteins may crystallize under slightly different crystallization conditions than wild-type protein, or under very different crystallization conditions, depending on the nature of the mutation, and its location in the protein. For example, a non-conservative mutation may result in alteration of the hydrophilicity of the mutant, which may in turn make the mutant protein either more soluble or less soluble than the wild-type protein. Typically, if a protein becomes more hydrophilic as a result of a mutation, it will be more soluble than the wild-type protein in an aqueous solution and a higher precipitant concentration will be needed to cause it to crystallize. Conversely, if a protein becomes less hydrophilic as a result of a mutation, it will be less soluble in an aqueous solution and a lower precipitant concentration will be needed to cause it to crystallize. If the mutation happens to be in a region of the protein involved in crystal lattice contacts, crystallization conditions may be affected in more unpredictable ways.

The dimensions of a unit cell of a crystal are defined by six numbers, the lengths of three unique edges, a, b, and c, and three unique angles, $\alpha$, $\beta$ and $\gamma$. The type of unit cell that comprises a crystal is dependent on the values of these variables. In one embodiment, the co-crystal of the PapD-PapK pilus chaperone-subunit co-complex has the space group of $P2_12_12_1$ with unit cell dimensions of a=62.1±0.2 angstroms, b=63.6±0.2 angstroms and c=92.7±0.2 angstroms such that the three dimensional structure of the crystallized co-complex can be determined to a resolution of from about 3 angstroms to about 2.4 angstroms or greater. In another embodiment, the co-crystals of the FimC-FimH chaperone-adhesin co-complex has the space group $P4_12_12$ of $P4_3$ with unit cell dimensions of a=b=97.7±0.2 angstroms and c=215.9±0.2 angstroms such that the three-dimensional structure of the co-complex can be determined to a resolution of from about 3 angstroms to about 2.5 angstroms or greater.

When a crystal is placed in an X-ray beam, the incident X-rays interact with the electron cloud of the molecules that make up the crystal, resulting in X-ray scatter. The combination of X-ray scatter with the lattice of the crystal gives rise to nonuniformity of the scatter; areas of high intensity are called diffracted X-rays. The angle at which diffracted beams emerge from the crystal can be computed by treating diffraction as if it were reflection from sets of equivalent, parallel planes of atoms in a crystal (Bragg's Law). The most obvious sets of planes in a crystal lattice are those that are parallel to the faces of the unit cell. These and other sets of planes can be drawn through the lattice points. Each set of planes is identified by three indices, hkl. The h index gives the number of parts into which the a edge of the unit cell is cut, the k index gives the number of parts into which the b edge of the unit cell is cut, and the l index gives the number of parts into which the c edge of the unit cell is cut by the set of hkl planes. Thus, for example, the 235 planes cut the a edge of each unit cell into halves, the b edge of each unit cell into thirds, and the c edge of each unit cell into fifths. Planes that are parallel to the bc face of the unit cell are the 100 planes; planes that are parallel to the ac face of the unit cell are the 010 planes; and planes that are parallel to the ab face of the unit cell are the 001 planes.

When a detector is placed in the path of the diffracted X-rays, in effect cutting into the sphere of diffraction, a series of spots, or reflections, are recorded to produce a "still" diffraction pattern. Each reflection is the result of X-rays reflecting off one set of parallel planes, and is characterized by an intensity, which is related to the distribution of molecules in the unit cell, and hkl indices, which correspond to the parallel planes from which the beam producing that spot was reflected. If the crystal is rotated about an axis perpendicular to the X-ray beam, a large number of reflections is recorded on the detector, resulting in a diffraction pattern.

The unit cell dimensions and space group of a crystal can be determined from its diffraction pattern. First, the spacing of reflections is inversely proportional to the lengths of the edges of the unit cell. Therefore, if a diffraction pattern is recorded when the X-ray beam is perpendicular to a face of the unit cell, two of the unit cell dimensions may be deduced from the spacing of the reflections in the x and y directions of the detector, the crystal-to-detector distance, and the wavelength of the X-rays. Those of skill in the art will appreciate that, in order to obtain all three unit cell dimensions, the crystal must be rotated such that the X-ray beam is perpendicular to another face of the unit cell. Second, the angles of a unit cell can be determined by the angles between lines of spots on the diffraction pattern. Third, the absence of certain reflections and the repetitive nature of the diffraction pattern, which may be evident by visual inspection, indicate the internal symmetry, or space group, of the crystal. Therefore, a crystal may be characterized by its unit cell and space group, as well as by its diffraction pattern.

Once the dimensions of the unit cell are determined, the likely number of polypeptides in the asymmetric unit can be deduced from the size of the polypeptide, the density of the average protein, and the typical solvent content of a protein crystal, which is usually in the range of 30–70% of the unit cell volume.

The diffraction pattern is related to the three-dimensional shape of the molecule by a Fourier transform. The process of determining the solution is in essence a re-focusing of the diffracted X-rays to produce a three-dimensional image of the molecule in the crystal. Since re-focusing of X-rays cannot be done with a lens at this time, it is done via mathematical operations.

The sphere of diffraction has symmetry that depends on the internal symmetry of the crystal, which means that certain orientations of the crystal will produce the same set of reflections. Thus, a crystal with high symmetry has a more repetitive diffraction pattern, and there are fewer unique reflections that need to be recorded in order to have a complete representation of the diffraction. The goal of data collection, a dataset, is a set of consistently measured, indexed intensities for as many reflections as possible. A complete dataset is collected if at least 80%, preferably at least 90%, most preferably at least 95% of unique reflections are recorded. In one embodiment, a complete dataset is collected using one crystal. In another embodiment, a complete dataset is collected using more than one crystal of the same type.

Sources of X-rays include, but are not limited to, a rotating anode X-ray generator such as a Rigaku RU-200 or a beamline at a synchrotron light source, such as the Advanced Photon Source at Argonne National Laboratory. Suitable detectors for recording diffraction patterns include, but are not limited to, X-ray sensitive film, multiwire area detectors, image plates coated with phosphorus, and CCD cameras. Typically, the detector and the X-ray beam remain stationary, so that, in order to record diffraction from different parts of the crystal's sphere of diffraction, the crystal itself is moved via an automated system of moveable circles called a goniostat.

One of the biggest problems in data collection, particularly from macromolecular crystals having a high solvent content, is the rapid degradation of the crystal in the X-ray beam. In order to slow the degradation, data is often collected from a crystal at liquid nitrogen temperatures. In order for a crystal to survive the initial exposure to liquid nitrogen, the formation of ice within the crystal must be prevented by the use of a cryoprotectant. Suitable cryoprotectants include, but are not limited to, low molecular weight polyethylene glycols, ethylene glycol, sucrose, glycerol, xylitol, and combinations thereof. Crystals may be soaked in a solution comprising the one or more cryoprotectants prior to exposure to liquid nitrogen, or the one or more cryoprotectants may be added to the crystallization solution. Data collection at liquid nitrogen temperatures may allow the collection of an entire dataset from one crystal.

Once a dataset is collected, the information is used to determine the three-dimensional structure of the molecule in the crystal. However, this cannot be done from a single measurement of reflection intensities because certain information, known as phase information, is lost between the three-dimensional shape of the molecule and its Fourier transform, the diffraction pattern. This phase information must be acquired by methods described below in order to perform a Fourier transform on the diffraction pattern to obtain the three-dimensional structure of the molecule in the crystal. It is the determination of phase information that in effect refocuses X-rays to produce the image of the molecule.

One method of obtaining phase information is by isomorphous replacement, in which heavy-atom derivative crystals are used. In this method, the positions of heavy atoms bound to the molecules in the heavy-atom derivative crystal are determined, and this information is then used to obtain the phase information necessary to elucidate the three-dimensional structure of a native crystal. (Blundel et al., 1976, Protein Crystallography, Academic Press).

Another method of obtaining phase information is by molecular replacement, which is a method of calculating initial phases for a new crystal of a polypeptide or polypeptide co-complex whose structure coordinates are unknown by orienting and positioning a polypeptide whose structure coordinates are known within the unit cell of the new crystal so as to best account for the observed diffraction pattern of the new crystal. Phases are then calculated from the oriented and positioned polypeptide and combined with observed amplitudes to provide an approximate Fourier synthesis of the structure of the molecules comprising the new crystal. (Lattman, 1985, Methods in Enzymology 115:55–77; Rossmann, 1972, "The Molecular Replacement Method," Int. Sci. Rev. Ser. No. 13, Gordon & Breach, New York).

A third method of phase determination is multi-wavelength anomalous dispersion or MAD. In this method, X-ray diffraction data are collected at several different wavelengths from a single crystal containing at least one heavy atom with absorption edges near the energy of incoming X-ray radiation. The resonance between X-rays and electron orbitals leads to differences in X-ray scattering that permits the locations of the heavy atoms to be identified, which in turn provides phase information for a crystal of a polypeptide. A detailed discussion of MAD analysis can be found in Hendrickson, 1985, Trans. Am. Crystallogr. Assoc., 21:11; Hendrickson et al., 1990, EMBO J. 9:1665; and Hendrickson, 1991, Science 4:91.

A fourth method of determining phase information is single wavelength anomalous dispersion or SAD. In this technique, X-ray diffraction data are collected at a single wavelength from a single native or heavy-atom derivative crystal, and phase information is extracted using anomalous scattering information from atoms such as sulfur or chlorine in the native crystal or from the heavy atoms in the heavy-atom derivative crystal. The wavelength of X-rays used to collect data for this phasing technique need not be close to the absorption edge of the anomalous scatterer. A detailed discussion of SAD analysis can be found in Brodersen et al., 2000, Acta Cryst., D56:431–441.

A fifth method of determining phase information is single isomorphous replacement with anomalous scattering or SIRAS. This technique combines isomorphous replacement and anomalous scattering techniques to provide phase information for a crystal of a polypeptide. X-ray diffraction data are collected at a single wavelength, usually from a single heavy-atom derivative crystal. Phase information obtained only from the location of the heavy atoms in a single heavy-atom derivative crystal leads to an ambiguity in the phase angle, which is resolved using anomalous scattering from the heavy atoms. Phase information is therefore extracted from both the location of the heavy atoms and from anomalous scattering of the heavy atoms. A detailed discussion of SIRAS analysis can be found in North, 1965, Acta Cryst. 18:212–216; Matthews, 1966, Acta Cryst. 20:82–86.

Once phase information is obtained, it is combined with the diffraction data to produce an electron density map, an image of the electron clouds that surround the molecules in the unit cell. The higher the resolution of the data, the more distinguishable are the features of the electron density map, e.g., amino acid side chains and the positions of carbonyl oxygen atoms in the peptide backbones, because atoms that are closer together are resolvable. A model of the macromolecule is then built into the electron density map with the aid of a computer, using as a guide all available information, such as the polypeptide sequence and the established rules of molecular structure and stereochemistry. Interpreting the electron density map is a process of finding the chemically realistic conformation that fits the map precisely.

After a model is generated, a structure is refined. Refinement is the process of minimizing the function $\Phi$, which is the difference between observed and calculated intensity values (measured by an R-factor), and which is a function of the position, temperature factor, and occupancy of each non-hydrogen atom in the model. This usually involves alternate cycles of real space refinement, i.e., calculation of electron density maps and model building, and reciprocal space refinement, i.e., computational attempts to improve the agreement between the original intensity data and intensity data generated from each successive model. Refinement ends when the function $\Phi$ converges on a minimum wherein the model fits the electron density map and is stereochemically and conformationally reasonable. During refinement, ordered solvent molecules are added to the structure.

The atomic structure coordinates and machine readable media of the invention have a variety of uses. The present invention encompasses the structure coordinates and other information, e.g., amino acid sequence, connectivity tables, vector-based representations, temperature factors, etc., used to generate the three-dimensional structures of the polypeptides for use in the software programs described below and other software programs. For example, the coordinates are useful for solving the three-dimensional X-ray diffraction and/or solution structures of other proteins, including mutant PapD-PapK chaperone-subunit or FimC-FimH chaperone-adhesin co-complexes, PapD-PapK chaperone-subunit co-complexes or FimC-FimH chaperone-adhesin co-complexes that are further associated with other molecules, and unrelated proteins, to high resolution. Structural information may also be used in a variety of molecular modeling and computer-based screening applications to, for example, intelligently design mutants of the crystallized PapD-PapK chaperone-subunit co-complex or the crystallized FimC-FimH chaperone-adhesin co-complex that have altered biological activity and to computationally design and identify compounds that bind the $G_1$ beta-strand of a periplasmic chaperone, the amino-terminal end of a pilus subunit. Such compounds may be used as lead compounds in pharmaceutical efforts to identify compounds that inhibit pilus biogenesis as a therapeutic approach toward the treatment of several types of disease caused by pathogenic Gram-negative bacteria such as *Escherichia coli*, *Haemophilus influenzae*, *Salmonella enteriditis*, *Salmonella typhimurium*, *Bordetella pertussis*, *Yersinia enterocolitica*, *Yersinia perstis*, *Helicobacter pylori* and *Klebsiella pneumoniae*.

In a further aspect of the invention, such potential antibacterial compounds are evaluated for their capacity to prevent or treat a bacterial infection. These methods comprise designing and synthesizing candidate antibacterial compounds using the atomic coordinates of the three dimensional structure of such co-crystals and screened for its ability to bind to pilus subunits thereby inhibiting or preventing pilis biogenesis. The antibacterial activity of the compound is determined by assaying the bacterium for infectivity or monitoring the pilus for activity. Such compounds which are able to prevent or inhibit pilus biogenesis or the ability of the bacterial pilus to infect a host tissue can be used in the pharmaceutical compositions of the present invention.

Additionally, the invention encompasses machine readable media embedded with the three-dimensional structures of the models described herein, or with portions thereof. As used herein, "machine readable medium" refers to any medium that can be read and accessed directly by a computer or scanner. Such media include, but are not limited to: magnetic storage media, such as floppy discs, hard disc storage medium and magnetic tape; optical storage media such as optical discs or CD-ROM; electrical storage media such as RAM or ROM; and hybrids of these categories such as magnetic/optical storage media. Such media further include paper on which is recorded a representation of the atomic structure coordinates, e.g., Cartesian coordinates, that can be read by a scanning device and converted into a three-dimensional structure with an Optical Character Recognition (OCR).

A variety of data storage structures are available to a skilled artisan for creating a computer readable medium having recorded thereon the atomic structure coordinates of the invention or portions thereof and/or X-ray diffraction data. The choice of the data storage structure will generally be based on the means chosen to access the stored information. In addition, a variety of data processor programs and formats can be used to store the sequence and X-ray data information on a computer readable medium. Such formats include, but are not limited to, Protein Data Bank ("PDB") format (Research Collaboratory for Structural Bioinformatics; Cambridge Crystallographic Data Centre format; Structure-data ("SD") file format (MDL Information Systems, Inc.; Dalby et al., 1992, J. Chem. Inf. Comp. Sci. 32:244–255), and line-notation, e.g., as used in SMILES (Weininger, 1988, J. Chem. Inf. Comp. Sci. 28:31–36). Methods of converting between various formats read by different computer software will be readily apparent to those of skill in the art, e.g., BABEL (v. 1.06, Walters & Stahl, ©1992, 1993, 1994.) All format representations of the polypeptide coordinates described herein, or portions thereof, are contemplated by the present invention. By providing computer readable medium having stored thereon the atomic coordinates of the invention, one of skill in the art can routinely access the atomic coordinates of the invention, or portions thereof, and related information for use in modeling and design programs, described in detail below.

While Cartesian coordinates are important and convenient representations of the three-dimensional structure of a polypeptide, those of skill in the art will readily recognize that other representations of the structure are also useful. Therefore, the three-dimensional structure of a polypeptide, as discussed herein, includes not only the Cartesian coordinate representation, but also all alternative representations of the three-dimensional distribution of atoms. For example, atomic coordinates may be represented as a Z-matrix, wherein a first atom of the protein is chosen, a second atom is placed at a defined distance from the first atom, a third atom is placed at a defined distance from the second atom so that it makes a defined angle with the first atom. Each subsequent atom is placed at a defined distance from a previously placed atom with a specified angle with respect to the third atom, and at a specified torsion angle with respect to a fourth atom. Atomic coordinates may also be represented as a Patterson function, wherein all interatomic vectors are drawn and are then placed with their tails at the origin. This representation is particularly useful for locating heavy atoms in a unit cell. In addition, atomic coordinates may be represented as a series of vectors having magnitude and direction and drawn from a chosen origin to each atom in the polypeptide structure. Furthermore, the positions of atoms in a three-dimensional structure may be represented as fractions of the unit cell (fractional coordinates), or in spherical polar coordinates.

Additional information, such as thermal parameters, which measure the motion of each atom in the structure, chain identifiers, which identify the particular chain of a multi-chain protein or protein co-complex in which an atom is located, and connectivity information, which indicates to which atoms a particular atom is bonded, is also useful for representing a three-dimensional molecular structure.

Uses of the Atomic Structure Coordinates

Structure information, typically in the form of the atomic structure coordinates, can be used in a variety of computational or computer-based methods to, for example, design, screen for and/or identify compounds that bind the crystallized polypeptide or a portion or fragment thereof, or to intelligently design mutants that have altered biological properties.

In one embodiment, the co-crystals and structure coordinates obtained therefrom are useful for identifying and/or designing compounds that bind PapD, PapK, FimC or FimH as an approach towards developing new therapeutic agents. For example, a high resolution X-ray structure will often show the locations of ordered solvent molecules around the protein, and in particular at or near putative binding sites on the protein. This information can then be used to design molecules that bind these sites, the compounds synthesized and tested for binding in biological assays. Travis, 1993, Science 262:1374.

In another embodiment, the structures are probed with a plurality of molecules to determine their ability to bind to PapD, PapK, FimC or FimH at various sites. Such compounds can be used as targets or leads in medicinal chemistry efforts to identify, for example, inhibitors of potential therapeutic importance.

In specific embodiments described herein, the high resolution X-ray structures of the PapD/PapK and FimC/FimH co-complexes show details of the interactions between PapD and PapK, and between FimC and FimH, respectively. This information can be used to design molecules that bind to the sites of interaction, thereby blocking co-complex formation. In addition, the X-ray structure of the FimC/FimH co-complex has a C-HEGA molecule bound in the mannose-binding pocket of FimH, which can be used to model compounds that bind to the lectin and inhibit the FimH interaction with mannose oligosaccharides on host cells.

In yet another embodiment, the structures can be used to computationally screen small molecule data bases for chemical entities or compounds that can bind in whole, or in part, to PapD, PapK, FimC or FimH. In this screening, the quality of fit of such entities or compounds to the binding site may be judged either by shape complementarity or by estimated interaction energy. Meng et al., 1992, J. Comp. Chem. 13:505–524.

The design of compounds that bind to PapD, PapK, FimC or FimH according to this invention generally involves consideration of two factors. First, the compound must be capable of physically and structurally associating with PapD, PapK, FimC or FimH. This association can be covalent or non-covalent. For example, covalent interactions may be important for designing suicide or irreversible inhibitors of a protein. Non-covalent molecular interactions important in the association of PapD with PapK or of FimC with FimH include hydrogen bonding, ionic interactions and van der Waals and hydrophobic interactions. Second, the compound must be able to assume a conformation that allows it to associate with PapD, PapK, FimC or FimH. Although certain portions of the compound will not directly participate in this association with the protein, those portions may still influence the overall conformation of the molecule. This, in turn, may have a significant impact on potency. Such conformational requirements include the overall three-dimensional structure and orientation of the chemical group or compound in relation to all or a portion of the binding site, or the spacing between functional groups of a compound comprising several chemical groups that directly interact with the protein.

The potential inhibitory or binding effect of a chemical compound on PapD, PapK, FimC or FimH may be analyzed prior to its actual synthesis and testing by the use of computer modeling techniques. If the theoretical structure of the given compound suggests insufficient interaction and association between it and the protein, synthesis and testing of the compound is unnecessary. However, if computer modeling indicates a strong interaction, the molecule may then be synthesized and tested for its ability to bind to the protein and inhibit its activity. In this manner, synthesis of ineffective compounds may be avoided.

An inhibitory or other binding compound of PapD, PapK, FimC or FimH may be computationally evaluated and designed by means of a series of steps in which chemical groups or fragments are screened and selected for their ability to associate with the individual binding pockets or interface surfaces of each of the proteins. One skilled in the art may use one of several methods to screen chemical groups or fragments for their ability to associate with PapD, PapK, FimC or FimH. This process may begin by visual inspection of, for example, the protein/protein interfaces or the mannose-binding site of FimH on the computer screen based on the PapD/PapK or FimC/FimH co-complex coordinates. Selected fragments or chemical groups may then be positioned in a variety of orientations, or docked, at an individual surface of PapD, PapK, FimC or FimH that participates in a protein/protein interface in the co-complex, or in the mannose-binding pocket of FimH, as defined supra. Docking may be accomplished using software such as QUANTA and SYBYL, followed by energy minimization and molecular dynamics with standard molecular mechanics forcefields, such as CHARMM and AMBER.

Specialized computer programs may also assist in the process of selecting fragments or chemical groups. These include:

1. GRID (Goodford, 1985, J. Med. Chem. 28:849–857). GRID is available from Oxford University, Oxford, UK;

2. MCSS (Miranker & Karplus, 1991, Proteins: Structure, Function and Genetics 11:29–34). MCSS is available from Molecular Simulations, Burlington, Mass.;

3. AUTODOCK (Goodsell & Olsen, 1990, Proteins: Structure, Function, and Genetics 8:195–202). AUTODOCK is available from Scripps Research Institute, La Jolla, Calif.; and 4. DOCK (Kuntz et al., 1982, J. Mol. Biol. 161:269–288). DOCK is available from University of California, San Francisco, Calif.

Once suitable chemical groups or fragments have been selected, they can be assembled into a single compound or inhibitor. Assembly may proceed by visual inspection of the relationship of the fragments to each other in the three-dimensional image displayed on a computer screen in relation to the structure coordinates of PapD, PapK, FimC or FimH. This would be followed by manual model building using software such as QUANTA or SYBYL.

Useful programs to aid one of skill in the art in connecting the individual chemical groups or fragments include:

1. CAVEAT (Bartlett et al., 1989, 'CAVEAT: A Program to Facilitate the Structure-Derived Design of Biologically Active Molecules'. In Molecular Recognition in Chemical and Biological Problems', Special Pub., Royal Chem. Soc. 78:182–196). CAVEAT is available from the University of California, Berkeley, Calif.;

2. 3D Database systems such as MACCS-3D (MDL Information Systems, San Leandro, Calif.). This area is reviewed in Martin, 1992, J. Med. Chem. 35:2145–2154); and 3. HOOK (available from Molecular Simulations, Burlington, Mass.).

Instead of proceeding to build an inhibitor of PapD/PapK or FimC/FimH co-complex formation, or of mannose binding to FimH, in a step-wise fashion one fragment or chemical group at a time, as described above, PapD-, PapK-, FimC- or FimH-binding compounds may be designed as a whole or 'de novo' using either an empty binding site or the surface of a protein that participates in protein/protein interactions in a co-complex, or optionally including some portion(s) of a known inhibitor(s) or of the second protein in the co-complex that participates in a particular protein/protein interaction at an interface. These methods include:

1. LUDI (Bohm, 1992, J. Comp. Aid. Molec. Design 6:61–78). LUDI is available from Molecular Simulations, Inc., San Diego, Calif.;

2. LEGEND (Nishibata & Itai, 1991, Tetrahedron 47:8985). LEGEND is available from Molecular Simulations, Burlington, Mass.; and 3. LeapFrog (available from Tripos, Inc., St. Louis, Mo.).

Other molecular modeling techniques may also be employed in accordance with this invention. See, e.g., Cohen et al., 1990, J. Med. Chem. 33:883–894. See also, Navia & Murcko, 1992, Current Opinions in Structural Biology 2:202–210.

Once a compound has been designed or selected by the above methods, the efficiency with which that compound may bind to PapD, PapK, FimC or FimH may be tested and optimized by computational evaluation. For example, a compound that has been designed or selected to function as a FimH mannose-binding inhibitor must also preferably occupy a volume not overlapping the volume occupied by the mannose-binding site residues when mannose is bound. An effective inhibitor of PapD/PapK or FimC/FimH co-complex formation, or of FimH mannose binding must preferably demonstrate a relatively small difference in energy between its bound and free states (i.e., it must have a small deformation energy of binding). Thus, the most efficient inhibitors should preferably be designed with a deformation energy of binding of not greater than about 10 kcal/mol, preferably, not greater than 7 kcal/mol. Inhibitors may interact with the protein in more than one conformation that is similar in overall binding energy. In those cases, the deformation energy of binding is taken to be the difference between the energy of the free compound and the average energy of the conformations observed when the inhibitor binds to the protein.

A compound selected or designed for binding to PapD, PapK, FimC or FimH may be further computationally optimized so that in its bound state it would preferably lack repulsive electrostatic interaction with the target protein. Such non-complementary electrostatic interactions include repulsive charge—charge, dipole—dipole and charge-dipole interactions. Specifically, the sum of all electrostatic interactions between the inhibitor and the protein when the inhibitor is bound to it preferably make a neutral or favorable contribution to the enthalpy of binding.

Specific computer software is available in the art to evaluate compound deformation energy and electrostatic interaction. Examples of programs designed for such uses include: Gaussian 92, revision C (Frisch, Gaussian, Inc., Pittsburgh, Pa. ©1992); AMBER, version 4.0 (Kollman, University of California at San Francisco, ©1994); QUANTA/CHARMM (Molecular Simulations, Inc., Burlington, Mass., ©1994); and Insight II/Discover (Biosym Technologies Inc., San Diego, Calif., ©1994). These programs may be implemented, for instance, using a computer workstation, as are well-known in the art. Other hardware systems and software packages will be known to those skilled in the art.

Once a PapD-, PapK-, FimC- or FimH-binding compound has been optimally selected or designed, as described above, substitutions may then be made in some of its atoms or chemical groups in order to improve or modify its binding properties. Generally, initial substitutions are conservative, i.e., the replacement group will have approximately the same size, shape, hydrophobicity and charge as the original group. One of skill in the art will understand that substitutions known in the art to alter conformation should be avoided. Such altered chemical compounds may then be analyzed for efficiency of binding to PapD, PapK, FimC or FimH by the same computer methods described in detail above.

Because PapD/PapK co-complexes may crystallize in more than one crystal form, the structure coordinates of PapD/PapK co-complex, of PapD alone, of PapK alone, or of portions thereof, are particularly useful to solve the structure of those other co-crystal forms of PapD/PapK co-complex. They may also be used to solve the structure of mutants, of PapD/PapK co-complex further complexed to another molecule, or of the crystalline form of any other protein or protein co-complex with significant amino acid sequence homology to any functional domain of PapD or PapK. Similarly, the structure coordinates of FimC/FimH co-complex, of FimC alone, of FimH alone, or of portions thereof, are particularly useful to solve the structure of other co-crystal forms of FimC/FimH co-complex. They may also be used to solve the structure of mutants, of FimC/FimH co-complex further complexed to another molecule, or of the crystalline form of any other protein or protein co-complex with significant amino acid sequence homology to any functional domain of FimC or FimH.

One method that may be employed for this purpose is molecular replacement. In this method, the unknown co-crystal structure, whether it is another co-crystal form of a PapD/PapK or FimC/FimH co-complex, a mutant, a PapD/PapK or FimC/FimH co-complex that is further complexed to another molecule, or the crystal of some other protein or protein co-complex with significant amino acid sequence homology to any functional domain of one of the proteins in the co-complex crystal, may be determined using phase information from the PapD/PapK or FimC/FimH structure coordinates, respectively. This method will provide an accurate three-dimensional structure for the unknown protein or protein co-complex in the new crystal more quickly and efficiently than attempting to determine such information ab initio.

If an unknown crystal form has the same space group as and similar cell dimensions to the known co-complex crystal form, then the phases derived from the known crystal form can be directly applied to the unknown crystal form, and in turn, an electron density map for the unknown crystal form can be calculated. Difference electron density maps can then be used to examine the differences between the unknown crystal form and the known crystal form. A difference electron density map is a subtraction of one electron density map, e.g., that derived from the known crystal form, from another electron density map, e.g., that derived from the unknown crystal form. Therefore, all similar features of the two electron density maps are eliminated in the subtraction and only the differences between the two structures remain. For example, if the unknown crystal form is of a FimC/FimH co-complex that is further complexed with a mannose analog in the FimH mannose binding site, then a difference electron density map between this map and the map derived from the native, uncomplexed crystal will ideally show only the electron density of the differences between C-HEGA and the mannose analog. Similarly, if amino acid side chains have different conformations in the two crystal forms, then those differences will be highlighted by peaks (positive electron density) and valleys (negative electron density) in the difference electron density map, making the differences between the two crystal forms easy to detect. However, if the space groups and/or cell dimensions of the two crystal forms are different, then this approach will not work and molecular replacement must be used in order to derive phases for the unknown crystal form.

All of the complexes referred to above may be studied using well-known X-ray diffraction techniques and may be refined versus 1.5 Å or higher to 3 Å resolution X-ray date to an R value of about 0.20 or less using computer software, such as X-PLOR (Yale University, (c) 1992, distributed by Molecular Simulations, Inc.). See, e.g., Blundel et al., 1976, Protein Crystallography, Academic Press.; Methods in Enzymology, vol. 114 & 115, Wyckoff et al., eds., Academic Press, 1985. This information may thus be used to optimize known classes of inhibitors of PapD/PapK or FimC/FimH co-complex formation or of mannose binding to FimH, and more importantly, to design and synthesize novel classes of inhibitors of PapD/PapK or FimC/FimH co-complex formation or of mannose binding to FimH.

The structure coordinates of PapD/PapK or FimC/FimH mutant co-complexes will also facilitate the identification of related protein co-complexes analogous to the PapD/PapK or FimC/FimH co-complexes in function, structure or both, thereby further leading to novel therapeutic modes for treating or preventing gram-negative bacteria-mediated diseases.

Subsets of the atomic structure coordinates can be used in any of the above methods. Particularly useful subsets of the coordinates include, but are not limited to, coordinates of single domains, coordinates of residues lining an active site, coordinates of residues that participate in important protein—protein contacts at an interface, and $C_\alpha$ coordinates. For example, the coordinates of one domain of a protein that contains the active site may be used to design inhibitors that bind to that site, even though the protein is fully described by a larger set of atomic coordinates. Therefore, as described in detail for the specific embodiments, below, a set of atomic coordinates that define the entire polypeptide chain, although useful for many applications, do not necessarily need to be used for the methods described herein.

Uses of Subsets of Atomic Coordinates in Specific Embodiments

The structure coordinates of the present invention, and subsets thereof, are useful for designing or screening for compounds that bind to the PapD, PapK, FimC or FimH proteins. The high resolution X-ray structures of the PapD/PapK and FimC/FimH co-complexes of the present invention show details of the interactions between PapD and PapK, and between FimC and FimH, respectively. This information can be used to design and/or screen for compounds that bind to the sites of interaction, thereby blocking co-complex formation and pilus assembly. In addition, the X-ray structure of the FimC/FimH co-complex has a C-HEGA molecule bound in the mannose-binding pocket of FimH, which can be used to model compounds that bind to the lectin domain and inhibit the FimH interaction with mannose on host cells.

Those of skill in the art will recognize that the complete set of PapD/PapK co-complex structure coordinates and the complete set of FimC/FimH co-complex structure coordinates will be useful in the methods of the present invention. Those of skill in the art will further recognize that the coordinates of PapD, PapK, FimC and FimH will be useful separate from the coordinates of the protein with which each protein forms a co-complex in the crystals. In addition, those of skill in the art will recognize that subsets of the structure coordinates of each protein, such as the coordinates of a single domain or interface or binding pocket, will be useful in the methods of the invention, as discussed in more detail, below.

In one embodiment, the PapK coordinates, or the subset of PapK coordinates that are the residues in the hydrophobic groove region of PapK (the K1 region), where the $G_1$ beta-strand of PapD interacts with PapK in the co-complex crystal structure, are useful for designing and/or screening for compounds that bind in the groove in order to prevent pilus assembly. A subset of structure coordinates of PapK useful in this embodiment of the invention include those of $Val^{16K}$, $Leu^{21K}$, $Val^{26K}$, $Phe^{27K}$, $Phe^{47K}$, $Ile^{49K}$, $Phe^{67K}$, $Ile^{91K}$, $Ile^{93K}$, $Tyr^{146K}$, $Ala^{150K}$, $Thr^{151K}$, $Phe^{152K}$, $Leu^{154K}$ and $Tyr^{156K}$, as numbered in FIG. 3.

In another embodiment, the PapD coordinates, or the subset of PapD coordinates that are the $G_1$ beta-strand residues (the D1 region), which interacts with the K1 region by fitting into the hydrophobic groove of PapK in the PapD/PapK co-complex structure, are useful for designing compounds that have an analogous shape, such that the compounds fit into the PapK groove and inhibit pilus assembly. A subset of $G_1$ beta-strand structure coordinates of PapD useful in this embodiment include those of $Leu^{103D}$, $Gln^{104D}$, $Ile^{105D}$, $Ala^{106D}$ and $Leu^{107D}$.

In yet another embodiment, the PapD coordinates, or a subset of PapD coordinates in the D2 region, and the PapK coordinates, or a subset of PapK coordinates in the K2 region, which participate in a second interface of the PapD/PapK co-complex, are useful for designing and/or screening for compounds that disrupt this interaction and prevent PapD-PapK co-complex formation. A subset of PapK coordinates useful for this embodiment of the invention include those of residues $Val^{59K}$, $Gly^{60K}$, $Ly^{61K}$ and $Arg^{157K}$. A subset of PapD coordinates useful for this embodiment of the invention include those of residues $Thr^{152D}$, $Ile^{154D}$, $Glu^{164D}$, $Glu^{165D}$, $Thr^{170D}$, $Ile^{94D}$ and $Arg^{200D}$.

In another embodiment, the FimH coordinates, a subset of the FimH coordinates that are the pilin domain of FimH, or a subset of FimH coordinates that are the residues in the hydrophobic groove region of the pilin domain, where the $G_1$ beta-strand of FimC interacts with FimH, are useful for designing and/or screening for compounds that inhibit this interaction, thereby inhibiting pilus formation in type 1 pili. A subset of FimH structure coordinates useful in this embodiment of the invention include those of residues $Ala^{150H}$, $Asn^{152H}$, $Val^{154H}$ and $Val^{156H}$, as numbered in FIG. 8.

In yet another embodiment, the FimC coordinates, or a subset of FimC coordinates that are the residues of the $G_1$ beta-strand that interact with the hydrophobic groove region of FimH are useful for designing compounds that have an analogous shape, such that the compounds fit into the FimH groove and inhibit type 1 pilus assembly. A subset of FimC structure coordinates useful in this embodiment of the invention include those of residues $Ile^{103C}$, $Leu^{105C}$ and $Ile^{107C}$.

In another embodiment, the FimH coordinates, a subset of FimH coordinates that are the lectin domain of FimH, or a subset of FimH coordinates that comprise the mannose binding pocket of the lectin domain are useful for designing and/or screening for compounds that fit into the mannose binding pocket and block the interaction of FimH with host cell mannose oligosaccharides, thus preventing adhesion to host cells and *E. coli* pathogenesis. A subset of structure coordinates useful in this embodiment of the invention include those of residues $Phe^{1H}$, $Asn^{46H}$, $ASP^{47H}$, $Tyr^{48H}$, $Ile^{52H}$, $Asp^{54H}$, $Gln^{133H}$, $Asn^{135H}$, $Tyr^{137H}$, $Asn^{138H}$, $Asp^{140H}$ and $Phe^{142H}$.

The following examples illustrate the invention, but are not to be taken as limiting the various aspects of the invention so illustrated.

EXAMPLES

Example 1

The PapD-PapK Chaperone-Subunit Co-Complex

Expression of the PapD-PapK Co-Complex. The PapD-PapK co-complex was overexpressed in *E. coli* and periplasms were prepared as described by Slonim et al. (*EMBO J.* 1992, 11:4747). Periplasms were then subjected to cation exchange (15S Source (Pharmacia)) followed by hydrophobic interaction (15PHE Source (Pharmacia)) chromatography to yield pure co-complex. Expression of selenomethionine (Se-Met) PapD-PapK co-complexes was carried out in the *E. coli* methionine-auxotroph DL41 strain as described by Hendrickson et al. (*EMBO J.* 1990, 9:1665) and purified as was the wild-type co-complex. The purified wild-type or Se-Met PapD-PapK co-complexes were dialyzed against 20 mM KMES pH 6.7 and concentrated to ~12 mg/ml. Co-crystals were grown by vapor diffusion using the hanging drop method against a reservoir containing 10–15% (w/v) PEG 6000, 100 mM potassium acetate, and 200–400 mM sodium acetate at pH 4.6 [A. McPherson, *Eur. J. Biochem.* 189, 23 (1990)] and appeared within three to five days. The co-crystals were cryoprotected by increasing the concentration of PEG 6000 to 25% (w/v) and flash-cooled to liquid nitrogen temperature. Co-crystals were in space group $P2_12_12_1$, with cell dimension a=62.12±2.02 Å, b=63.69±+0.2 Å, and c=92.72±0.2 Å, and with one co-complex in the asymmetric unit. Table 4 contains a summary of the data collected and refinement statistics.

TABLE 4

Data collection and refinement statistics of PapD-PapK Co-complex

| | | Data Collection | | | | |
|---|---|---|---|---|---|---|
| Data Set | Radiation | Resolution | Total/Unique reflections | Completeness (%)* | $R_{sym}$ (%)† | $R_{iso}$ (%)‡ |
| Native | CuKα, Raxis | 30 to 2.7 Å | 22,046/8,960 | 84.5 (77.2) | 6.4 (14.5) | |
| SeMet-single | CuKα, Raxis | 30 to 2.5 Å | 46,683/12,179 | 90.4 (75.2) | 6.9 (19.2) | 8.5 |
| SeMet-1 | 0.9879 Å, X4A | 30 to 2.4 Å | 92,857/14,135 | 89.4 (79.1) | 6.0 (13.9) | |
| SeMet-2 | 0.9792 Å, X4A | 30 to 2.4 Å | 105,506/14,343 | 92.9 (83.2) | 6.1 (14.1) | |
| SeMet-3 | 0.9788 Å, X4A | 30 to 2.4 Å | 102,568/14,203 | 91.5 (79.4) | 6.4 (14.6) | |
| SeMet-4 | 0.9667 Å, X4A | 30 to 2.4 Å | 102,187/14,314 | 92.5 (82.4) | 6.3 (15.0) | |
| Figure of merit for MAD phasing SeMet-1-4 data (calculated for 30 to 2.4 Å) | | | | | 0.49 | |

TABLE 4-continued

Data collection and refinement statistics of PapD-PapK Co-complex

| | | | Refinement | | | | |
|---|---|---|---|---|---|---|---|
| | Number of | Total Number | R Factor/$R_{free}$ | | rms deviations¶ | | |
| Resolution (Å) | Reflections § | of Atoms | (%)‖ | Bonds (Å) | Angles (°) | B values (Å²) | |
| 30.0 to 2.4 | 12,678 (84.8%/77.3%) | 2912# | 23.8/27.4 | 0.011 | 1.45 | 1.62 (main chain) | 2.20 (side chain) |

*Completeness for $I/\sigma(I) > 1.0$, high-resolution shell in parentheses [2.80 to 2.70 Å (native), 2.59 to 2.50 Å (SeMet-single), 2.50 to 2.40 Å (MAD)].
†$R_{sym} = \Sigma|I - <I>|/\Sigma I$, where $I$ = observed intensity, and $<I>$ = average intensity from multiple observations of symmetry-related reflections; high-resolution shell in parentheses.
‡$R_{iso} = \Sigma||F_{PH}| - |F_P||/\Sigma|F_P|$, where $F_p$ = native structure factor amplitude and $F_{PH}$ = derivative (SeMet) structure factor amplitude.
§Numbers reflect the "working set" of reflections at $F/\sigma(F) > 2.0$, overall/last shell (2.51 to 2.40 Å) completeness in parentheses.
‖$R_{free}$ was calculated on the basis of 7.0% of the total number of reflections randomly omitted from the refinement.
¶eviations from ideal bond lengths and angles and in B factors of bonded atoms.
Including 104 water molecules.

A complete data set to a resolution of 2.7 Å was collected in the laboratory setting (Rigaku Raxis IV image plate mounted on a Rigaku RU200 rotating anode X-ray generator) using an oscillation range of 1.5° and exposure time of 45 mm/frame ("Native" data set in Table 4). Se-Met PapD-PapK co-crystals were in the same space group with the same cell dimensions. Once cooled, these co-crystals diffracted to slightly higher resolution in the laboratory setting and a complete data set ("Se-Met Single" in Table 4) to a resolution of 2.5 Å was collected (2.5E oscillation range, 60 mm/frame). These co-crystals were also used to collect MAD data at the National Synchrotron Light Source at Brookhaven National Laboratory (Beamline X4A). Complete data sets at four wavelengths to a resolution of 2.4 Å were collected ("Se-Met1-4" in Table 4). All data were reduced and processed using the programs DENZO and SCALEPACK [Z. Otwinoski, in Proceedings of the CCP4 Study Weekend, L. Sawyers, N. Isaacs, S. Bailey, Eds. (SERC Daresbury Laboratory, Warrington, 1993), pp. 56–62].

Figure 1B:
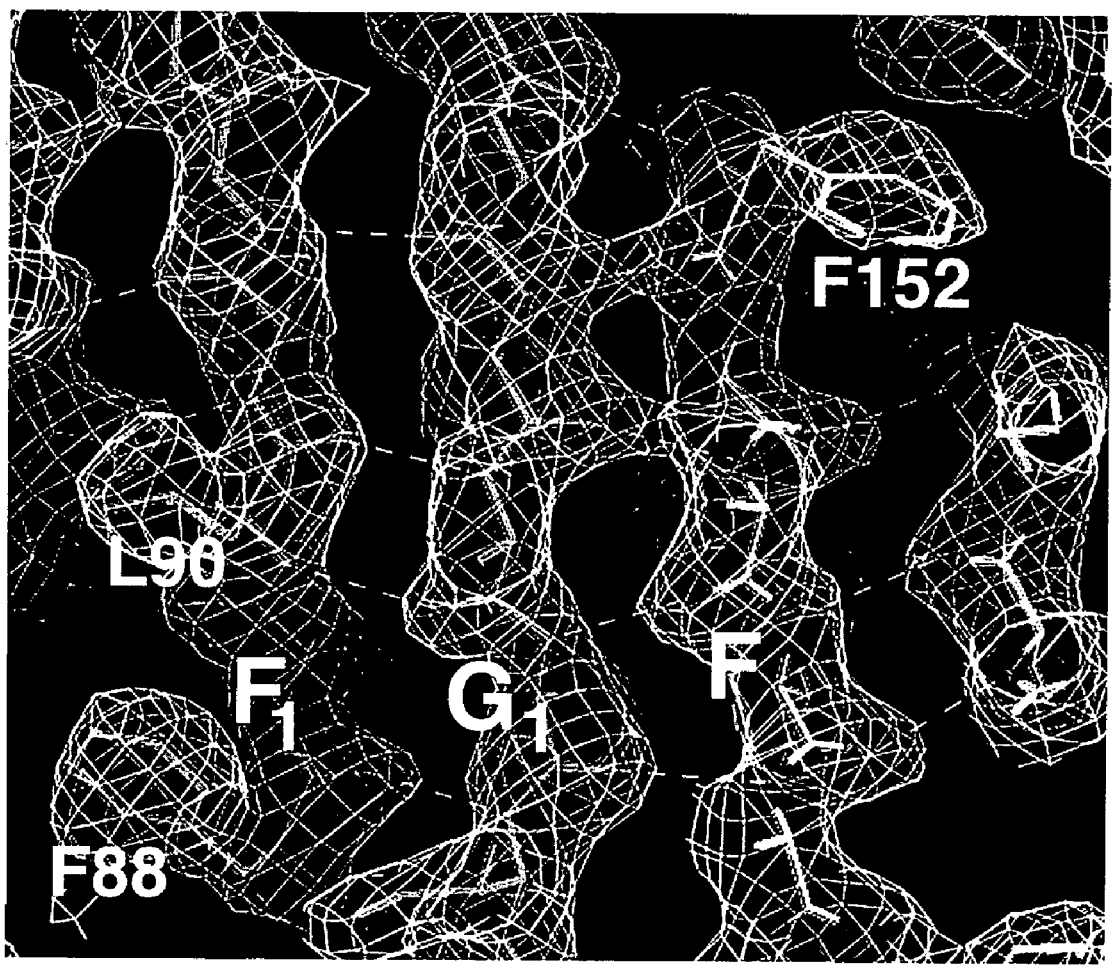
FIG. 1B is a depiction of representative regions of electron density shown in PapD $G_1$ beta-strand zippering to the PapK F strand. The density is from a map calculated using unbiased experimental MAD solvent-flattened phases.
Figure 1C:
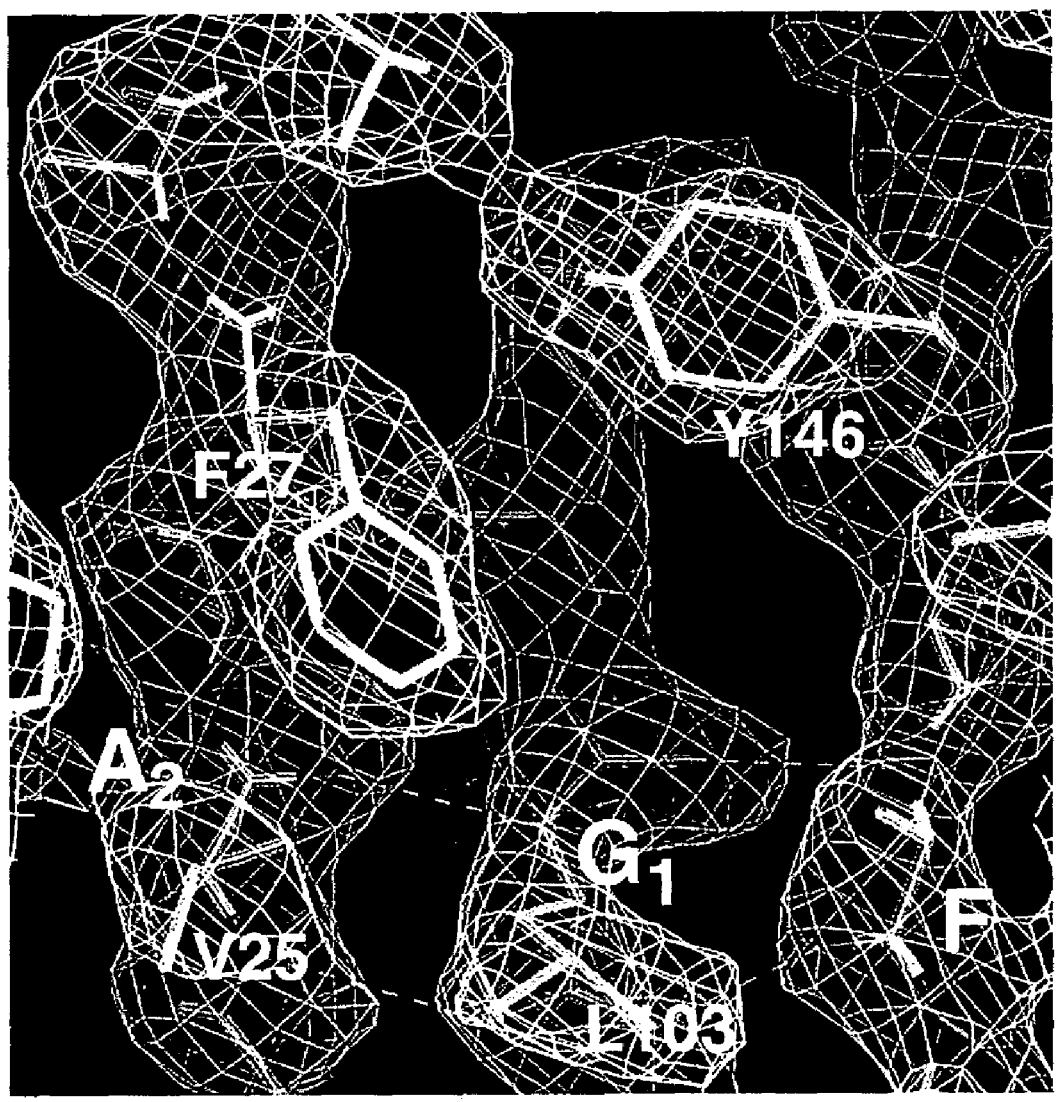
FIG. 1C is a view from the hydrophobic core of PapK looking out toward the PapD $G_1$ beta-strand that inserts into the groove of the subunit. Residues throughout are labeled. The density is from a map calculated using unbiased experimental MAD solvent-flattened phases.

Structure of PapD-PapK co-complex. The structure of the PapD-PapK co-complex was solved using MAD phasing [W. A. Hendrickson, Science 254, 51 (1991)]. The PapD-PapK co-complex contains three methionines, all of which are in PapD, at positions 18, 66, and 172. The "Native" and "Se-Met Single" data sets were first used to generate a difference Patterson map using the program HEAVY [T. C. Terwilliger and D. Eisenberg, Acta Crystalldgr. A39, 813 (1983)] where strong peaks could be readily located. Three heavy metal positions were determined using the program HASSP [T. C. Terwilliger, S.-H. Kim, D. Eisenberg, Acta Crystallogr. A43, 1 (1987)]. Initial SIRAS-solvent flattened phases were, however, insufficient to build a model of PapK Subsequently, multi-wavelength anomalous diffraction (MAD) data were collected (Table 4). After local scaling using the high energy remote wavelength ("SeMet-4" in Table 4) as the reference wavelength, MAD phases were calculated using SHARP [E. De La Fortelle and G. Bricogne, Methods Enzymol. 276, 472 (1997)]. An interpretable electron density map was readily obtained after density modification by solvent flipping (program SOLOMON [J. P. Abrahams and A. G. W. Leslie, Acta Crystallogr. D52, 32 (1996)]). The PapD subunit was rebuilt into the experimental electron density, starting from the apo-PapD structure. A $C_V$ trace of the PapK subunit was built into the experimental electron density map using program O [T. A. Jones and S. Thirup, EMBO J. 5, 819 (1986); T. A. Jones, J. Y. Zou, S. W. Cowan, M. Kjeldgaard, Acta Crystallogr. A47, 110 (1991)], accounting for all but 8 residues located at the $NH_2$-terminus, for which, even at later stages of the refinement, no electron density was observed. The electron density was of sufficient quality (FIG. 1) to unequivocally assign the sequence. The model was then refined using CNSsolve 0.5 [A. T. Brünger et al., Acta Cystallogr. D54, 905 (1998)] against the 'SeMet-3' structure factor amplitudes using the maximum likelihood refinement target with incorporation of experimental phase information [P. D. Adams, N. S. Pannu, R. J. Read, A. T. Brünger, Proc. Natl. Acad. Sci. 94, 5018 (1997); N. S. Pannu, G. N. Murshudov, E. J. Dodson, R. J. Read, Acta Crystallogr. D54, 1258 (1998)]. Both positional and simulated annealing refinement in cartesian space were used (the temperature factors were set to 25 Å²) and resulted in values of R- and free-R of 27.4 and 32.5%, respectively [A. T. Brünger, J. Mol. Biol. 203, 803 (1988)]. After two rounds of rebuilding, where simulated annealing omit maps were generated for ambiguous regions and used to adjust the model [A. Hodel, S.-H. Kim, A. T. Brünger, Acta Crystallogr. A48, 851 (1992)], positional refinement followed by restrained refinement of the temperature factors resulted in a model with R and free-R values of 24.3 and 28.8%, respectively. At this stage, 104 well-defined water molecules were added resulting in a final model with R- and free-R values of 23.8% and 27.4%, respectively. The stereochemistry of the model is excellent and the temperature factors restrained appropriately (Table 4). The model of PapK is complete between residues 9 and 157. Electron density was poor for residues 216 to 218 of PapD and therefore, this region was not included in the final model. Also, for the same reason, residues Arg[96] and Glu[98] in PapD were built as alanines. All residues in PapK and PapD are located in either the most favored or the allowed regions of the Ramachandran plot [G. N. Ramachandran and V. Sasisekharan, Adv. Protein Chem. 23, 283 (1968)]. Coordinates have been deposited at the Protein Data Bank (entry code 1PDK).

Figure 2A:
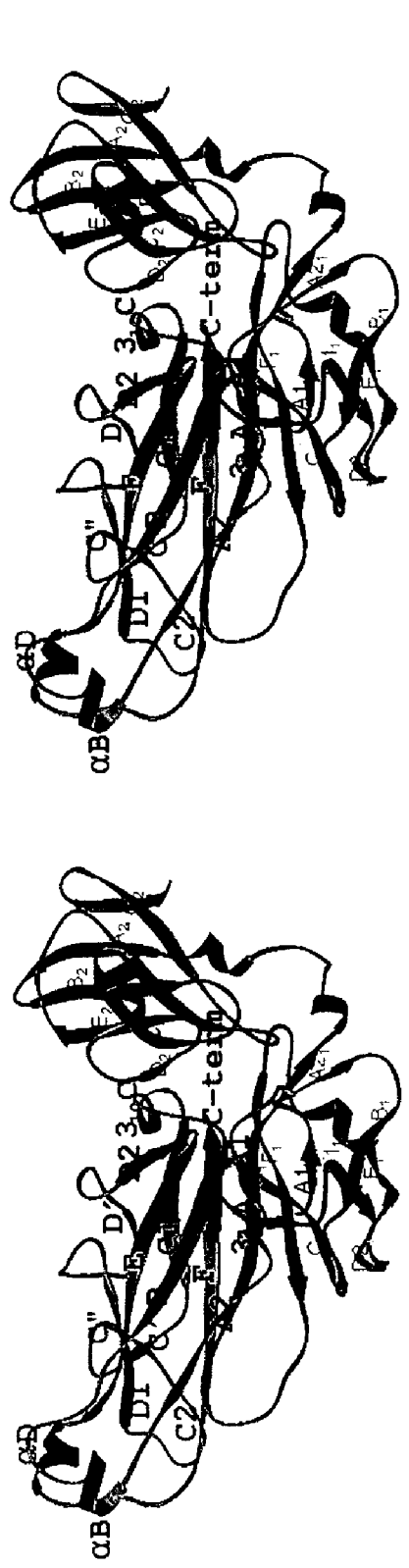
FIG. 2A is a schematic of a stereo ribbon diagram. Subscripts 1 and 2 refer to domains 1 and 2 of PapD, respectively.
Figure 2B:
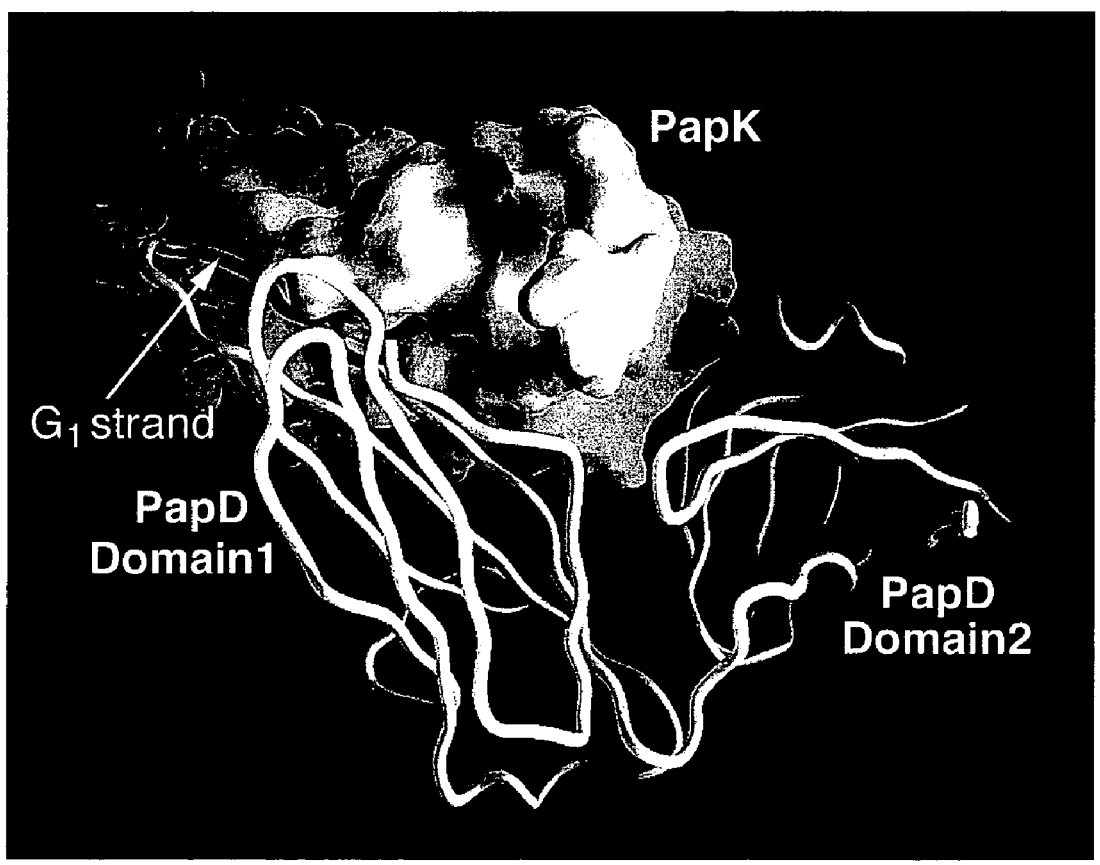
FIG. 2B is a stereo ribbon diagram. The molecular surface of PapK, calculated and displayed using GRASP. The structure of PapD is shown as a ribbon. The insertion of the $G_1$ beta-strand of PapD into a deep groove on the surface of PapK can be seen.
Figure 3A:
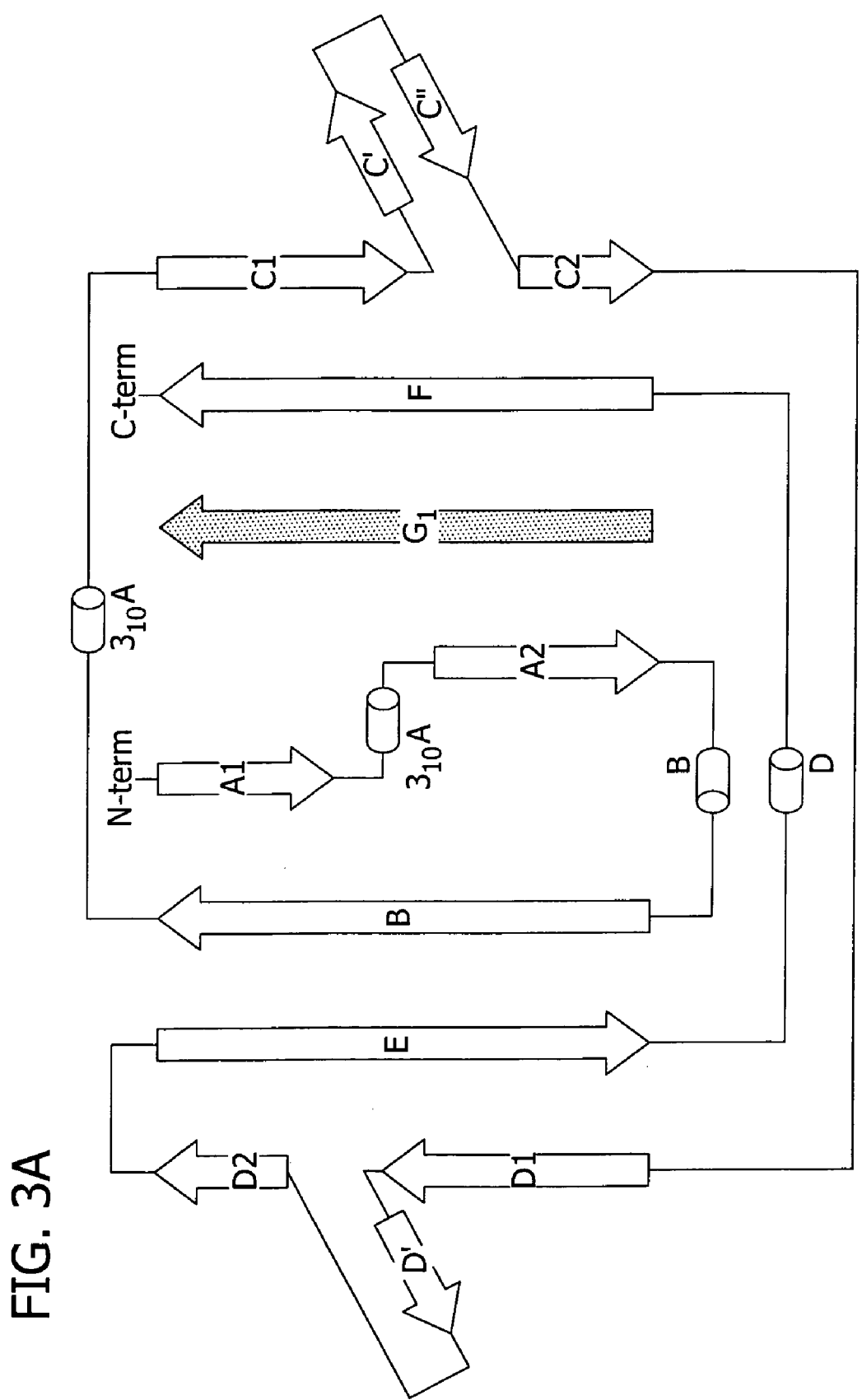
FIG. 3A is the topology of PapK. Beta-strands are indicated as arrows, while helices (either α or $3_{10}$) are shown as cylinders.
Figure 3B:
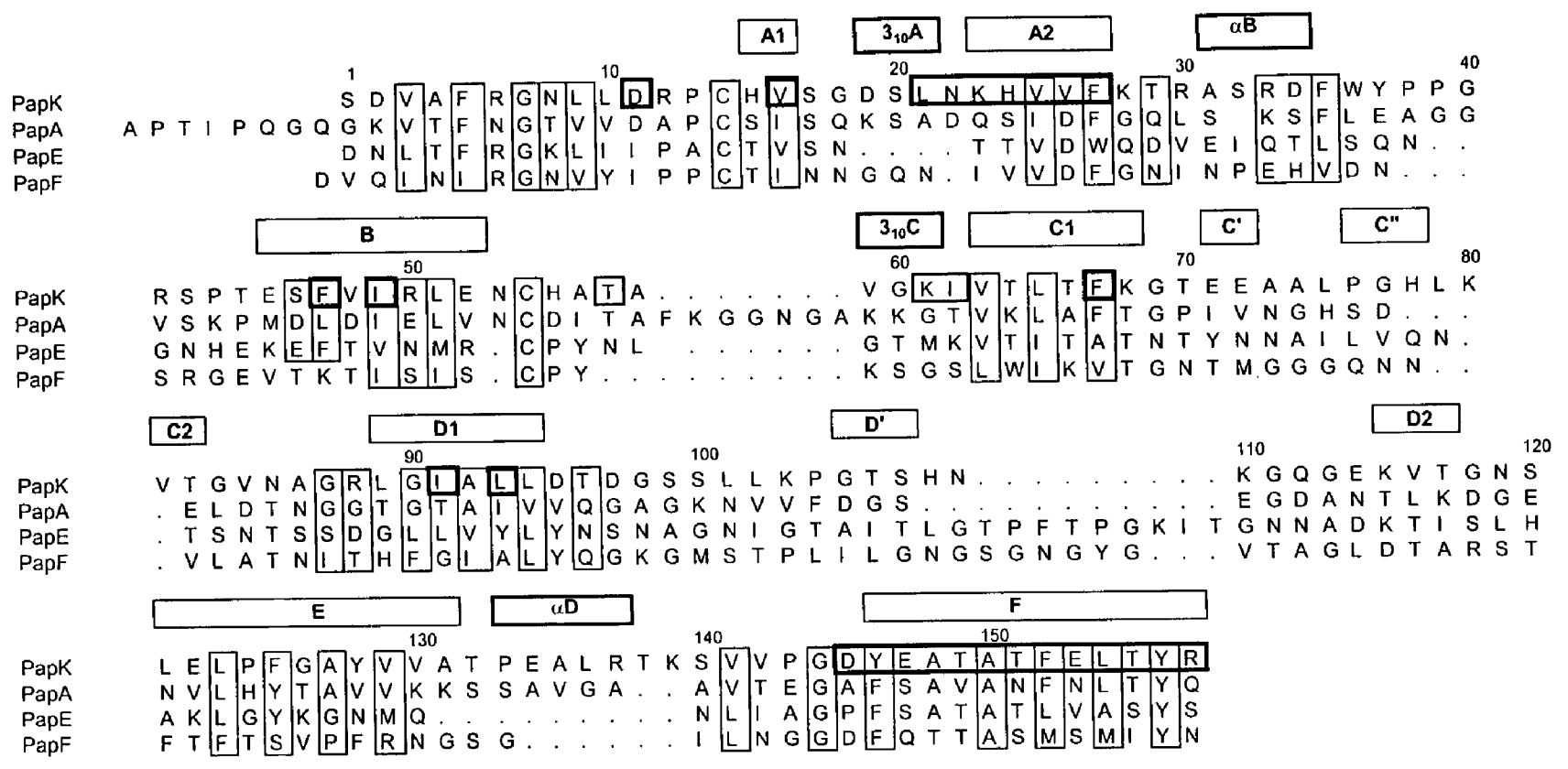
Figure 3C:
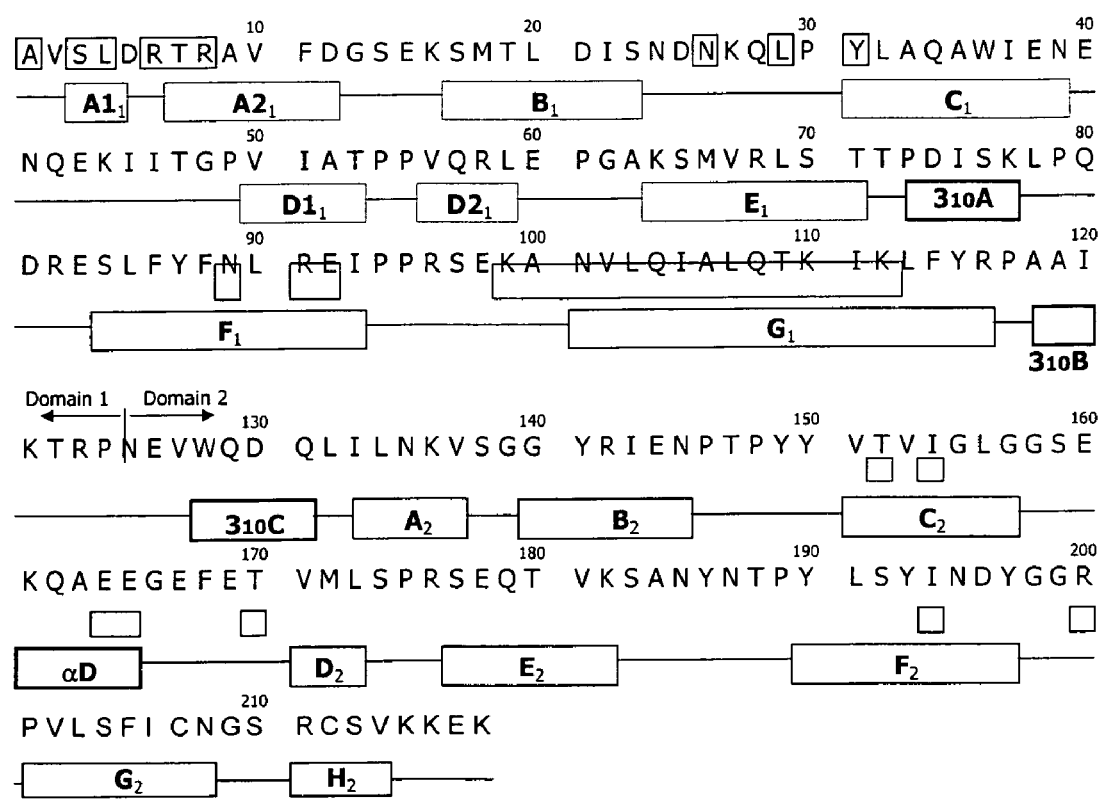
FIG. 3C is a depiction of the secondary structure definition of PapD (Seq. ID No: 61). Residue numbers are indicated above the sequence, while secondary structural elements are indicated below it.

COOH-terminally truncated Ig fold of PapK. PapK has the same overall variable-region immunoglobin-like (Ig) fold as the amino-terminal domain of PapD, with two beta-sheets coming together in a beta-sandwich (FIGS. 2A and 3A; see also FIG. 2A for secondary structure notation). However, the Ig fold of PapK is incomplete: it lacks the COOH-terminal seventh strand, G, which in canonical Ig folds forms an antiparallel beta-sheet interaction with strand F and contributes to the hydrophobic core of the protein. Remarkably, in the PapD-PapK co-complex, this missing strand is provided by PapD, which donates its $G_1$ beta-strand to complete the Ig fold of PapK (FIGS. 2A, 2B, and 3A). The Ig fold thus produced is however atypical, since the donated strand runs parallel, rather than antiparallel, to strand F in PapK. The insertion of the $G_1$ beta-strand into the fold of the pilin, coined as "donor strand complementation" has important implications for the mechanisms of subunit folding, capping and assembly.

The first eight $NH_2$-terminal residues of PapK are disordered. The Ig fold of PapK (FIG. 3A) begins with a short beta-strand, A1, which makes typical antiparallel hydrogen bonds with the COOH-terminal residues of strand B. This short beta-sheet arrangement is interrupted by the insertion of a $3_{10}$ helical turn (FIGS. 2A and 3B) which results in strand A switching sides in the beta-sandwich in order to make antiparallel beta-strand interactions with the $G_1$ beta-strand of the chaperone (FIG. 3A). Strands A and B are connected by a short α-helix (αB in FIGS. 2A and 3B) which precedes three successive aromatic residues ($Phe^{35}$, $Trp^{36}$, $Tyr^{37}$, FIG. 3B). While $Phe^{35}$ inserts into the hydrophobic core of the beta-sandwich, $Trp^{36}$ and $Tyr^{37}$ interact closely with residues at the COOH-terminus of helix αD (FIG. 2A), possibly contributing to its stability. Strand B forms the edge of one of the two beta-sheets in the beta-sandwich and runs antiparallel to strand E. Following strand B, the structure crosses over to the other side of the beta-sandwich through a short $3_{10}$ helix (FIG. 2A) to form strand C1, which runs antiparallel to strand F. The COOH-terminus of strand C1 deviates from the beta-sheet arrangement to form a protruding beta-meander (strands C' and C"). Strand C" reaches over to the other side of the beta-sandwich to form main-chain hydrogen bonds with strand D1. This small beta-structure eventually returns, as C2, to make main-chain hydrogen bonding interactions with strand F (FIGS. 2A, 3A, and 3B).

An extended loop links strand C to strand D1 on the other side of the beta-sandwich. Strand D constitutes an edge of the D, E, B, A1 beta-sheet. It therefore runs antiparallel to strand E. However, strand D is divided in the middle by an insertion which meanders towards the C', C" meander and reaches back to the E strand. Strand E is followed by a three-turn helix (αD) and a long loop structure which connects it to the COOH-terminal strand F. Finally, strand F, from $Asp^{145}$ onward, forms a parallel beta-sheet with strand $G_1$ of PapD (FIGS. 2A and 3A). Hence, strand $G_1$ of PapD is an integral part of the C, F, A2 beta-sheet of PapK.

Figure 4:
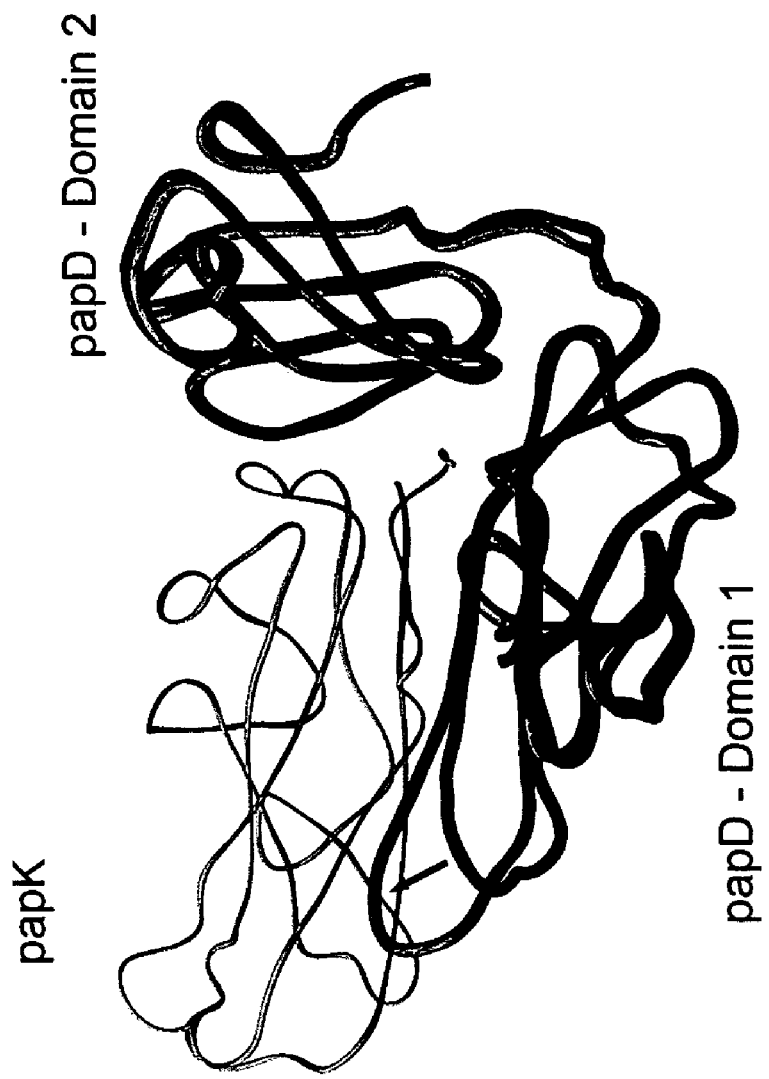
FIG. 4 depicts the superposition of the structures of apo-PapD and PapD complexed to PapK. The arrow indicates the conformational change in the $F_1$–$G_1$ loop upon subunit binding.

Structure of PapD in the PapD-PapK Co-complex. Except for the $F_1$–$G_1$ loop in the $NH_2$-terminal domain (FIGS. 3C and 4), the structure of PapD in the PapD-PapK co-complex superimposes very well with apo PapD (r.m.s. deviation in Cα atom positions, excluding the $F_1$–$G_1$ loop, of 0.65 Å). Hence, the binding of PapK does not alter the orientation of the domains of PapD. The major difference between the apo and PapK-bound forms of PapD is a large conformational change in the $F_1$–$G_1$ loop of PapD. The tip of this loop undergoes a flap motion of about 11 Å that results in an re-ordering of the $F_1$–$G_1$ loop such that residues 101 to 105 of PapD become part of the $G_1$ beta-strand.

Figure 5:
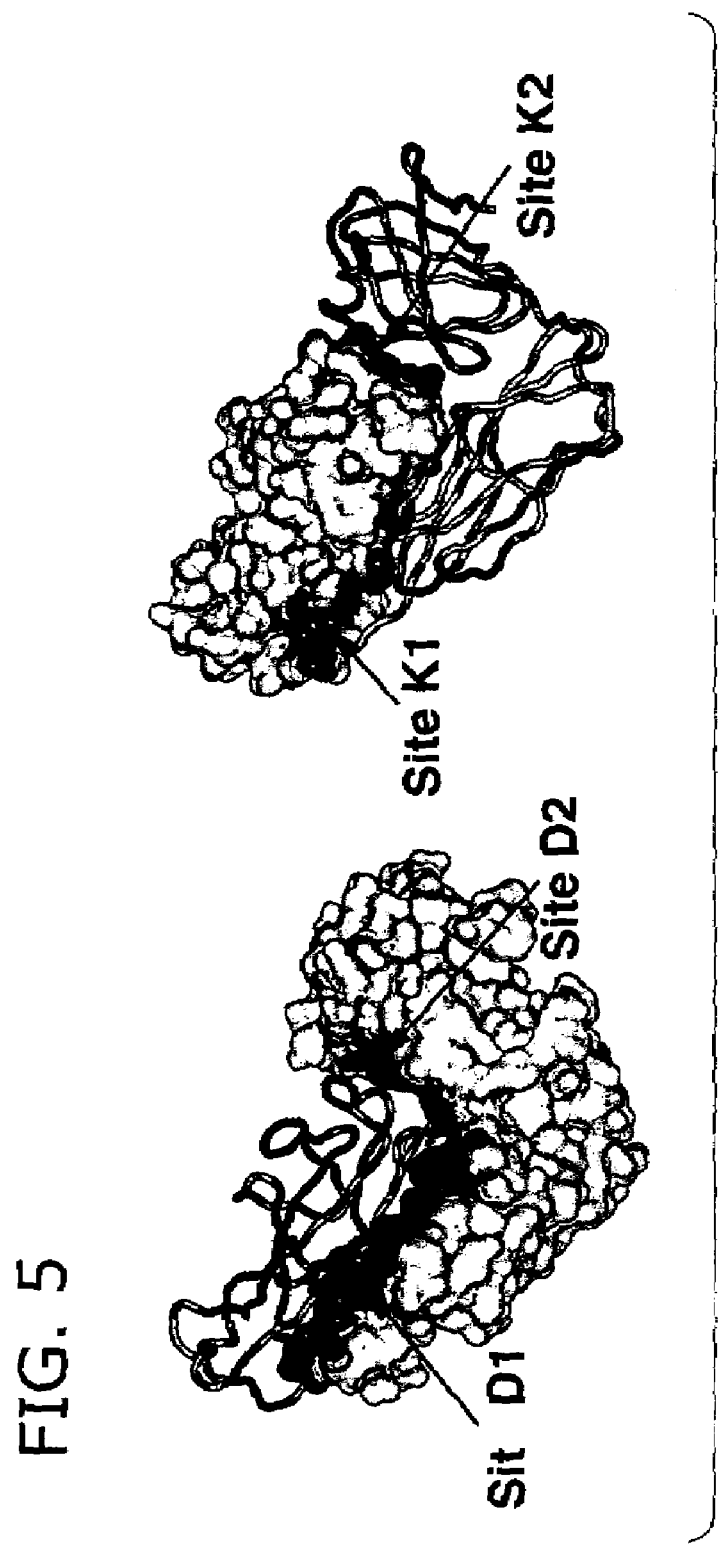
FIG. 5 is the definition of the binding sites in PapD and PapK. On the left, PapD is shown as a space-filling model and PapK as a ribbon. On the right, PapK is shown as a space-filling model and PapD as a ribbon. The various binding sites as defined in the text are labeled.

The PapD-PapK interface. The total buried surface area in the PapD-PapK co-complex is 3434 $A^2$. There are two distinct sites on PapK that interact with two corresponding sites on PapD. Site K1 of PapK interacts with a site on the $NH_2$-terminal domain (domain 1) of PapD (site D1) and site K2 of PapK interacts with a site on the COOH-terminal domain (domain 2) of PapD (site D2) (FIG. 5).

Figure 6A:
FIG. 6A is a schematic of a stereo contact diagram of interactions between PapD and the $NH_2$-terminus of PapK. Residues making contacts are shown in stick representation (thin for PapD, and thick for PapK).
Figure 6B:
FIG. 6B is a schematic of a stereo contact diagram of interactions between PapD and the COOH-terminal F strand of PapK. The $NH_2$-terminal strand A and the COOH-terminal strand F form the sides of the groove in PapK. Residues making contacts are shown in stick representation (thin for PapD, and thick for PapK).

Site K1 contains a deep groove which runs the length of the subunit. The edges of the groove consist of strands A and F and its base is formed by the hydrophobic core of PapK (FIGS. 6A, 6B and 6E). This groove is the result of the missing G beta-strand in the Ig fold of PapK. Site D1 includes residues 101 to 112 of the $G_1$ beta-strand of PapD, which insert into the $K_1$ groove and make a beta-zipper interaction with strand F of PapK on one side of the groove. Residues 101 to 105 also make a beta-zipper interaction with strand A2 on the other side of the groove (FIGS. 6A and 6B). Insertion of the $G_1$ beta-strand also results in the formation of a continuous 5-stranded beta-sheet which includes strands $C_1$, $F_1$, and $G_1$ of PapD and F and C1 of PapK (FIG. 2A). The alternating hydrophobic residues in the $G_1$ beta-strand of PapD ($Leu^{103}$, $Ile^{105}$, and $Leu^{107}$) interact with the hydrophobic base of the groove (FIG. 6E). Thus the donor strand complementation by the $G_1$ beta-strand of PapD shields the hydrophobic core of the pilin from exposure to the aqueous milieu of the periplasm.

The K1-D1 interaction also involves contacts at the end of the groove nearest the cleft of the chaperone. These interactions consist of hydrophobic and polar contacts between the A1 strand of PapK and the $A1_1$, $A2_1$ and $C_1$ strands of PapD (FIGS. 6A and 6B). The COOH-terminal carboxylate of PapK anchors the subunit into the cleft of PapD by hydrogen bonding to the invariant $Arg^8$ and $Lys^{112}$ residues of PapD as well as to the Oγ hydroxyl of highly conserved $Thr^{152}$ (FIGS. 6C and 6D).

Figure 6C:
FIG. 6C is a schematic of a stereo contact diagram of interactions between PapK and domain 2 of PapD. Residues making contacts are shown in stick representation (thin for PapD, and thick for PapK).
Figure 6D:
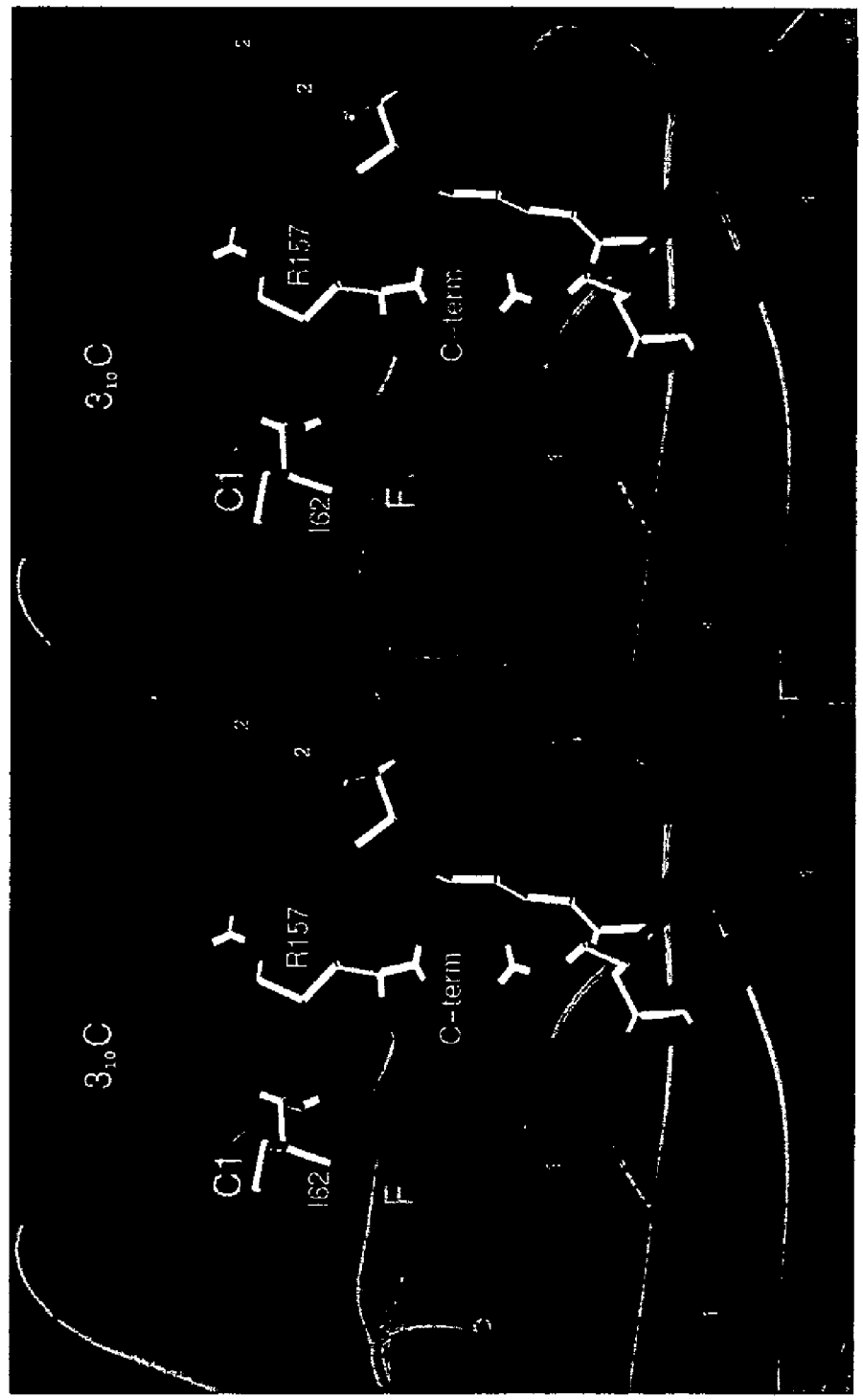
FIG. 6D is a schematic of a stereo contact diagram of interactions between the C-terminal carboxylate of PapK with PapD. Residues making contacts are shown in stick representation (thin for PapD, and thick for PapK).
Figure 6E:
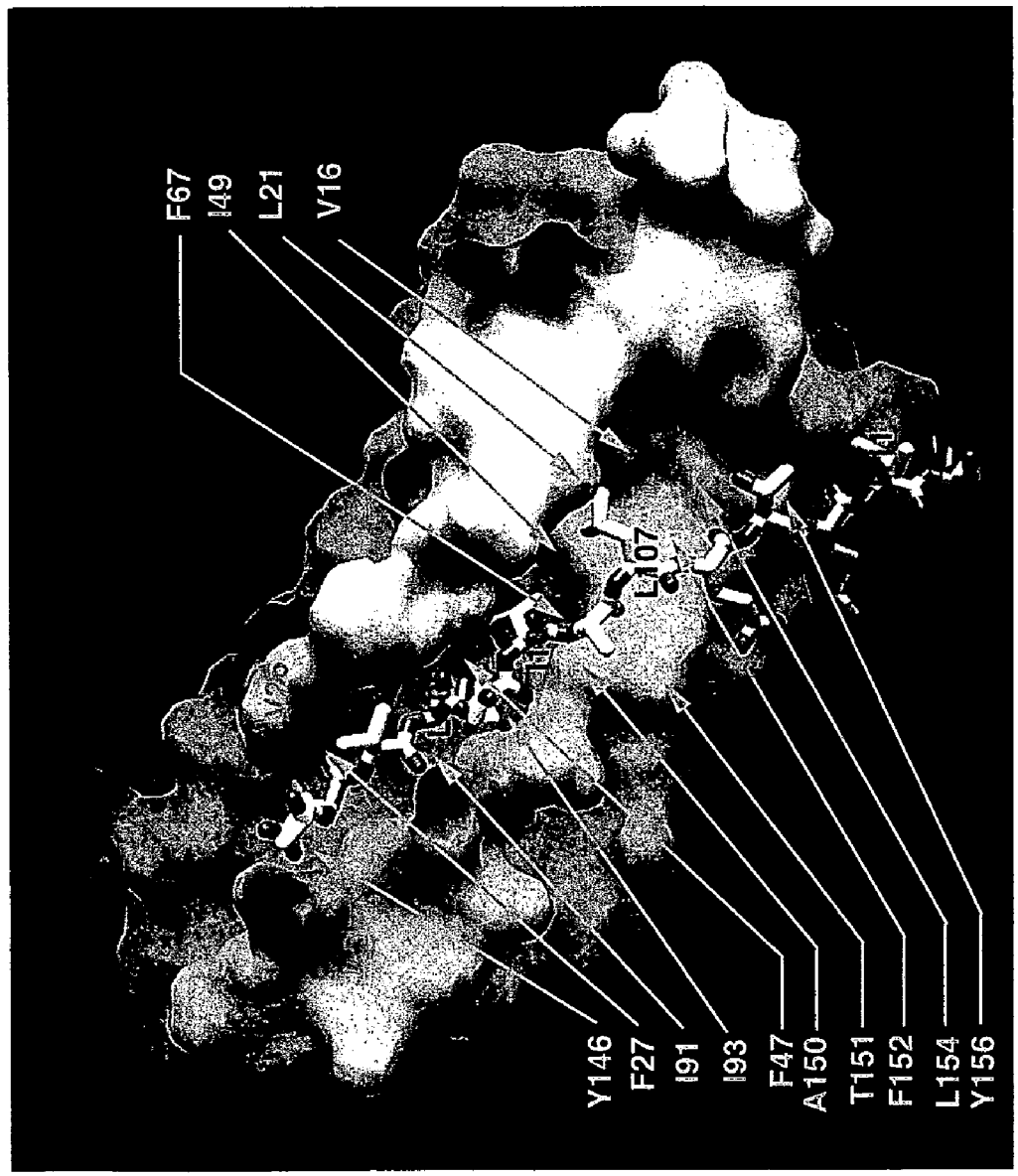
FIG. 6E is a depiction of the $G_1$ beta-strand of PapD as it inserts into the groove of PapK. The PapD $G_1$ strand is represented as a stick model with color coding as in FIG. 6A and PapK is shown as a molecular surface calculated using GRASP. Notice the predominance of hydrophobic residues in the groove, the base of which is part of the hydrophobic core of the protein.
Figure 7B:
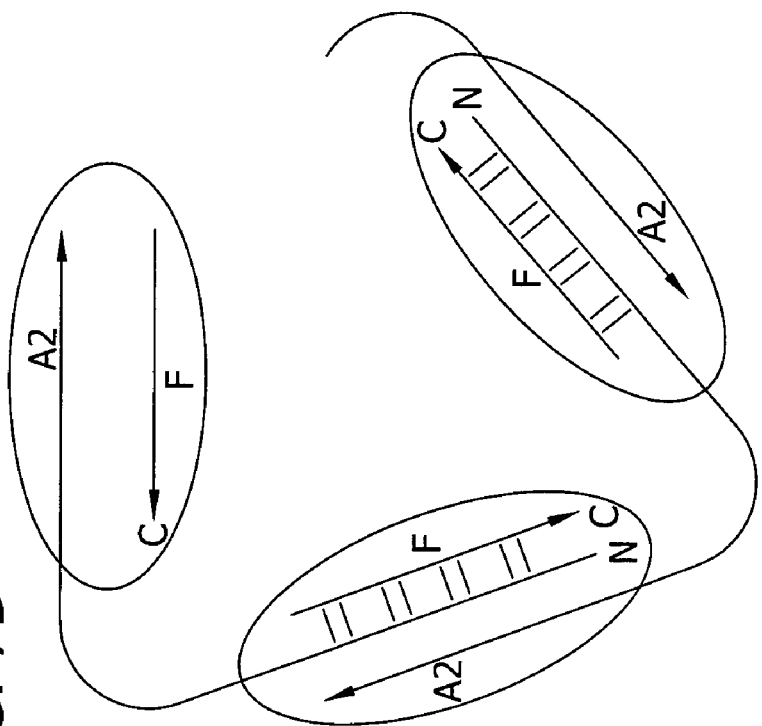
FIG. 7B is a schematic diagram of subunit—subunit interactions in pilus model as viewed from above. Insertion of the $NH_2$-terminal strand antiparallel to strand F yields a cross-section compatible with electron microscopy data Strands (arrows) are labeled, as are the $NH_2$- and COOH-termini (N and C respectively). Hydrogen bonding interactions are shown schematically.
Figure 7A:
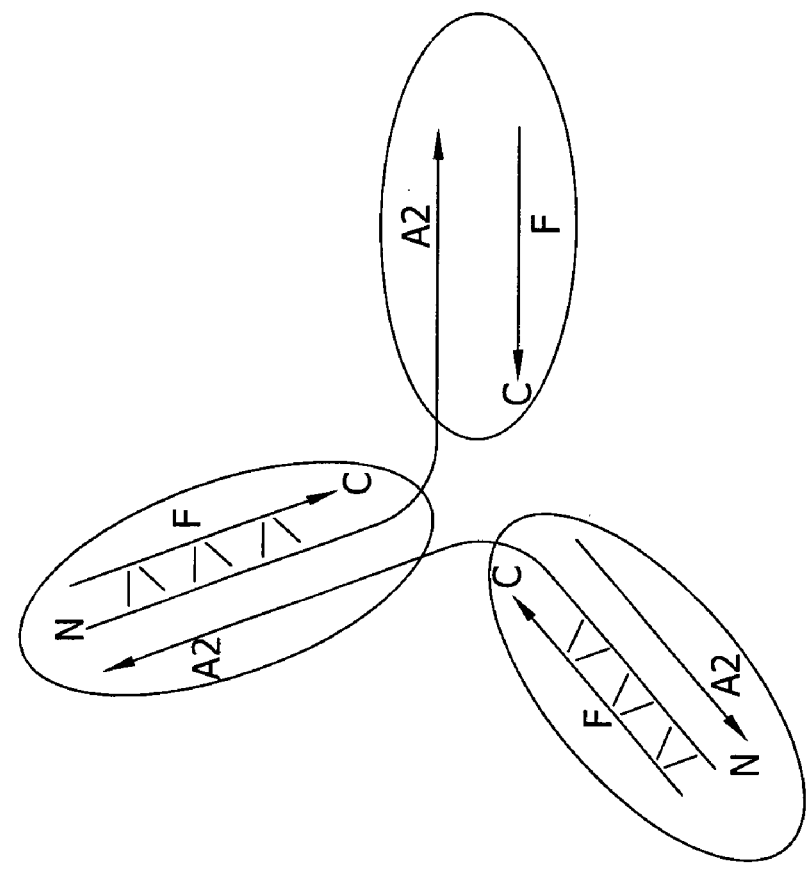
FIG. 7A is a schematic diagram of subunit—subunit interactions in pilus rod model as viewed from above. Insertion of the $NH_2$-terminal strand of one subunit into the groove made by the A2 and F strands of the preceding subunit such that the $NH_2$-terminal strand is parallel to strand F results in a three-pointed-star-shaped cross-section inconsistent with electron microscopy data Strands (arrows) are labeled, as are the $NH_2$- and COOH-termini (N and C respectively). Hydrogen bonding interactions are shown schematically.
Figure 7C:
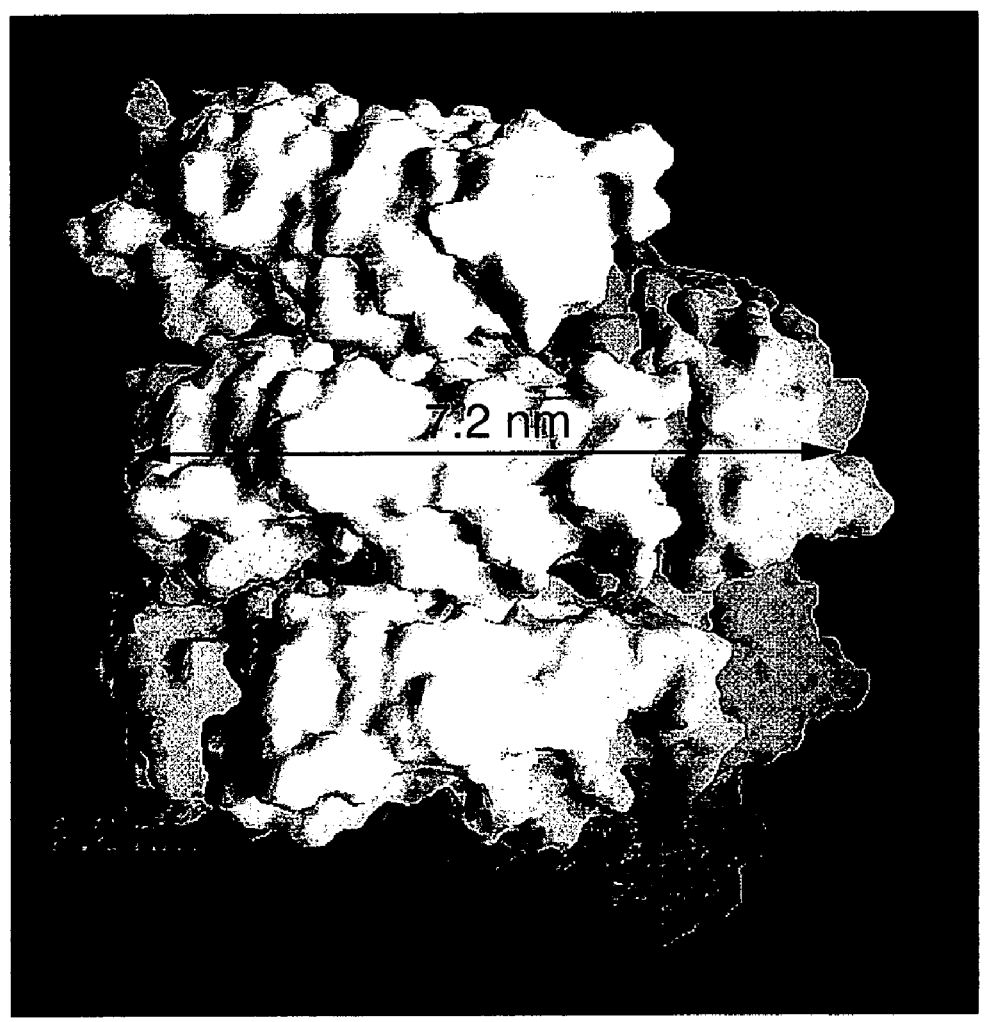
FIG. 7C is a molecular surface of a pilus rod (program GRASP). The disordered residues at the $NH_2$-terminus of the subunit were modeled as a strand that inserts into the groove of the preceding subunit. Approximately three turns of the model pilus, whose dimensions are similar to the known values from electron microscopy are shown.
Figure 7D:
FIG. 7D is a stereo ribbon diagram of the rod model. The insertion of the $NH_2$-terminal strand of one subunit into the groove of the preceding subunit can be clearly seen.

Site K2 is formed primarily by residues in helix $3_{10}$C. and the COOH-terminal $Arg^{157}$ side chain of PapK (FIGS. 6C and 6D). This interface is less extensive than site K1 (455 $A^2$). Residues in site K2 interact with residues in the $C_2$ and $D_2$ strands and with the $F_2$–$G_2$ loop of domain 2 of PapD (Site D2). The K2-D2 interface includes hydrogen bonds between $Thr^{57}$ of PapK and the main-chain carbonyls of $Glu^{164}$ and $Glu^{165}$ of PapD, as well as polar and hydrophobic contacts involving $Lys^{61}$ and $Ile^{62}$ of PapK and $Arg^{200}$ and $Ile^{154}$ of PapD.

Example 2

Preparation and Comparison of FimA Subunits from Different Strains of *E. coli*.

Genomic DNA was prepared from overnight broth cultures of 59 uropathogenic *E. coli* strains using the Puregene DNA Isolation Kit (Minneapolis, Minn.). DNA was amplified by PCR using Taq polymerase (Perkin Elmer) using the following primers: 5'-CATCGCTGGCACAGGAAG-GAGC-3' (SEQ ID NO: 53) and 5'-GTTGGTATGACCCG-CATCAATCGC-3' (SEQ ID NO: 54) that flank the fimA locus, under the following conditions:cycle 1 (95° C. for 1 min), cycle 2–30 (95° C. for 30 sec., 50° C. for 30 sec, 72° C. for 2 min.) in the presence of 3.0 mM $MgCl_2$. The FimA amplified fragments were purified with a QIAquick Purification Kit (Qiagen, Germany), sequenced directly without subcloning using the dRhodamine Terminator Cycle Sequencing Kit (Perkin Elmer, Norwalk, Conn.) and analyzed on the ABI 373 Automated DNA Sequencer (PE Applied Biosystems, Foster City, Calif.). The FimA sequences were aligned and compared using the Lasergene software program (DNAStar).

Example 3

Structure of FimH in the FimH-FimC Co-Crystal

FimH is folded into two domains of the all-beta class. The $NH_2$-terminal mannose-binding domain comprises residues 1H–156H, and the COOH-terminal pilin domain which is used to anchor the adhesin to the pilus comprises residues 160H–279H. A short extended linker (residues 157H–159H) connects the two domains. FimC in the co-complex has the same overall structure as free FimC. The pilin domain of FimH binds in the cleft of the chaperone, but mostly to the chaperone's $NH_2$-terminal domain.

The lectin domain of FimH is an 11-stranded elongated beta-barrel with a jelly roll-like topology (FIG. 8B). A pocket capable of accommodating a mono-mannose unit is located at the tip of the domain, distal from the connection to the pilin domain (FIG. 9B). The bottom of the pocket is lined with asparagine, glutamine and aspartic acid residues in three loop regions which are typical carbohydrate binding side chains (FIG. 10A). A molecule of cyclohexylbutanoyl-N-hydroxyethyl-D-glucamide (C-HEGA) is bound in this pocket. C-HEGA is not a known inhibitor of FimH mannose binding but was needed in the crystallization to produce useful co-crystals of FimC-FimH co-complex. The glucamide moiety of C-HEGA is blocked at C1 and cannot form a pyranose, but is bent to approach the pyranose conformation. The C2, C3, C4 and C6 hydroxyl groups of C-HEGA are enclosed within the pocket, whereas the C5 hydroxyl and cyclohexylbutanoyl-N-hydroxyethyl groups point out from the pocket and are solvent exposed. Residues $Asp^{54H}$, $Gln^{133H}$, $Asn^{135H}$, $Asp^{140H}$ and the $NH_2$-terminal amino group of FimH (FIG. 10A) are hydrogen bonded to the glucamide moiety of C-HEGA. FimH from a urinary tract *E. coli* isolate which has a lysine instead of asparagine at position 135H produces type 1 pili but is unable to mediate mannose sensitive hemagglutination of guinea pig erythrocytes (S. Langermann, unpublished results). Also, a mutation at residue 136H has been reported to completely block mannose binding. See Schembri et al., FEMS Microbiol. Lett., 137, 257 (1996).

The pilin domain of FimH has the same immunoglobulin-like topology as the $NH_2$-terminal domain of FimC, except that the seventh strand of the fold is missing. Two antiparallel beta-sheets (strands A'BED' and D"CF) pack against each other to form a beta-barrel that is similar to, but distinct from, immunoglobulin barrels. As in the chaperones, strand switching occurs at the edges of the sheets. In the chaperones, the A1 strand of the $NH_2$-terminal domain switches between the two sheets of the barrel. The first strand of the pilin domain exhibits a similar switch, but due to the lack of a seventh strand, the second half of the A strand is not involved in main chain hydrogen bonding within the domain. The D strand of the chaperones as well as of the FimH pilin domain also switches, but in the pilin domain the switch is an 8-residue loop instead of the cis-proline bulge found in the chaperones. The C–D loop and the D'-D" connection pack against each other and close the top of the barrel. The other side of the barrel, defined by the A and F edge strands, is open. Due to the absence of a seventh strand a deep scar is created on the surface of the domain. Residues that would be part of the hydrophobic core of an intact, seven-stranded PapD-like domain instead line a deep hydrophobic crevice on the surface of the pilin domain.

Example 4

FimC-FimH Co-crystal Structure

FimC-FimH co-crystals were grown by hanging drop vapor diffusion by mixing 2 μl of a protein solution (4 mg of FimC-FimH co-complex per milliliter pre-equiliabrated in 300 mM of HEGA) with 2 μl of reservoir solution containing 1 M ammonium sulfate in 0.1 M tris-HCl buffer (pH 8.2). The structure of the FimC-FimH co-complex was solved to 2.5 Å (Table 5). Eight copies of the FimC-FimH co-complex in the asymmetric unit were arranged as two sets of four molecules related by approximate 4, screw axes. Electron density was excellent for one set of molecules (FIG. 9A), allowing applicants to trace the entire co-complex. For the second set of molecules, electron density was poorer but allowed for unambiguous placement of a copy of the initially traced co-complex.

Two seleno-methionine FimC-FimH co-crystals were used to collect MAD (W. A. Hendrickson, *Science* 254: 51 (1991)) data on BM14 of the ESRF. Data were recorded at each of 3 wavelengths corresponding to the peak of the Se white line, the point of inflexion of the K absorption edge, and a remote wavelength using a MAR CCD detector. Data were reduced using the program HKL2000 (Z. Otwinowski and W. Minor, "*Methods in Enzymology*" C. W. Carter, R. M. Sweet, Eds. (Academic Press, New York, 1997), vol. 276, pp. 307), with further processing and scaling using the CCP4 processing package (CCP4, Acta. Cryst. D50, 760 (1994)).

The co-crystals used for the structure determination belong to the space group C2 with cell dimensions a=139.08±0.2 Å, b=139.08±0.2 Å, c=214.49±0.2 Å, and beta=89.97±0.2 Å. The co-crystals exhibit strong pseudo $P4_12_12$ symmetry. An initial solution to the Patterson function was produced in the tetragonal pseudo space group both automatically using the program SOLVE (T. C. Terwilliger and J. Berendzen, *Acta. Cryst. D*53, 571 (1997)) and manually using the program RSPS (S. Knight, I. Andersson, C.-I. Brändén, *J. Mol. Biol.* 215: 113 (1990)), and initial phases calculated using SHARP (E. de la Fortelle and G. Bricogne, in *Methods in Enzymology* C. W. Carter, R. M. Sweet, Eds. (Academic Press, New York, 1997), vol. 276, pp. 472)). Density modification including 4-fold non-crystallographic (NCS) averaging was done using the program DM (K. D. Cowtan, *Joint CCP4 ESF-EACBM Newsl. Protein Crystallogr.* 31: 34 (1994)). A model corresponding to the two copies of the co-complex in the pseudo asymmetric unit was built using 0 (T. A. Jones et al., *Acta. Cryst.* A47, 110 (1991)) modeled in 4-fold averaged electron density and refined against 2.5 Å native data applying tight non-crystallographic restraints. The crystals are in either space group $P4_12_12$ or $P4_3$, with cell dimensions a=b=97.7±0.2 angstroms and c=215.9±0.2 angstroms. Bulk solvent correction, positional, simulated annealing, and isotropic temperature factor refinement has been carried out using X-PLOR (A. T. Brünger, *X-PLOR Manual (Version 3.1): A system for X-ray crystallography and NMR* (Yale University Press, New Haven, Conn., 1993)) and REFMAC (G. N. Murshudov, A. A. Vagin, E. J. Dodson, *Acta. Cryst.* D53, 240 (1997)) with tight NCS restraints against a 2.5 Å native data set collected at Max II/BL711 in Lund. The current R-factor and R-free (on 5% of the data) are 24.0% and 26.8%, respectively. The r.m.s. deviations from ideal bond length and angle values are 0.016 Å and 3.3°, respectively. No residues are found in disallowed regions of the Ramachandran plot. The coordinates have been deposited at the Research Collabortory for Structural Bioinformatics Protein Data Bank (code 1QUN).

TABLE 5

Summary of Data Collection and MAD Structure Determination

| Crystal | $d_{min}$ (Å) | $N_{unique}$ | Cmplt[1] (%) | Mult[2] | Ils(I)[3] | $R_{sym}$[4] (%) | $R_{anom}$[5] (%) |
|---|---|---|---|---|---|---|---|
| SeMet Crystal 1 | | | | | | | |
| Remote | 2.8 | | 82.8 | | | | |
| Point of Infection | | 93019 | | 2.5 | 13.1(3.7) | 4.0(17.3) | 3.5(16.8) |
| Peak | | 75467 | | 2.1 | 11.6(6.9) | 3.5(24.4) | 4.3(21.4) |
| | | 82754 | | 2.7 | 11.3(1.9) | 4.1(24.7) | 4.2(18.8) |
| SeMet Crystal 2 | | | | | | | |
| Remote | 2.7 | | 98.7 | | | | |
| Point of Infection | | 110928 | | 3.8 | 8.9(2.0) | 5.1(28.3) | 4.2(20.9) |
| Peak | | 110415 | | 4.0 | 10.6(2.7) | 4.2(21.8) | 3.8(17.4) |
| | | 110418 | | 3.9 | 14.4(2.8) | 4.2(20.8) | 4.2(17.5) |
| Native | 2.5 | 139645 | 98.0 | 4.1 | 5.3(1.6) | 7.6(25.3) | N/A |

Phasing Statistics from SHARP

| | Point of inflexion λ = 0.9793 Å | | Peak λ = 0.9792 Å | | Remote λ = 0.885 Å | |
|---|---|---|---|---|---|---|
| | Centric | Acentric | Centric | Acentric | Centric | Acentric |
| Phasing power[6] | 2.0/— | 2.1/1.2 | 2.0/— | 2.0/1.6 | —/— | —/0.81 |
| $R_{cullis}$[7] | 0.49/— | 0.56/0.52 | 0.53/— | 0.54/0.57 | —/— | —/0.69 |
| Resolution(Å) | 7.59 | 5.50   4.52 | 3.93 | 3.53 | 3.23 | 2.99   2.80 |
| FOM[8] | 0.623 | 0.508   0.379 | 0.227 | 0.172 | 0.140 | 0.105   0.125 |

[1]Completeness
[2]Multiplicity
[3]Overall value, values in parentheses are for the highest resolution shell
[4]$R_{sym} = S_h S_i |I_i(h) - \langle I(h)\rangle| / S_h S_i I_i(h)$, where $I_i(h)$ and $\langle I(h)\rangle$ are the intensities of the individual and mean structure factors, respectively. High resolution shell in parentheses.
[5]$R_{anom} = S_h S_i |I_i(h) - \langle I(h)\rangle| / S_h S_i I_i(h)$, $I_i(h)$ and $\langle I(h)\rangle$ are as defined above, and the summation is over anomalous pairs. High resolution shell in parentheses.
[6]$F_H(calc)/E$, where E is the estimated lack-of-closure error (isomorphous/anomalous).
[7]$R_{cullis} = S||F_{PH} - F_P| - F_H(calc)|/S|F_{PH} - F_P|$, where $F_P$ and $F_{PH}$ are protein and heavy atom structure factors, respectively, and $F_H(calc)$ is the calculated heavy-atom structure factor (isomorphous/anomalous).
[8]Figure of merit for SHARP phases Example 4

FimC-FimH Co-Complex Structure

In the FimC-FimH co-complex, the seventh strand ($G_1$ beta-strand) from the $NH_2$-terminal domain of the FimC chaperone is used to complement the pilin domain by being inserted between the second half of the A strand and the F strand of the domain (FIG. 10C). Thus, the final strand (F) of FimH forms a parallel beta-strand interaction with the G1 strand of FimC and has its COOH-terminal carboxyl group anchored in the crevice of the chaperone cleft through hydrogen bonding with the conserved residues Arg$^{8C}$ and Lys$^{112C}$ in FimC (FIG. 9A).

The $G_1$ beta-strand of the FimC chaperone contains a conserved motif of solvent exposed hydrophobic residues at positions 103, 105, and 107. In the FimC-FimH co-complex, these residues are used to complete the unfinished hydrophobic core of FimH (FIG. 10C). The two residues Leu$^{103C}$ and Leu$^{105C}$ are deeply buried in the crevice created in the FimH pilin domain due to the missing seventh strand. Ile$^{107C}$ is somewhat closer to the domain surface but makes van der Waals contacts with residues Val$^{163H}$ and Phe$^{276H}$. Leu$^{103C}$ contacts residues Ile$^{181H}$, Val$^{223H}$, Leu$^{225H}$ and Ile$^{272H}$. Leu$^{105C}$ is in contact with Ile$^{181H}$, Leu$^{183H}$, Leu$^{252H}$, Ile$^{272H}$ and Val$^{274H}$. This mode of binding is called "donor strand complementation" to emphasize the fact that the pilin domain is incomplete and that the chaperone donates its G1 beta-strand to complete the fold of the pilin.

Example 5

Subunit-subunit interactions in Type 1 Pili

Genetic, biochemical and electron microscopic studies have demonstrated that residues in the two conserved motifs (the COOH-terminal F strand and an $NH_2$-terminal motif) participate in subunit—subunit interactions necessary for pilus assembly. See G. E. Soto et al., EMBO J, 17: 6155 (1998). An alignment of the pilin sequences, based on the FimC-FimH co-crystal structure, revealed that the $NH_2$-terminal motif was part of a 10–20 residue $NH_2$-terminal extension that was missing in the FimH pilin domain (FIG. 8A). This region contains a highly conserved pattern of alternating hydrophobic residues (highlighted in FIG. 8A) similar to the donor G. beta-strand of the chaperone. This motif is structurally analogous to the G1 donor strand motif of the chaperone and molecular modeling indicates that it would be able to fit into the same groove occupied by the donor $G_1$ beta-strand of the chaperone.

The type 1 pilus is a right handed helix with about 3 subunits per turn, a diameter of approximately 70 Å, a central pore of about 20–25 Å, and a rise per subunit of about 8 Å. In order to obtain this structure, insertion of the $NH_2$-terminal extension must be antiparallel to strand F in contrast to the parallel insertion observed for the $G_1$ beta-strand of the chaperone. Insertion in a parallel orientation would lead to rosette-like structures. One edge of the pilin groove is lined by the COOH terminal F strand which has been shown to form a critical part of the subunit tail. Thus, the $NH_2$-terminal extension represents the head of a subunit and during pilus biogenesis, it would displace the donor $G_1$ beta-strand of the chaperone to fit into the tail groove of a neighboring subunit and to complete the pilin fold of its neighbor in a donor strand complementation mechanism.

Using the FimH pilin domain as a model for FimA, applicants constructed a model for the type 1 pilus that fit these data (FIG. 11). Each subunit was aligned to have its cleft facing towards the center of the pilus so that the height from the top to the bottom of the domain along the helix axis was approximately 25 Å. Applying a rotation of 115 degrees and a rise per subunit of 8 Å, a hollow helical cylinder is created. The outer diameter of this cylinder as measured across $C_\alpha$ atoms is 70 Å, and the inner diameter is 25 Å. FimA subunits from different strains of E. coli exhibit considerable allelic variation. The vast majority of the variable positions are on the outside surface of the pilus model proposed above (FIG. 11) which would account for the antigenic variability of type 1 pili.

The proposed head-to-tail interaction between subunits in a pilus is reminiscent of oligomerization through three-dimensional domain swapping in the sense that a part of the molecule is used to complement another. However, in this case, complementation occurs not only between identical protein chains (FimA in the pilus rod) but also between homologous but distinct chains e.g., FimG, FimF and FimH in the pilus tip. Furthermore, because individual pilins promoters do not exist as stable monomers, there is no exchange of structural units between a monomeric and an oligomoeric state. Instead, a different protein, the periplasmic chaperone, is needed to keep the monomeric subunits in solution by donating a unique part of its structure (the $G_1$ beta-strand) to the different subunit grooves.

Based on the structure of the FimC-FimH co-complex, pilins are missing the necessary steric information needed to fold into a native three dimensional structure. The information that is missing consists of the seventh edge strand of an immunoglobulin fold. This strand, which is necessary for folding, is donated to the hydrophobic core of the pilin by the periplasmic chaperone in a donor strand complementation mechanism. Thus, the steric information necessary for newly synthesized protein chains to fold correctly is not inherent in the sequence of the protein to be folded; however, such information is instead transferred from another protein, the periplasmic chaperone.

Example 6

FimH Binding to FimC and FimG by ELISA Assay

The ability of FimH to bind to peptides corresponding to the $G_1$ beta-strand of FimC and the N-terminal extension of FimG was tested using an ELISA assay. During pilus assembly, the $G_1$ beta-strand of FimC completes the Ig fold of the FimH pilin domain in the periplasm and then in the pilus the N-terminal extension of FimG completes the Ig fold of the FimH pilin domain.

In order to assess the ability of FimH to bind to the two peptides, FimH was purified from the FimC-FimH co-complex. Synthetic peptides were synthesized corresponding to the $G_1$ beta-strand of FimC and the N-terminal extension of FimG. The synthesized peptide sequences are as follows: FimC peptide, NTLQLAIISR (SEQ ID NO: 55) and FimG peptide, DVTITVNGK (SEQ ID NO: 56). Stock solutions of the peptides (5 mg/ml) were dissolved in DMSO.

The peptides were diluted in phosphate buffered saline (PBS) (120 mM NaCl, 2.7 mM KCl, 10 mM, 10 mM PBS, pH 7.4) to 2 nmol/50 µl. FimC protein was diluted to 0.1 nmol/50 µl and coated overnight onto microtiter wells with 50 µl/well at 4° C. The ELISA assay was carried out as described in Kuehn et al., 1993 and Hung et al., 1996. Briefly, the wells were washed three times with PBS and blocked with 3% Bovine Serum Albumin (BSA) in PBS for two hours at 25° C. Then the wells were washed three times with PBS. The FimC-FimH co-complex was incubated in 3 M urea to separate the two proteins. Pure FimH in 3 M urea was collected from the flow through of a Source 15S column (Pharmacia). See Barnhart et al., PNAS USA 97: 7709–7714 (2000). The wells were incubated with 50 µl of FimH in 3% BSA-PBS diluted to 5–25 pmol/well FimH for 45 minutes at 25° C. The wells were washed 3 times with PBS followed by incubation with a 1:1000 dilution of mouse anti-FimH antibodies in 3% BSA-PBS for 45 minutes at 25° C. The wells were washed 3 times with PBS followed by incubation with a 1:1000 dilution of goat antiserum to mouse IgG (Sigma) conjugated to alkaline phosphatase diluted in 3% BSA-PBS for 45 minutes at 25° C. The wells were washed 3 times with PBS and washed 3 times with developing buffer (10 mM diethanolamine, 0.4 mM $MgCl_2$). The ELISA was developed by adding 50 µl of substrate (50 µl of filtered 1 mg/ml p-nitrophenyl phosphate; Sigma) in developing buffer. The reaction was incubated for 1 hour at 25° C. in the dark and the absorbance at 405 nm was read.

Figure 12:
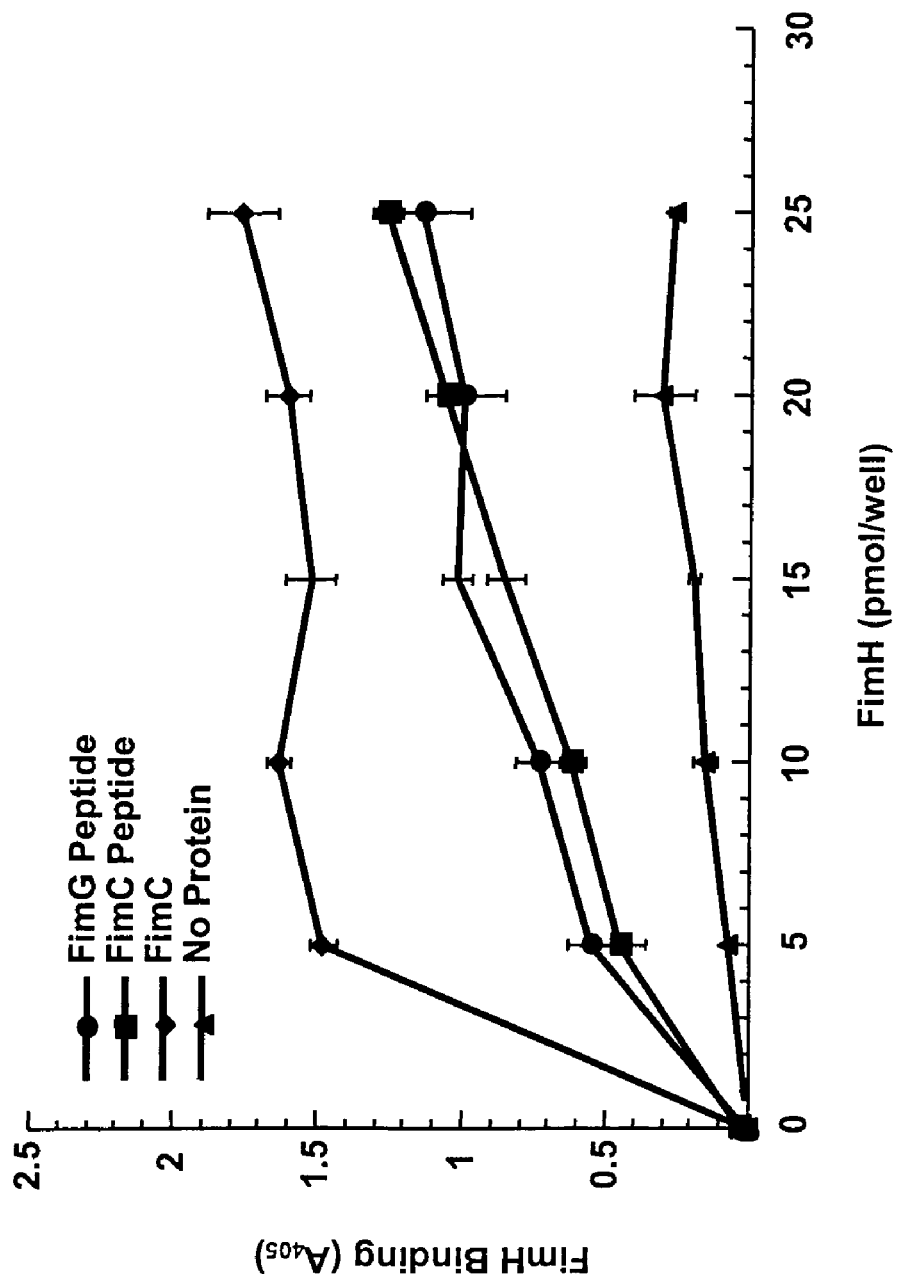
FIG. 12 is a graphic representing the binding of FimH to polypeptides corresponding to the G1 beta-strand of FimC and the N-terminal extension of FimC. The two polypeptides or FimC were coated onto microtiter wells and FimH binding to the immobilized polypeptides or FimC protein was determined by ELISA using anti-FimH antibodies. The graph represents the average of triplicate wells with the standard deviation shown in bars.
Figure 13:
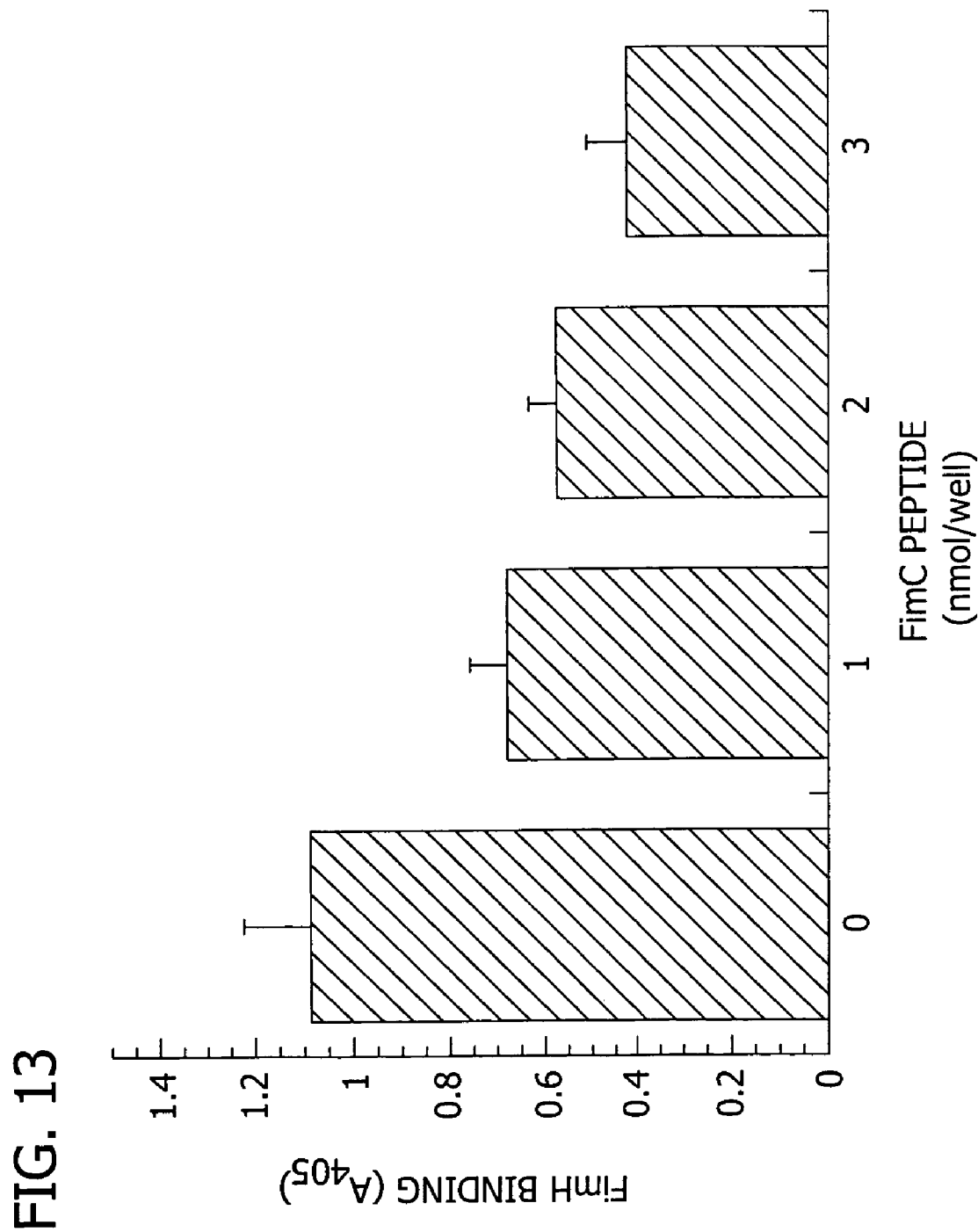
FIG. 13 is a graph which represents the binding of FimH in the presence of increasing concentrations of the FimC polypeptide. It can be seen that FimC polypeptides inhibit FimH binding to FimC. The graphs represent the average of triplicate wells with the standard deviation shown in bars.
Figure 14:
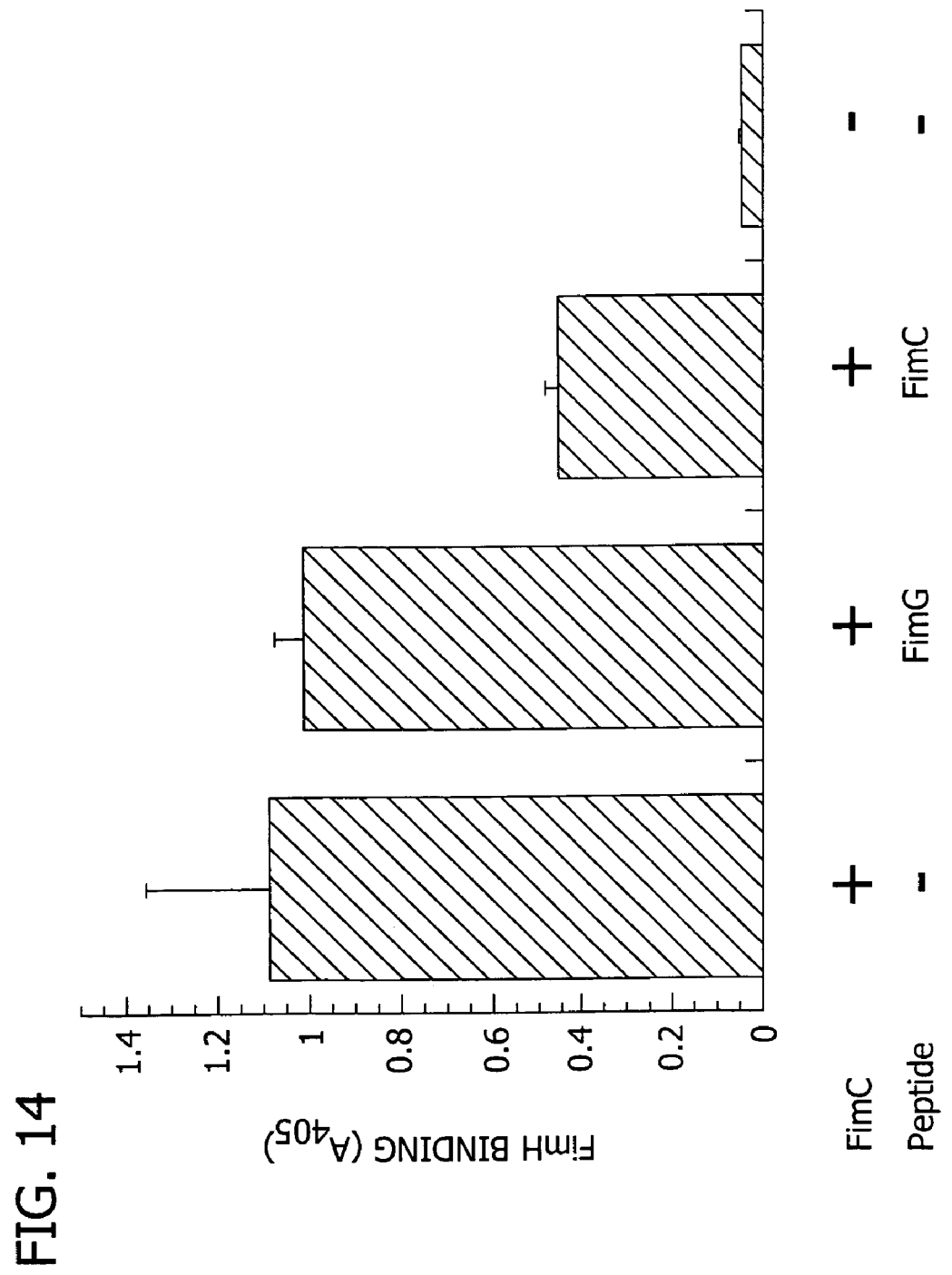
FIG. 14 is a graph which represents the FimH binding to FimC in the presence or absence of FimG or FimC polypeptides as monitored by ELISA. The graphs represent the average of triplicate wells with the standard deviation shown in bars.

The competition assays were carried out similarly. FimC was coated onto microtiter wells at 0.1 nmol/well. FimH at 5 pmol/well in 3% BSA-PBS was added to the FimC coated wells in the presence or the absence of the FimC or FimG peptide at 2 nmol/well or the indicated peptide concentration. Further, increasing concentrations of FimH were incubated with constant concentrations of the FimC or FimG peptides or the FimC protein immobilized on microtiter wells. FimH bound well to both pure FimC protein immobilized on microtiter wells (FIG. 12) and to the peptides corresponding to the $G_1$ beta-strand of FimC and the N-terminal extension of FimG (FIG. 12). Next, the ability of the peptides to inhibit FimH binding to FimC was tested. FimH was added to the FimC coated wells in the presence or absence of peptides to FimC or FimG. Increasing concentrations of the FimC peptide further decreased the ability of FimH to bind to FimC immobilized on microtiter wells (FIG. 13). The FimC peptide inhibited the ability of FimH to bind to FimC immobilized on the microtiter wells (FIG. 14); however, the FimG peptide at the tested concentration did not inhibit the ability of FimH to bind to FimC (FIG. 14).

Other features, objects and advantages of the present invention will be apparent to those skilled in the art. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the present invention.

We claim:

1. An isolated compound which inhibits pilus assembly, or a pharmaceutically-acceptable salt thereof, said compound comprising a mimic of a chaperone G1 beta-strand or a mimic of an amino terminal motif of a pilus subunit, wherein the mimic is a 10 to 20 residue peptide, having an amino terminus and a carboxy terminus, according to formula (I):

$$Z_1 \sim Z_2 - X_1 - X_2 - X_3 - X_4 - X_5 - X_6 - X_7 - X_8 - X_9 - X_{10} - Z_3 \sim Z_4 \qquad (I)$$

wherein:

$Z_1$ is the amino terminus of the mimic peptide, $Z_1$ having the formula

R—C(O)—NR— or RRN—;

$Z_2$ is (i) a first peptide sequence consisting of 1 to 5 amino acid residues or (ii) a bond connecting $Z_1$ to $X_1$;

$X_1$ is any amino acid residue;

$X_2$ is any amino acid residue;

$X_3$ is a hydrophobic residue or a hydroxyl-substituted aliphatic residue;

$X_4$ is any amino acid residue;

$X_5$ is a hydrophobic residue or Gly;

$X_6$ is a hydrophobic or a hydrophilic residue;

$X_7$ is Gly, an amide-substituted polar residue or a hydrophobic residue;

$X_8$ is an amino acid residue other than an aliphatic residue;

$X_9$ is an aliphatic residue;

$X_{10}$ is any amino acid residue;

$Z_3$ is (i) a second peptide sequence consisting of 1 to 5 amino acid residues or (ii) a bond connecting $Z_4$ to $X_{10}$;

$Z_4$ is the carboxy terminus of the peptide, Z4 having the formula —C(O)OR or —C(O)NRR;

each R is independently hydrogen, $(C_1–C_6)$ alkyl, $(C_2–C_6)$ alkenyl, $(C_2–C_6)$ alkynyl or $(C_6–C_{14})$ aryl;

each "-" between residues $X_1$ through $X_{10}$, $Z_2$ and $X_1$ and $X_{10}$ and $Z_3$ independently represents an amide linkage, a substituted amide linkage or an isostere of an amide linkage; and each "~" represents a bond.

2. The compound of claim 1 wherein the compound exhibits antibacterial activity against a Gram-negative bacterium.

3. An isolated compound which inhibits pilus assembly, said compound comprising SEQ ID NO: 1, wherein the compound is a mimic of a chaperone $G_1$ beta-strand and the compound exhibits antibacterial activity against a Gram-negative bacterium.

4. The compound of claim 1 wherein the compound comprises a mimic of an amino terminal motif of a pilus subunit selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28 and SEQ ID NO: 29.

5. The compound of claim 4 wherein said mimic of an amino-terminal motif of a pilus subunit further comprises the amino acid sequence SDVAFRGNLL (SEQ ID NO: 12) or an analog thereof.

6. The compound of claim 1 wherein one or more of the following conditions are satisfied:
each "-" between residues $X_1$ through $X_{10}$, $Z_2$ and $X_1$ and $X_{10}$ and $Z_3$ is an amide linkage;
$Z_1$ is $H_2N$—;
$Z_4$ is —C(O)OH or a salt thereof;
$Z_2$ is a bond connecting $Z_1$ to $X_1$;
$Z_3$ is a bond connecting $Z_4$ to $X_{10}$;
$X_1$ is an amino acid residue other than a basic residue;
$X_2$ is an amino acid residue other than an aliphatic residue;
$X_3$ is an aliphatic residue or T;
$X_4$ is an amino acid residue other than an acidic residue;
$X_5$ is an aliphatic residue, F or G;
$X_7$ is G, N or A; or
$X_{10}$ is an aliphatic or a polar residue.

7. The compound of claim 6 wherein the mimic comprises a sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28 and SEQ ID NO: 29.

8. An isolated compound which inhibits pilus assembly, or a pharmaceutically-acceptable salt thereof, the compound comprising a mimic of a chaperone $G_1$ beta-strand or a mimic of an amino terminal motif of a pilus subunit, wherein the mimic is a 7 to 17 residue peptide or peptide analog, having an amino terminus and a carboxy terminus, according to formula (II):

$$Z_{11}\text{~}Z_{12}\text{-}X_{11}\text{-}X_{12}\text{-}X_{13}\text{-}X_{14}\text{-}X_{15}\text{-}X_{16}\text{-}X_{17}\text{-}Z_{13}\text{~}Z_{14} \quad (II)$$

wherein:
$Z_{11}$ is the amino terminus of the peptide, $Z_{11}$ having the formula R'—C(O)NR'— or R'R'N—;
$Z_{12}$ is (i) a first peptide sequence consisting of 1 to 5 amino acid residues or (ii) a bond connecting $Z_{11}$ to $X_{11}$;
$X_{11}$ is any amino acid residue;
$X_{12}$ is any amino acid residue;
$X_{13}$ is a hydrophobic residue;
$X_{14}$ is any amino acid residue;
$X_{15}$ is a hydrophobic residue;
$X_{16}$ is any amino acid residue;
$X_{17}$ is hydrophobic residue or a hydroxyl-substituted aliphatic residue;
$Z_{13}$ is (i) a second peptide sequence consisting of 1 to 5 amino acid residues or (ii) a bond connecting $Z_{14}$ to $X_{17}$;
$Z_{14}$ is the carboxy terminus of the peptide, $Z_{14}$ having the formula —C(O)OR' or —C(O)NR'R';
each R' is independently hydrogen, $(C_1–C_6)$ alkyl, $(C_2–C_6)$ alkenyl, $(C_2–C_6)$ alkynyl or $(C_6–C_{14})$ aryl;
each "-" between residues $X_{11}$ through $X_{17}$, $Z_{12}$ and $X_{11}$ and $X_{17}$ and $Z_{13}$ independently represents an amide linkage, a substituted amide linkage or an isostere of an amide linkage; and
each "~" independently represents a bond.

9. The compound of claim 8 wherein one or more of the following conditions are satisfied:
each "-" between residues $X_{11}$ through $X_{17}$, $Z_{12}$ and $X_{11}$ and $X_{17}$ and $Z_{13}$ is an amide linkage;
$Z_{11}$ is $H_2N$—;
$Z_{14}$ is —C(O)OH or a salt thereof;
$Z_{12}$ is a bond connecting $Z_{11}$ to $X_{11}$;
$Z_{13}$ is a bond connecting $Z_{14}$ to $X_{17}$;
$X_{11}$ is an amino acid residue other than a basic residue;
$X_{13}$ is an aliphatic residue or M;
$X_{14}$ is an amino acid residue other than an aromatic residue;
$X_{15}$ is an aliphatic residue, F or M; and
$X_{17}$ is an aliphatic residue, F, M or a hydroxyl-substituted aliphatic residue.

10. The compound of claim 8 wherein the compound consists essentially of a 7 to 17 residue peptide according to formula (II).

11. The compound of claim 1 wherein the compound consists essentially of a 10 to 20 residue peptide according to formula (I).

12. The compound of any one of claims 1, 3, 4, 5, 6, 7, 8, or 9 wherein said compound exhibits antibacterial activity against one or more Gram-negative bacterium selected from the group consisting of *E. coli, H. influenzae, S. euteriditis, S. typhimurium, B. pertussis, Y. pestis, Y. entarocolitica, H. pylon* and *K. pneumoniae*.

13. An isolated compound which inhibits pilus assembly, the compound consisting of SEQ ID NO: 12.

14. An isolated compound which inhibits pilus assembly, the compound consisting essentially of SEQ ID NO: 12, wherein the compound is a mimic of an amino terminal motif of a pilus subunit.

15. An isolated compound which inhibits pilus assembly, the compound comprising a mimic of an amino terminal motif of a pilus subunit, wherein the mimic comprises SEQ ID NO:12.

16. The compound of claim 15 wherein the compound competitively binds to a pilus subunit hydrophobic groove.

* * * * *

SEQUENCE LISTING

<160> NUMBER OF SEQ ID NOS: 65

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 1

Asn Val Leu Gln Ile Ala Leu
 1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 2

Gly Lys Val Thr Phe Asn Gly Thr Val Val
 1               5                  10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 3

Gly Thr Val His Phe Lys Gly Glu Val Val
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 4

Gly Lys Val Thr Phe Phe Gly Lys Val Val
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 5

Gly Thr Ile Val Ile Thr Gly Thr Ile Thr
 1               5                  10

<210> SEQ ID NO 6
<211> LENGTH: 10
<212> TYPE: PRT
<213> ORGANISM: Artificial Sequence -continued

```
<220> FEATURE:
<223> OTHER INFORMATION: Description of Artificial Sequence: Synthesized
      Sequence

<400> SEQUENCE: 6

Gly Thr Ile Val Ile Thr Gly Ser Ile Ser
  1               5                  10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 7

Gly Thr Val Lys Phe Val Gly Ser Ile Ile
  1               5                  10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 8

Gly Glu Ile Gln Leu Lys Gly Glu Ile Val
  1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 9

Gly Thr Ile Lys Phe Thr Gly Glu Ile Val
  1               5                  10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 10

Asn Glu Val Thr Phe Leu Gly Ser Val Ser
  1               5                  10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 11

Gly Thr Ile Asn Phe Glu Gly Ser Val Val
  1               5                  10
```

```
<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 12

Ser Asp Val Ala Phe Arg Gly Asn Leu Leu
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 13

Gly Arg Ala Ala Phe His Gly Glu Val Val
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 14

Gly Arg Ala Thr Phe His Gly Glu Val Val
 1               5                  10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 15

Asp Asn Leu Thr Phe Arg Gly Lys Leu Ile
 1               5                  10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 16

Asp Asn Leu Thr Phe Lys Gly Lys Leu Ile
 1               5                  10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence
```

```
<400> SEQUENCE: 17

Gly Trp Leu Asn Leu Gln Gly Thr Ile Leu
 1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 18

Ser Val Val Asn Ile Thr Gly Asn Val Gln
 1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 19

Thr Thr Ile Thr Val Thr Gly Asn Val Leu
 1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 20

Thr Thr Ile Thr Val Thr Gly Arg Val Leu
 1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 21

Cys Met Leu Ala Gly Ser Asn Phe Val Thr
 1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 22

Val Gln Ile Asn Ile Arg Gly Asn Val Tyr
 1               5                   10

<210> SEQ ID NO 23
<211> LENGTH: 10
<212> TYPE: PRT
```

```
<213> ORGANISM: Artificial Sequence
<220> FEATURE:
<223> OTHER INFORMATION: Description of Artificial Sequence: Synthesized
      Sequence

<400> SEQUENCE: 23

Pro Asn Leu Lys Leu Phe Gly Thr Leu Leu
 1               5                  10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 24

Val Tyr Ile Asn Ile Thr Gly Asn Val Ile
 1               5                  10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 25

Gly Lys Ile Thr Phe Asn Gly Lys Val Val
 1               5                  10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 26

Gly Thr Ile Asn Phe Asn Gly Lys Ile Thr
 1               5                  10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 27

Gln Lys Thr Ile Phe Ser Ala Asp Val Val
 1               5                  10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 28

Gly Gln Val Asn Phe Phe Gly Lys Val Thr
 1               5                  10
```

```
<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 29

Gln Arg Thr Ile Ile Thr Ala Asp Val Val
 1               5                  10

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 30

Gly Ser Leu Ser Leu Ala Ile
 1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 31

Asn Tyr Leu Gln Phe Ala Ile
 1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 32

Ser Gly Ile Ala Val Ala Leu
 1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 33

Asn Ile Leu Gln Leu Ala Ile
 1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence
```

```
<400> SEQUENCE: 34

Ser Phe Met Gln Ile Ala Ile
 1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 35

Asn Tyr Leu Gln Phe Ala Val
 1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 36

Asn Thr Leu Gln Leu Ala Ile
 1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 37

Gly Val Leu Gln Leu Thr Ile
 1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 38

Asn Val Leu Ala Val Ala Val
 1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 39

Ser Leu Leu Gln Leu Ala Phe
 1               5

<210> SEQ ID NO 40
<211> LENGTH: 7
```

```
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 40

Ser Gly Ile Ala Val Ala Val
  1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 41

Asn Ala Leu Lys Phe Ala Met
  1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 42

Asn Val Leu Gln Met Ala Met
  1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 43

Asn Tyr Leu Gln Phe Ala Ile
  1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 44

Asn Val Leu Gln Ile Ala Val
  1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 45

Leu Asn Val Asn Val Val Thr
```

```
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 46

Val Phe Val Gln Phe Ala Ile
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 47

Met Lys Leu Asn Val Ser Ile
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 48

Met Asp Ile Gln Met Ser Ile
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 49

Leu Asn Ile Leu Leu Ser Val
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 50

Met Asn Ile Gln Val Ser Val
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthesized
```

-continued

```
                    Sequence

<400> SEQUENCE: 51

Asp Ser Ile Asn Ile Ser Ile
  1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthesized
      Sequence

<400> SEQUENCE: 52

Leu Asn Val Gln Leu Ser Val
  1               5

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 53
catcgctggc acaggaagga gc                                               22

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 54
gttggtatga cccgcatcaa tcgc                                             24

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthesized
      Proteins

<400> SEQUENCE: 55

Asn Thr Leu Gln Leu Ala Ile Ile Ser Arg
  1               5                  10

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthesized
      Proteins

<400> SEQUENCE: 56

Asp Val Thr Ile Thr Val Asn Gly Lys
  1               5

<210> SEQ ID NO 57
<211> LENGTH: 157
<212> TYPE: PRT
<213> ORGANISM: Escherichia coli
```

```
<400> SEQUENCE: 57

Ser Asp Val Ala Phe Arg Gly Asn Leu Leu Asp Arg Pro Cys His Val
  1               5                  10                  15

Ser Gly Asp Ser Leu Asn Lys His Val Val Phe Lys Thr Arg Ala Ser
               20                  25                  30

Arg Asp Phe Trp Tyr Pro Pro Gly Arg Ser Pro Thr Glu Ser Phe Val
           35                  40                  45

Ile Arg Leu Glu Asn Cys His Ala Thr Ala Val Gly Lys Ile Val Thr
 50                  55                  60

Leu Thr Phe Lys Gly Thr Glu Ala Ala Leu Pro Gly His Leu Lys
 65                  70                  75                  80

Val Thr Gly Val Asn Ala Gly Arg Leu Gly Ile Ala Leu Leu Asp Thr
                 85                  90                  95

Asp Gly Ser Ser Leu Leu Lys Pro Gly Thr Ser His Asn Lys Gly Gln
                100                 105                 110

Gly Glu Lys Val Thr Gly Asn Ser Leu Glu Leu Pro Phe Gly Ala Tyr
                115                 120                 125

Val Val Ala Thr Pro Glu Ala Leu Arg Thr Lys Ser Val Val Pro Gly
130                 135                 140

Asp Tyr Glu Ala Thr Ala Thr Phe Glu Leu Thr Tyr Arg
145                 150                 155

<210> SEQ ID NO 58
<211> LENGTH: 163
<212> TYPE: PRT
<213> ORGANISM: Escherichia coli

<400> SEQUENCE: 58

Ala Pro Thr Ile Pro Gln Gly Gln Gly Lys Val Thr Phe Asn Gly Thr
  1               5                  10                  15

Val Val Asp Ala Pro Cys Ser Ile Ser Gln Lys Ser Ala Asp Gln Ser
               20                  25                  30

Ile Asp Phe Gly Gln Leu Ser Lys Ser Phe Leu Glu Ala Gly Gly Val
           35                  40                  45

Ser Lys Pro Met Asp Leu Asp Ile Glu Leu Val Asn Cys Asp Ile Thr
 50                  55                  60

Ala Phe Lys Gly Gly Asn Gly Ala Lys Lys Gly Thr Val Lys Leu Ala
 65                  70                  75                  80

Phe Thr Gly Pro Ile Val Asn Gly His Ser Asp Glu Leu Asp Thr Asn
                 85                  90                  95

Gly Gly Thr Gly Thr Ala Ile Asx Asx Gln Gly Ala Gly Lys Asn Asx
                100                 105                 110

Asx Phe Asp Gly Ser Glu Gly Asp Ala Asn Thr Leu Lys Asp Gly Glu
                115                 120                 125

Asn Val Leu His Tyr Thr Ala Val Val Lys Lys Ser Ser Ala Val Gly
                130                 135                 140

Ala Ala Val Thr Glu Gly Ala Phe Ser Ala Val Ala Asn Phe Asn Leu
145                 150                 155                 160

Thr Tyr Gln

<210> SEQ ID NO 59
<211> LENGTH: 148
<212> TYPE: PRT
<213> ORGANISM: Escherichia coli

<400> SEQUENCE: 59
```

```
Asp Asn Leu Thr Phe Arg Gly Lys Leu Ile Ile Pro Ala Cys Thr Val
  1               5                  10                  15

Ser Asn Thr Thr Val Asp Trp Gln Asp Val Glu Ile Gln Thr Leu Ser
             20                  25                  30

Gln Asn Gly Asn His Glu Lys Glu Phe Thr Val Asn Met Arg Cys Pro
         35                  40                  45

Tyr Asn Leu Gly Thr Met Lys Val Thr Ile Thr Ala Thr Asn Thr Tyr
     50                  55                  60

Asn Asn Ala Ile Leu Val Gln Asn Thr Ser Asn Thr Ser Ser Asp Gly
 65                  70                  75                  80

Leu Leu Val Tyr Leu Tyr Asn Ser Asn Ala Gly Asn Ile Gly Thr Ala
                 85                  90                  95

Ile Thr Leu Gly Thr Pro Phe Thr Pro Gly Lys Ile Thr Gly Asn Asn
                100                 105                 110

Ala Asp Lys Thr Ile Ser Leu His Ala Lys Leu Gly Tyr Lys Gly Asn
            115                 120                 125

Met Gln Asn Leu Ile Ala Gly Pro Phe Ser Ala Thr Ala Thr Leu Val
        130                 135                 140

Ala Ser Tyr Ser
145

<210> SEQ ID NO 60
<211> LENGTH: 148
<212> TYPE: PRT
<213> ORGANISM: Escherichia coli

<400> SEQUENCE: 60

Asp Val Gln Ile Asn Ile Arg Gly Asn Val Tyr Ile Pro Pro Cys Thr
  1               5                  10                  15

Ile Asn Asn Gly Gln Asn Ile Val Val Asp Phe Gly Asn Ile Asn Pro
             20                  25                  30

Glu His Val Asp Asn Ser Arg Gly Glu Val Thr Lys Thr Ile Ser Ile
         35                  40                  45

Ser Cys Pro Tyr Lys Ser Gly Ser Leu Trp Ile Lys Val Thr Gly Asn
     50                  55                  60

Thr Met Gly Gly Gly Gln Asn Asn Val Leu Ala Thr Asn Ile Thr His
 65                  70                  75                  80

Phe Gly Ile Ala Leu Tyr Gln Gly Lys Gly Met Ser Thr Pro Leu Ile
                 85                  90                  95

Leu Gly Asn Gly Ser Gly Asn Gly Tyr Gly Val Thr Ala Gly Leu Asp
                100                 105                 110

Thr Ala Arg Ser Thr Phe Thr Phe Thr Ser Val Pro Phe Arg Asn Gly
            115                 120                 125

Ser Gly Ile Leu Asn Gly Gly Asp Phe Gln Thr Thr Ala Ser Met Ser
        130                 135                 140

Met Ile Tyr Asn
145

<210> SEQ ID NO 61
<211> LENGTH: 218
<212> TYPE: PRT
<213> ORGANISM: Escherichia coli

<400> SEQUENCE: 61

Ala Val Ser Leu Asp Arg Thr Arg Ala Val Phe Asp Gly Ser Glu Lys
  1               5                  10                  15
```

-continued

Ser Met Thr Leu Asp Ile Ser Asn Asp Asn Lys Gln Leu Pro Tyr Leu
            20                  25                  30

Ala Gln Ala Trp Ile Glu Asn Glu Asn Gln Glu Lys Ile Ile Thr Gly
        35                  40                  45

Pro Val Ile Ala Thr Pro Pro Val Gln Arg Leu Glu Pro Gly Ala Lys
    50                  55                  60

Ser Met Val Arg Leu Ser Thr Thr Pro Asp Ile Ser Lys Leu Pro Gln
65                  70                  75                  80

Asp Arg Glu Ser Leu Phe Tyr Phe Asn Leu Arg Glu Ile Pro Pro Arg
                85                  90                  95

Ser Glu Lys Ala Asn Val Leu Gln Ile Ala Leu Gln Thr Lys Ile Lys
            100                 105                 110

Leu Phe Tyr Arg Pro Ala Ala Ile Lys Thr Arg Pro Asn Glu Val Trp
        115                 120                 125

Gln Asp Gln Leu Ile Leu Asn Lys Val Ser Gly Gly Tyr Arg Ile Glu
    130                 135                 140

Asn Pro Thr Pro Tyr Tyr Val Thr Val Ile Gly Leu Gly Gly Ser Glu
145                 150                 155                 160

Lys Gln Ala Glu Glu Gly Glu Phe Glu Thr Val Met Leu Ser Pro Arg
                165                 170                 175

Ser Glu Gln Thr Val Lys Ser Ala Asn Tyr Asn Thr Pro Tyr Leu Ser
            180                 185                 190

Tyr Ile Asn Asp Tyr Gly Gly Arg Pro Val Leu Ser Phe Ile Cys Asn
        195                 200                 205

Gly Ser Arg Cys Ser Val Lys Lys Glu Lys
    210                 215

<210> SEQ ID NO 62
<211> LENGTH: 278
<212> TYPE: PRT
<213> ORGANISM: Escherichia coli

<400> SEQUENCE: 62

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Phe Gln Phe
    130                 135                 140

Val Trp Asn Ile Tyr Ala Asn Asn Asp Val Val Pro Thr Gly Gly
145                 150                 155                 160

Cys Asp Val Ser Ala Arg Asp Val Thr Val Thr Leu Pro Asp Tyr Pro

```
                        165                 170                 175
Gly Ser Val Pro Ile Pro Leu Thr Val Tyr Cys Ala Lys Ser Gln Asn
            180                 185                 190

Leu Gly Tyr Tyr Leu Ser Gly Thr Thr Ala Asp Ala Gly Asn Ser Ile
            195                 200                 205

Phe Thr Asn Thr Ala Ser Phe Ser Pro Ala Gln Val Gly Val Gln Leu
            210                 215                 220

Thr Arg Asn Gly Thr Ile Ile Pro Ala Asn Asn Thr Val Ser Leu Gly
225                 230                 235                 240

Ala Val Gly Thr Ser Ala Val Ser Leu Gly Leu Thr Ala Asn Tyr Ala
            245                 250                 255

Arg Thr Gly Gly Gln Val Thr Ala Gly Asn Val Gln Ser Ile Ile Gly
            260                 265                 270

Val Thr Phe Val Tyr Gln
            275

<210> SEQ ID NO 63
<211> LENGTH: 161
<212> TYPE: PRT
<213> ORGANISM: Escherichia coli

<400> SEQUENCE: 63

Asp Thr Thr Pro Thr Thr Val Asn Gly Gly Thr Val His Phe Lys Gly
1               5                   10                  15

Glu Val Val Asn Ala Ala Cys Ala Val Asp Ala Gly Ser Val Asp Gln
            20                  25                  30

Thr Val Gln Leu Gly Gln Val Arg Thr Ala Thr Leu Lys Gln Ala Gly
        35                  40                  45

Ala Thr Ser Ser Ala Val Gly Phe Asn Ile Gln Leu Asn Asn Cys Asp
    50                  55                  60

Thr Thr Val Ala Thr Lys Ala Ala Val Ala Phe Leu Gly Thr Ala Ile
65                  70                  75                  80

Asp Ser Thr His Pro Lys Val Leu Ala Leu Gln Ser Ser Ala Ala Gly
                85                  90                  95

Ser Ala Thr Asn Val Gly Val Gln Ile Leu Asp Arg Thr Gly Asn Glu
            100                 105                 110

Leu Thr Leu Asp Gly Ala Thr Phe Ser Ala Glu Thr Thr Leu Asn Asn
        115                 120                 125

Gly Thr Asn Thr Ile Pro Phe Gln Ala Arg Tyr Phe Ala Thr Gly Ala
    130                 135                 140

Ala Thr Pro Gly Ala Ala Asn Ala Asp Ala Thr Phe Lys Val Gln Tyr
145                 150                 155                 160

Gln

<210> SEQ ID NO 64
<211> LENGTH: 153
<212> TYPE: PRT
<213> ORGANISM: Escherichia coli

<400> SEQUENCE: 64

Asp Ser Thr Ile Thr Ile Arg Gly Tyr Val Arg Asp Asn Gly Cys Ser
1               5                   10                  15

Val Ala Ala Glu Ser Thr Asn Phe Thr Val Asp Leu Met Glu Asn Ala
            20                  25                  30

Ala Lys Gln Phe Asn Asn Ile Gly Ala Thr Thr Pro Val Val Pro Phe
        35                  40                  45
```

```
Arg Ile Leu Leu Ser Ser Cys Gly Asn Ala Val Ser Ala Val Lys Val
            50              55                  60

Gly Phe Thr Gly Val Ala Asp Ser His Asn Ala Asn Leu Leu Ala Leu
 65              70                  75                      80

Glu Asn Thr Val Ser Ala Ala Ser Gly Leu Gly Ile Gln Leu Leu Asn
                 85                  90                  95

Glu Gln Gln Asn Gln Ile Pro Leu Asn Ala Pro Ser Ser Ala Leu Ser
             100             105             110

Trp Thr Thr Leu Thr Pro Gly Lys Pro Asn Thr Leu Asn Phe Tyr Ala
             115             120             125

Arg Leu Met Ala Thr Gln Val Pro Val Thr Ala Gly His Ile Asn Ala
             130             135             140

Thr Ala Thr Phe Thr Leu Glu Tyr Gln
145                 150

<210> SEQ ID NO 65
<211> LENGTH: 143
<212> TYPE: PRT
<213> ORGANISM: Escherichia coli

<400> SEQUENCE: 65

Asp Val Thr Ile Thr Val Asn Gly Lys Val Val Ala Lys Pro Cys Thr
  1               5                  10                  15

Val Ser Thr Thr Asn Ala Thr Val Asp Leu Gly Asp Leu Tyr Ser Phe
                 20                  25                  30

Ser Leu Met Ser Ala Gly Ala Ala Ser Ala Trp His Asp Val Ala Leu
             35                  40                  45

Glu Leu Thr Thr Cys Pro Val Gly Thr Ser Arg Val Thr Ala Ser Phe
 50                  55                  60

Ser Gly Ala Ala Asp Ser Ile Gly Tyr Tyr Lys Asn Gln Gly Thr Ala
 65              70                  75                  80

Gln Asn Ile Gln Leu Glu Leu Gln Asp Asp Ser Gly Asn Thr Leu Asn
             85                  90                  95

Thr Gly Ala Thr Lys Thr Val Gln Val Asp Asp Ser Ser Gln Ser Ala
            100                 105             110

His Phe Pro Leu Gln Val Arg Ala Leu Thr Val Asn Gly Gly Ala Thr
            115                 120             125

Gln Gly Thr Ile Gln Ala Val Ile Ser Ile Thr Tyr Thr Tyr Ser
            130                 135             140
```